United States Patent [19]

Kardorff et al.

[11] Patent Number: 5,374,642
[45] Date of Patent: Dec. 20, 1994

[54] HYDROQUINONE DIETHERS, THEIR PREPARATION AND THEIR USE

[75] Inventors: Uwe Kardorff, Mannheim; Christoph Nuebling, Hassloch; Hans Theobald, Limburgerhof; Thomas Kuekenhoehner, Frankenthal; Hans-Juergen Neubauer, Muenster-Hiltrup; Joachim Leyendecker, Ladenburg; Christoph Kuenast, Otterstadt; Peter Hofmeister, Neustadt; Wolfgang Krieg, Weingarten, all of Germany

[73] Assignee: BASF Aktiengesellschaft, Ludwigshafen, Germany

[21] Appl. No.: 34,649

[22] Filed: Mar. 22, 1993

Related U.S. Application Data

[63] Continuation of Ser. No. 681,256, Apr. 8, 1991, abandoned.

[30] Foreign Application Priority Data

Apr. 19, 1990 [DE] Germany ............................. 4012409

[51] Int. Cl.5 .................. C07D 413/12; C07D 417/12; A01N 43/82
[52] U.S. Cl. ..................................... 514/363; 514/364; 514/397; 514/378; 548/136; 548/131; 548/143; 548/217; 548/312.4; 548/315.1; 548/313.7; 548/312.7; 548/365.7

[58] Field of Search ............... 514/363, 364, 378, 397; 548/131, 136, 143, 247, 312.4, 312.7, 313.7, 315.1, 363.7

[56] References Cited

U.S. PATENT DOCUMENTS 3,853,907 12/1974 Edwards ............................. 548/336
4,171,365 10/1979 Diana ................................. 548/374

OTHER PUBLICATIONS

Indian Journal of Chemistry, vol. 10, pp. 38–40 (1972), Murthy et al., "Synthesis of 3-Phenyl-5-aryloxymethylisoxazoles and Their UV Spectra and Physiological Activity".

Primary Examiner—Robert Gerstl
Attorney, Agent, or Firm—Keil & Weinkauf

[57] ABSTRACT

Hydroquinone diethers of the general formula I

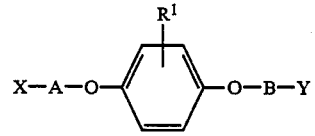

where $R^1$ is hydrogen, halogen or $C_1$-$C_6$-alkyl, A and B are each unsubstituted or substituted methylene, ethylene or propylene and X and Y are each unsubstituted or substituted hetaryl, processes for their preparation and pesticides.

20 Claims, No Drawings

HYDROQUINONE DIETHERS, THEIR PREPARATION AND THEIR USE

This application is a continuation of application Ser. No. 681,256, filed on Apr. 8, 1991, now abandoned.

The present invention relates to hydroquinone diethers of the formula I

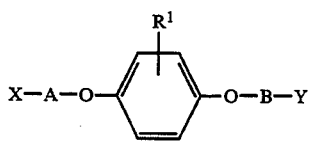

where $R^1$ is hydrogen, halogen or $C_1$-$C_6$-alkyl,

A and B are each methylene, ethylene or propylene, where these groups may carry one or two $C_1$-$C_3$-alkyl radicals, and X and Y are each a 5-membered heteroaromatic structure containing, in addition to carbon atoms, from 1 to 3 hetero atoms from the group consisting of nitrogen, oxygen and sulfur, which may carry from one to three of the following groups: halogen, $C_1$-$C_6$-alkyl, $C_1$-$C_4$-haloalkyl, $C_1$-$C_6$-alkoxy, $C_1$-$C_4$-haloalkoxy, $C_1$-$C_3$-alkoxy-$C_1$-$C_4$-alkyl, $C_3$-$C_8$-cycloalkyl, $C_2$-$C_8$-alkenyl, aryl or aryl-$C_1$-$C_{10}$-alkyl, where these aromatic radicals in turn may carry from one to five halogen atoms and from one to three of the following groups: $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio.

The present invention furthermore relates to a process for the preparation of the compounds I and pesticides which contain the compounds I.

The literature discloses 4-aryloxyphenol hetaryl methyl ethers (EP-A 239,047, EP-A 287,959, EP-A 289,919, EP-A 353,571 and EP-A 353,674) having insecticidal activity.

It is an object of the present invention to provide novel hydroquinone diethers having improved insecticidal properties.

We have found that this object is achieved by the hydroquinone diethers of the formula I which are defined at the outset and a process for their preparation. We have also found pesticides and methods for controlling pests with these agents.

The hydroquinone diethers of the formula I can be prepared by various methods. They are obtained, for example, by the following process:

A 4-hydroxyphenol ether of the general formula II is etherified in a conventional manner in an inert organic solvent in the presence of a base with a heterarylalkyl derivative of the formula IIIa or IIIb, the resulting diether derivative IVa or IVb is converted in a conventional manner, by eliminating the protective group R, into the corresponding monoether Va or Vb, which is then etherified in a conventional manner with a heterarylalkyl derivative IIIa or IIIb to give I.

The reaction steps are shown in the scheme below:

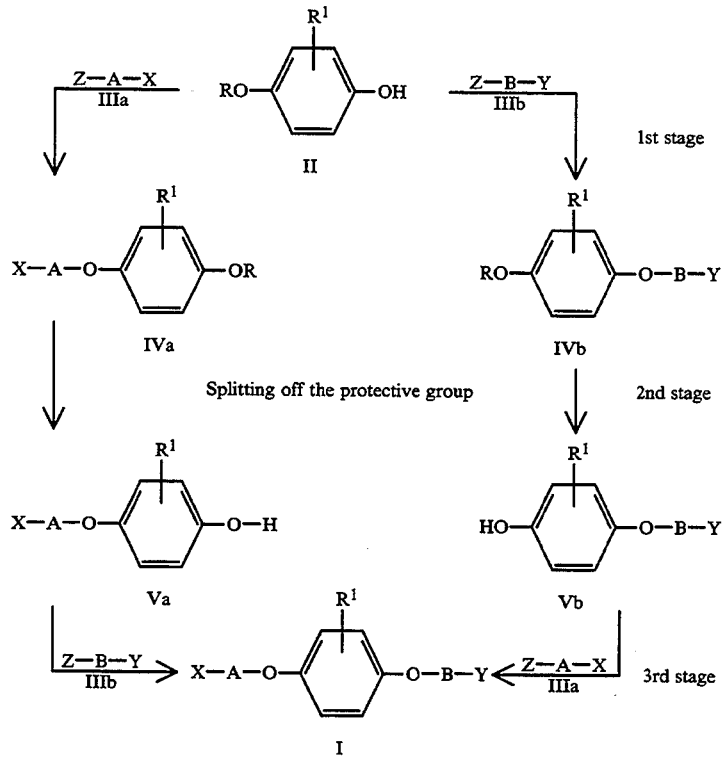

In formula II, R is a protective group which is inert under the reaction conditions, such as straight-chain or branched $C_1$-$C_6$-alkyl, e.g. tert-butyl, benzyl or silyl which is trisubstituted by $C_1$-$C_4$-alkyl or aryl, e.g. trimethylsilyl, tert-butyldimethylsilyl, phenyldimethylsilyl or tert-butyldiphenylsilyl, in particular tertbutyldimethylsilyl.

In formulae IIIa and IIIb, Z is a nucleofugic leaving group, for example a sulfonyl radical, such as methylsulfonyl, trifluoromethylsulfonyl, phenylsulfonyl or p-tolylsulfonyl, halogen, such as chlorine, bromine or iodine, in particular chlorine or bromine.

The etherification reactions of II with IIIa or IIIb (1st stage) or of Va or Vb with IIIb or IIIa (3rd stage) are generally carried out in an inert organic solvent in the presence of a base at from −50° to 150° C., in particular from −20° to 120° C.

The reactions usually take place at a sufficient rate at above −20° C. In general, there is no need to exceed 120° C. Since the reactions take place with evolution of heat in some cases, it may be advantageous to provide a means of cooling.

Examples of suitable solvents are hydrocarbons, such as pentane, hexane, benzene, toluene and xylenes, halohydrocarbons, such as methylene chloride, ethylene chloride, chloroform or chlorobenzene, ethers, such as diethyl ether, di-n-butyl ether, methyl tert-butyl ether, tetrahydrofuran or dioxane, ketones, such as acetone or methyl ethyl ketone, nitriles, such as acetonitrile, alcohols, such as methanol or ethanol, aprotic dipolar solvent, such as dimethylformamide, dimethyl sulfoxide or pyridine, in particular acetonitrile, ethanol, dimethylformamide and corresponding mixtures.

Not less than an equivalent amount of a base is usually used, but the base may also be used in excess or, if necessary, as a solvent. Examples of suitable bases are hydroxides of alkali metals and of alkaline earth metals, such as sodium hydroxide, potassium hydroxide and calcium hydroxide, alcoholates of alkali metals and of alkaline earth metals, such as sodium methylate, sodium ethylate, calcium methylate or potassium tert-butylate, alkali metal or alkaline earth metal hydrides, such as sodium hydride, potassium hydride or calcium hydride, alkali metal or alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, aromatic amines, such as pyridine or pyrrole and, if required, also alkyllithium compounds, such as n-butyllithium, in particular potassium hydroxide, potassium carbonate, sodium methylate, sodium ethylate, potassium tertbutylate and sodium hydride.

The starting materials are usually reacted with one another in stoichiometric amounts, but, in order to increase the yield, it may be advantageous to use one of the starting materials in an excess of from 0.1 to 10, in particular from 0.2 to 1.5, mole equivalents. It may also be advantageous to add from 5 to 20 mol % of potassium iodide.

The reaction mixtures are usually worked up in a conventional manner, for example by adding water, separating the phases and purifying the crude products by means of column chromatography. Some of the novel compounds of the formula I are obtained in the form of colorless or slightly brownish, viscous oils, which can be freed from the final volatile constituents by prolonged heating at moderately elevated temperatures under reduced pressure (incipient distillation) and can be purified in this manner. If the compounds of the formula IVa, IVb or I are obtained in crystalline form, they can be purified by recrystallization.

Splitting off of the protective group R from the diethers IVa or IVb can likewise be effected in a conventional manner in an inert organic solvent in the presence of an acid at from −20° to 120° C., preferably from 20° to 100° C.

Solvents such as the abovementioned ones, in particular methanol, ethanol, chloroform and dioxane and corresponding mixtures, are generally suitable for this purpose.

Suitable acids are inorganic acids, such as hydrofluoric acid, hydrochloric acid, hydrobromic acid, sulfuric acid or perchloric acid, and organic acids, such as formic acid, acetic acid, propionic acid, oxalic acid, citric acid or trifluoroacetic acid, in particular hydrochloric acid, hydrobromic acid or trifluoroacetic acid.

The acids are added in general in catalytic amounts but may also be used in equimolar amounts, in excess or, if required, as solvents.

The reaction mixtures are worked up in a conventional manner, for example as described above for the etherification.

Symmetric hydroquinone diethers I (A—X=B—Y) are particularly advantageously obtainable in a single-stage reaction by etherification of unsubstituted or substituted hydroquinones by the etherification methods described above.

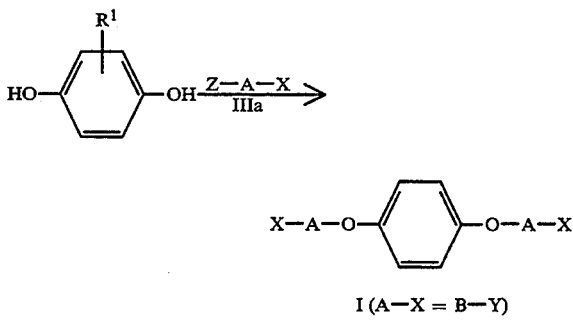

I (A—X = B—Y)

The hetarylalkyl derivatives of the formulae IIIa and IIIb are either known or are commercially available or can be prepared by generally known chemical methods.

Processes for the preparation of thiophene derivatives are described in, for example, Comprehensive Heterocyclic Chemistry, R. Katritzky and W. Rees, Vol. 4, page 863 et seq., Pergamon Press 1984, and thiazole derivatives, oxazole derivatives, isothiazole derivatives, thiadiazole derivatives and oxadiazole derivatives are described in, for example Comprehensive Heterocyclic Chemistry, R. Katritzky and W. Rees, Vol. 6, pages 131, 177, 235, 365, 427 and 545 et seq., Pergamon Press 1984, imidazole derivatives are described in, for example, Advances in Heterocyclic Chemistry, 27 (1980), 242 et seq., pyrazole and triazole derivatives are described in, for example, Comprehensive Heterocyclic Chemistry, R. Katrizky and W. Rees, Vol. 5, pages 167 and 733 et seq., Pergamon Press 1984, and isoxazole derivatives are described in, for example, DE-A-25 49 962 and DE-A-27 54 832, and some N-methylazoles are disclosed in Heterocycles 24 (1986), 2233-2237 or can be obtained by the method described there, by reacting the azole with paraformaldehyde.

In view of the biological action of the hydroquinone diethers of the formula I, suitable substituents are the following radicals:

$R^1$ is hydrogen, halogen, such as fluorine, chlorine, bromine or iodine, in particular fluorine, alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1- methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1$–$C_4$-alkyl, in particular methyl, ethyl or isopropyl, A and B independently of one another are each methylene, ethylene or propylene, where these groups may carry one or two alkyl radicals of 1 to 3 carbon atoms as stated above for $R^1$, in particular methyl or ethyl, and X and Y independently of one another are each a 5-membered heteroaromatic structure containing, in addition to carbon atoms, from 1 to 3 hetero atoms from the group consisting of nitrogen, oxygen and sulfur, such as furanyl, thienyl, pyrrolyl, isoxazolyl, isothiazolyl, pyrazolyl, oxazolyl, thiazolyl, imidazolyl, oxa-2,4-diazolyl, oxa-3,4-diazolyl, thia-2,4-diazolyl, thia-3,4-diazolyl or triazolyl, where these rings may be bonded to the radical A or B via a carbon ring member or, where present, a nitrogen ring member; these heteroaromatic structures may furthermore carry from one to three of the following groups on the carbon ring members and, where present, on the valent nitrogen ring members:

alkyl as stated for $R^1$, preferably $C_1$–$C_4$-alkyl, in particular methyl, ethyl or 1-methylethyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular trifluoromethyl or trichloromethyl, alkoxy, such as methoxy, ethoxy, n-propoxy, 2-methylethoxy, n-butoxy, 1-methylpropoxy, 2-methylpropoxy, 1,1-dimethylethoxy, pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 1,1,2-trimethylpropoxy, 1,2,2-trimethylpropoxy, 1-ethyl-1-methylpropoxy or 1-ethyl-2-methylpropoxy, preferably $C_1$–$C_4$-alkoxy, in particular methoxy, ethoxy or 1-methylethoxy, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy or pentafluoroethoxy, alkoxyalkyl, such as methoxymethyl, methoxyethyl, 2-methoxyethyl, 1-methoxypropyl, 2-methoxypropyl, 1-methoxy-1-methylethyl, 2-methoxy-1-methylethyl, 1-methoxybutyl, 2-methoxybutyl, 1-methoxy-1-methylpropyl, 1-methoxy-2-methylpropyl, 2-methoxy-1-methylpropyl, 2-methoxy-2-methylpropyl, ethoxymethyl, 1-ethoxyethyl, 2-ethoxyethyl, 1-ethoxypropyl, 2-ethoxypropyl, 1-ethoxy-1-methylethyl, 2-ethoxy-1-methylethyl, 1-ethoxybutyl, 2-ethoxybutyl, 1-ethoxy-1-methylpropyl, 1-ethoxy-2-methylpropyl, 2-ethoxy-1-methylpropyl or 2-ethoxy-2-methylpropyl, in particular methoxymethyl or ethoxymethyl, cycloalkyl, such as cyclopropyl, cyclobutyl, cyclopentyl, cyclohexyl, cycloheptyl or cyclooctyl, preferably cyclopropyl, cyclopentyl or cyclohexyl, in particular cyclopropyl, alkenyl, in particular ethenyl, 1-propenyl, 2-propenyl, 2-butenyl, 1-methyl-2-butenyl, 2-methyl-2-butenyl, 3-methyl-2-butenyl, 2-pentenyl, 3-pentenyl or 1,2-dimethyl-2-propenyl, particularly preferably ethenyl, 2-propenyl, 2-butenyl or 3-methyl-2-butenyl, aryl, such as phenyl, 1-naphthyl or 2-naphthyl, preferably phenyl, arylalkyl, such as $C_1$–$C_{10}$-alkyl which is substituted by phenyl, 1-naphthyl or 2-naphthyl, preferably $C_1$–$C_6$-alkyl as stated for $R^1$, in particular phenyl-substituted $C_1$–$C_4$-alkyl, such as benzyl, 1-phenylethyl, 2-phenylethyl, 1-phenylpropyl, 2-phenylpropyl, 1-methyl-1-phenylethyl, 1-methyl-2-phenylethyl or 1,1-dimethyl-2-phenylethyl, where the aromatic radicals in turn may carry from one to five halogen atoms as stated for $R^1$, in particular fluorine and/or chlorine and/or from one to three of the following groups:

$C_1$–$C_4$-alkyl as stated for $R^1$, in particular methyl, ethyl, 1-methylethyl or 1,1-dimethylethyl, $C_1$–$C_4$-haloalkyl as stated above in general and in particular, $C_1$–$C_4$-alkoxy as stated above, in paticular methoxy, ethoxy or 1-methylethoxy, $C_1$–$C_4$-haloalkoxy as stated above in general and in particular, $C_2$–$C_4$-alkenyl as stated above in general and in particular and/or alkylthio, such as methylthio, ethylthio, propylthio, 1-methylethylthio, butylthio, 1-methylpropylthio, 2-methylproylthio or 1,1-dimethylethylthio, in articular methylthio; in addition to the abovementioned groups, the 5-membered hetaryl radicals (X, Y) may furthermore carry from one to three halogen atoms, such as fluorine, chlorine, bromine or iodine, in particular fluorine, chlorine or bromine, on the carbon ring members.

5-Membered heteroaromatic structures which are particularly preferred substituents X or Y are listed below, for the sake of clarity the possible substituents not being drawn in; the bond to A or B is denoted by

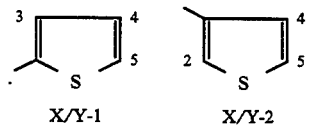

X/Y-1    X/Y-2

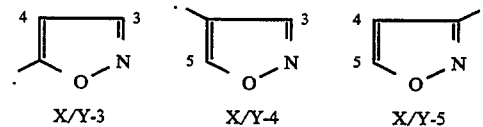

X/Y-3    X/Y-4    X/Y-5

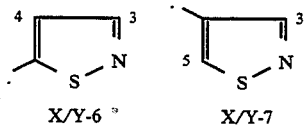

X/Y-6    X/Y-7

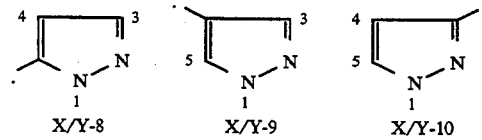

X/Y-8    X/Y-9    X/Y-10

-continued

X/Y-11 (pyrazole, positions 3,4,5, N)

X/Y-12, X/Y-13, X/Y-14 (isoxazole isomers)

X/Y-15, X/Y-16, X/Y-17 (isothiazole isomers)

X/Y-18, X/Y-19, X/Y-20 (imidazole isomers)

X/Y-21 (pyrazole)

X/Y-22, X/Y-23, X/Y-24 (oxadiazole/thiadiazole isomers)

X/Y-25 (thiadiazole)

X/Y-26, X/Y-27 (triazole isomers)

X/Y-28, X/Y-29, X/Y-30 (triazole isomers)

Examples of the particularly preferred compounds of the general formulae I.A, I.B, I.C, I.D, I.E, I.F and I.G are shown in Tables A to G below.

Structures I.A – I.G shown with phenyl ring bearing $R^1$, and groups A—O and O—B—Y substituents.

TABLE A
(for structure I.A)

| A | $R^1$ | B | Y | Substituent on Y |
|---|---|---|---|---|
| $CH_2$ | H | $CH_2$ | X/Y-1 | |
| $CH(CH_3)$ | H | $CH_2$ | X/Y-1 | |
| $CH(CH_2CH_3)$ | H | $CH_2$ | X/Y-1 | |
| $CH_2$ | H | $CH(CH_3)$ | X/Y-1 | |
| $CH_2$ | H | $CH(CH_2CH_3)$ | X/Y-1 | |
| $CH_2$ | 3-$CH_3$ | $CH_2$ | X/Y-1 | |
| $CH_2$ | 3-F | $CH_2$ | X/Y-1 | |
| $CH_2$ | H | $CH_2$ | X/Y-1 | 5-$CH_3$ |
| $CH_2$ | H | $CH_2$ | X/Y-1 | 4-$CH_3$ |
| $CH_2$ | H | $CH_2$ | X/Y-1 | 3-$CH_3$ |
| $CH_2$ | H | $CH_2$ | X/Y-1 | 5-Cyclopropyl |
| $CH_2$ | H | $CH_2$ | X/Y-1 | 4-Cyclopropyl |
| $CH_2$ | H | $CH_2$ | X/Y-1 | 3-Cyclopropyl |
| $CH_2$ | H | $CH_2$ | X/Y-1 | 5-Cl |
| $CH_2$ | H | $CH_2$ | X/Y-1 | 5-Br |
| $CH_2$ | H | $CH_2$ | X/Y-1 | 4-Cl |
| $CH_2$ | H | $CH_2$ | X/Y-1 | 4-Br |
| $CH_2$ | H | $CH_2$ | X/Y-1 | 4,5-Cl,Cl |
| $CH_2$ | H | $CH_2$ | X/Y-1 | 4-$OCH_2CH_3$ |

TABLE A-continued (for structure I.A)

| A | R¹ | B | Y | Substituent on Y |
|---|---|---|---|---|
| CH(CH₃) | H | CH₂ | X/Y-1 | 5-Br |
| CH(CH₃) | H | CH₂ | X/Y-1 | 4,5-Cl,Cl |
| CH(CH₃) | H | CH₂ | X/Y-1 | 4-Cl |
| CH₂ | H | CH(CH₃) | X/Y-1 | 5-Br |
| CH₂ | H | CH(CH₃) | X/Y-1 | 4,5-Cl,Cl |
| CH(CH₃) | H | CH(CH₃) | X/Y-1 | — |
| CH(CH₃ | H | CH(CH₃) | X/Y-1 | 4,5-Cl,Cl |
| CH(CH₃) | 3-F | CH(CH₃) | X/Y-1 | — |
| CH(CH₃) | 3-F | CH(CH₃) | X/Y-1 | 5-Br |
| CH₂CH₂ | H | CH₂ | X/Y-1 | 5-Br |
| CH₂CH₂ | H | CH₂CH₂ | X/Y-1 | 4,5-Cl,Cl |
| CH₂CH₂CH₂ | H | CH₂ | X/Y-1 | 5-Br |
| CH₂CH₂ | H | CH₂CH₂CH₂ | X/Y-1 | 4,5-Cl,Cl |
| CH₂CH(CH₃) | H | CH₂CH₂ | X/Y-1 | 4,5-Cl,Cl |
| CH₂CH₂ | 3-F | CH₂CH(CH₃) | X/Y-1 | 5-Br |
| CH₂ | H | CH₂ | X/Y-2 | — |
| CH₂ | H | CH₂ | X/Y-2 | 4-Cyclopropyl |
| CH₂ | H | CH₂ | X/Y-2 | 5-Cyclopropyl |
| CH₂ | H | CH₂ | X/Y-2 | 5-Cl |
| CH₂ | H | CH₂ | X/Y-2 | 4,5-Cl,Cl |
| CH₂ | H | CH₂ | X/Y-2 | 4,5-Br,Br |
| CH₂ | H | CH₂ | X/Y-2 | 4-CH₃ |
| CH₂ | H | CH₂ | X/Y-2 | 5-CH₃ |
| CH₂ | H | CH₂ | X/Y-2 | 4-OCH₃ |
| CH₂ | H | CH₂ | X/Y-2 | 5-OCH₃ |
| CH(CH₃) | H | CH₂ | X/Y-2 | 4,5-Cl,Cl |
| CH(CH₃) | H | CH₂ | X/Y-2 | 4,5-Br,Br |
| CH₂ | H | CH(CH₃) | X/Y-2 | 4,5-Cl,Cl |
| CH₂ | H | CH(CH₃) | X/Y-2 | 4,5-Br,Br |
| CH(CH₃) | H | CH(CH₃) | X/Y-2 | 4,5-Cl,Cl |
| CH(CH₃) | H | CH(CH₃) | X/Y-2 | 4,5-Br,Br |
| CH(CH₃) | 3-F | CH(CH₃) | X/Y-2 | 4,5-Cl,Cl |
| CH(CH₃) | 3-F | CH(CH₃) | X/Y-2 | 4,5-Br,Br |
| CH₂CH₂ | H | CH₂ | X/Y-2 | 4,5-Cl,Cl |
| CH₂CH₂ | H | CH₂CH₂ | X/Y-2 | 4,5-Br,Br |
| CH₂CH₂CH₂ | H | CH₂ | X/Y-2 | 4,5-Cl,Cl |
| CH₂CH₂ | H | CH₂CH₂CH₂ | X/Y-2 | 4,5-Br,Br |
| CH₂CH(CH₃) | H | CH₂CH₂ | X/Y-2 | 4,5-Br,Br |
| CH₂CH₂ | 3-F | CH₂CH(CH₃) | X/Y-2 | 4,5-Cl,Cl |
| CH₂ | H | CH₂ | X/Y-15 | — |
| CH₂ | H | CH₂ | X/Y-15 | 2-CH₃ |
| CH₂ | H | CH₂ | X/Y-15 | 2-Cyclopropyl |
| CH₂ | H | CH₂ | X/Y-15 | 2-OCH₂CH₃ |
| CH₂ | H | CH₂ | X/Y-15 | 2-Cl |
| CH(CH₃) | H | CH₂ | X/Y-15 | 2-Cyclopropyl |
| CH(CH₃) | H | CH₂ | X/Y-15 | 2-OCH₂CH₃ |
| CH₂ | H | CH(CH₃) | X/Y-15 | 2-Cyclopropyl |
| CH₂ | H | CH(CH₃) | X/Y-15 | 2-OCH₂CH₃ |
| CH(CH₃) | H | CH(CH₃) | X/Y-15 | 2-Cyclopropyl |
| CH(CH₃) | H | CH(CH₃) | X/Y-15 | 2-OCH₂CH₃ |
| CH(CH₃) | 3-F | CH(CH₃) | X/Y-15 | 2-Cyclopropyl |
| CH(CH₃) | 3-F | CH(CH₃) | X/Y-15 | 2-OCH₂CH₃ |
| CH₂CH₂ | H | CH₂CH₂ | X/Y-15 | 2-Cyclopropyl |
| CH₂CH₂ | H | CH₂CH₂ | X/Y-15 | 2-OCH₂CH₃ |
| CH₂CH₂CH₂ | H | CH₂ | X/Y-15 | 2-Cyclopropyl |
| CH₂CH₂ | H | CH₂CH₂CH₂ | X/Y-15 | 2-OCH₂CH₃ |
| CH₂CH(CH₃) | H | CH₂CH₂ | X/Y-15 | 2-Cyclopropyl |
| CH₂CH₂ | 3-F | CH₂CH(CH₃) | X/Y-15 | 2-OCH₂CH₃ |
| CH₂ | H | CH₂ | X/Y-12 | — |
| CH₂ | H | CH₂ | X/Y-12 | 2-CH₃ |
| CH₂ | H | CH₂ | X/Y-12 | 2-Cyclopropyl |
| CH₂ | H | CH₂ | X/Y-12 | 2-OCH₂CH₃ |
| CH(CH₃) | H | CH₂ | X/Y-12 | 2-Cyclopropyl |
| CH(CH₃) | H | CH₂ | X/Y-12 | 2-OCH₂CH₃ |
| CH₂ | H | CH(CH₃) | X/Y-12 | 2-Cyclopropyl |
| CH₂ | H | CH(CH₃) | X/Y-12 | 2-OCH₂CH₃ |
| CH(CH₃) | H | CH(CH₃) | X/Y-12 | 2-Cyclopropyl |
| CH(CH₃) | 3-F | CH(CH₃) | X/Y-12 | 2-OCH₂CH₃ |
| CH₂CH₂ | H | CH₂CH₂ | X/Y-12 | 2-Cyclopropyl |
| CH₂CH₂ | H | CH₂CH₂ | X/Y-12 | 2-OCH₂CH₃ |
| CH₂CH₂CH₂ | H | CH₂ | X/Y-12 | 2-Cyclopropyl |
| CH₂CH₂ | H | CH₂CH₂CH₂ | X/Y-12 | 2-OCH₂CH₃ |
| CH₂CH(CH₃) | H | CH₂CH₂ | X/Y-12 | 2-Cyclopropyl |
| CH₂CH₂ | 3-F | CH₂CH(CH₃) | X/Y-12 | 2-OCH₂CH₃ |
| CH₂ | H | CH₂ | X/Y-18 | 1-CH₃ |
| CH₂ | H | CH₂ | X/Y-18 | 1,4-(CH₃)₂ |
| CH₂ | H | CH₂ | X/Y-18 | 1,2,4-(CH₃)₂ |
| CH₂ | H | CH₂ | X/Y-18 | 1-CH₃, 2-Cyclopropyl |
| CH(CH₃) | H | CH₂ | X/Y-18 | 1-CH₃, 2-Cyclopropyl |
| CH(CH₃) | H | CH₂ | X/Y-18 | 1,2,4-(CH₃)₃ |
| CH₂ | H | CH(CH₃) | X/Y-18 | 1-CH₃, 2-Cyclopropyl |
| CH₂ | H | CH(CH₃) | X/Y-18 | 1,2,4-(CH₃)₃ |
| CH(CH₃) | H | CH(CH₃) | X/Y-18 | 1-CH₃, 2-Cyclopropyl |
| CH(CH₃) | 3-F | CH(CH₃) | X/Y-18 | 1,2,4-(CH₃)₃ |
| CH₂CH₂ | H | CH₂ | X/Y-18 | 1-CH₃, 2-Cyclopropyl |
| CH₂CH₂ | H | CH₂CH₂ | X/Y-18 | 1,2,4-(CH₃)₂ |
| CH₂CH₂CH₂ | H | CH₂ | X/Y-18 | 1-CH₃, 2-Cyclopropyl |
| CH₂CH₂ | H | CH₂CH₂CH₂ | X/Y-18 | 1,2,4-(CH₃)₂ |
| CH₂CH(CH₃) | H | CH₂CH₂ | X/Y-18 | 1-CH₃, 2-Cyclopropyl |
| CH₂CH₂ | 3-F | CH₂CH(CH₃) | X/Y-18 | 1,2,4-(CH₃)₂ |
| CH₂ | H | CH₂ | X/Y-19 | 1-CH₃ |
| CH₂ | H | CH₂ | X/Y-19 | 1,2-(CH₃)₂ |
| CH₂ | H | CH₂ | X/Y-19 | 1,5-(CH₃)₂ |
| CH₂ | H | CH₂ | X/Y-19 | 1-CH₃, 2-Cyclopropyl |
| CH(CH₃) | H | CH₂ | X/Y-19 | 1,2-(CH₃)₂ |
| CH(CH₃) | H | CH₂ | X/Y-19 | 1-CH₃, 2-Cyclopropyl |
| CH₂ | H | CH(CH₃) | X/Y-19 | 1,2-(CH₃)₂ |
| CH₂ | H | CH(CH₃) | X/Y-19 | 1-CH₃, 2-Cyclopropyl |
| CH(CH₃) | H | CH(CH₃) | X/Y-19 | 1,2-(CH₃)₂ |
| CH(CH₃) | H | CH(CH₃) | X/Y-19 | 1-CH₃, 2-Cyclopropyl |
| CH(CH₃) | 3-F | CH₂ | X/Y-19 | 1-CH₃, 2-Cyclopropyl |
| CH₂CH₂ | H | CH₂ | X/Y-19 | 1-CH₃, 2-Cyclopropyl |
| CH₂CH₂ | H | CH₂CH₂ | X/Y-19 | 1,2-(CH₃)₂ |
| CH₂CH₂CH₂ | H | CH₂ | X/Y-19 | 1-CH₃, 2-Cyclopropyl |
| CH₂CH₂ | H | CH₂CH₂CH₂ | X/Y-19 | 1,2-(CH₃)₂ |
| CH₂CH(CH₃) | H | CH₂CH₂ | X/Y-19 | 1-CH₃, 2-Cyclopropyl |
| CH₂CH₂ | 3-F | CH₂CH(CH₃) | X/Y-19 | 1,2-(CH₃)₂ |
| CH₂ | H | CH₂ | X/Y-16 | — |
| CH₂ | H | CH₂ | X/Y-16 | 2-CH₃ |
| CH₂ | H | CH₂ | X/Y-16 | 2-Cyclopropyl |
| CH₂ | H | CH₂ | X/Y-16 | 2-Cl |
| CH₂ | H | CH₂ | X/Y-16 | 2-OCH₂CH₃ |
| CH(CH₃) | H | CH₂ | X/Y-16 | 2-CH₃ |
| CH(CH₃) | H | CH₂ | X/Y-16 | 2-Cyclopropyl |
| CH₂ | H | CH(CH₃) | X/Y-16 | 2-CH₃ |
| CH₂ | H | CH(CH₃) | X/Y-16 | 2-Cyclopropyl |
| CH₂(CH₃) | H | CH(CH₃) | X/Y-16 | 2-CH₃ |
| CH₂(CH₃) | H | CH(CH₃) | X/Y-16 | 2-Cyclopropyl |
| CH₂(CH₃) | 3-F | CH(CH₃) | X/Y-16 | 2-Cyclopropyl |
| CH₂CH₂ | H | CH₂ | X/Y-16 | 2-Cyclopropyl |
| CH₂CH₂ | H | CH₂CH₂ | X/Y-16 | 2-CH₃ |
| CH₂CH₂CH₂ | H | CH₂ | X/Y-16 | 2-Cyclopropyl |
| CH₂CH₂ | H | CH₂CH₂CH₂ | X/Y-16 | 2-CH₃ |
| CH₂CH(CH₃) | H | CH₂CH₂ | X/Y-16 | 2-Cyclopropyl |
| CH₂CH₂ | 3-F | CH₂CH(CH₃) | X/Y-16 | 2-CH₃ |
| CH₂ | H | CH₂ | X/Y-13 | — |
| CH₂ | H | CH₂ | X/Y-13 | 2-CH₃ |
| CH₂ | H | CH₂ | X/Y-13 | 2-Cyclopropyl |
| CH₂ | H | CH₂ | X/Y-13 | 2-OCH₂CH₃ |
| CH(CH₃) | H | CH₂ | X/Y-13 | 2-OCH₂CH₃ |
| CH(CH₃) | H | CH₂ | X/Y-13 | 2-Cyclopropyl |
| CH₂ | H | CH(CH₃) | X/Y-13 | 2-OCH₂CH₃ |
| CH₂ | H | CH(CH₃) | X/Y-13 | 2-Cyclopropyl |
| CH(CH₃) | H | CH(CH₃) | X/Y-13 | 2-OCH₂CH₃ |
| CH(CH₃) | 3-F | CH(CH₃) | X/Y-13 | 2-Cyclopropyl |
| CH₂CH₂ | H | CH₂ | X/Y-13 | 2-Cyclopropyl |
| CH₂CH₂ | H | CH₂ | X/Y-13 | 2-CH₃ |
| CH₂CH₂CH₂ | H | CH₂ | X/Y-13 | 2-Cyclopropyl |
| CH₂CH₂ | H | CH₂CH₂CH₂ | X/Y-13 | 2-CH₃ |
| CH(CH₃)CH₂ | 3-F | CH₂CH₂ | X/Y-13 | 2-Cyclopropyl |

TABLE A-continued (for structure I.A)

| A | R¹ | B | Y | Substituent on Y |
|---|---|---|---|---|
| CH₂CH₂ | H | CH(CH₃)CH₂ | X/Y-13 | 2-CH₃ |
| CH₂ | H | CH₂ | X/Y-6 | — |
| CH₂ | H | CH₂ | X/Y-6 | 3-CH₃ |
| CH₂ | H | CH₂ | X/Y-6 | 3-Cyclopropyl |
| CH₂ | H | CH₂ | X/Y-6 | 3-OCH₂CH₃ |
| CH(CH₃) | H | CH(CH₃) | X/Y-6 | 3-Cyclopropyl |
| CH(CH₃) | 3-F | CH(CH₃) | X/Y-6 | 3-Cyclopropyl |
| CH₂CH₂ | H | CH₂CH₂ | X/Y-6 | 3-Cyclopropyl |
| CH₂CH₂ | H | CH₂CH₂CH₂ | X/Y-6 | 3-CH₃ |
| CH(CH₃)CH₂ | 3-F | CH₂CH₂ | X/Y-6 | 3-Cyclopropyl |
| CH₂CH₂ | H | CH(CH₃)CH₂ | X/Y-6 | 3-Cyclopropyl |
| CH₂ | H | CH₂ | X/Y-8 | 1-CH₃ |
| CH₂ | H | CH₂ | X/Y-8 | 1,3-(CH₃)₂ |
| CH₂ | H | CH₂ | X/Y-8 | 1,4-(CH₃)₂ |
| CH₂ | H | CH₂ | X/Y-8 | 1-CH₃, 3-Cyclopropyl |
| CH(CH₃) | H | CH(CH₃) | X/Y-8 | 1-CH₃, 3-Cyclopropyl |
| CH(CH₃) | 3-F | CH(CH₃) | X/Y-8 | 1-CH₃, 3-Cyclopropyl |
| CH₂CH₂ | H | CH₂CH₂ | X/Y-8 | 1-CH₃, 3-Cyclopropyl |
| CH₂CH₂ | H | CH₂CH₂CH₂ | X/Y-8 | 1,3-(CH₃)₂ |
| CH₂CH(CH₃) | H | CH₂CH₂ | X/Y-8 | 1-CH₃, 3-Cyclopropyl |
| CH(CH₃)CH₂ | 3-F | CH₂CH₂ | X/Y-8 | 1-CH₃, 3-Cyclopropyl |
| CH₂ | H | CH₂ | X/Y-10 | 1-CH₃ |
| CH₂ | H | CH₂ | X/Y-10 | 1,4-(CH₃)₂ |
| CH₂ | H | CH₂ | X/Y-10 | 1-CH₃, 4-OCH₃ |
| CH₂ | H | CH₂ | X/Y-10 | 1-CH₃, 5-CH(CH₃)₂ |
| CH₂ | H | CH₂ | X/Y-10 | 1-CH₃, 5-Cyclopropyl |
| CH(CH₃) | H | CH(CH₃) | X/Y-10 | 1-CH₃, 5-Cyclopropyl |
| CH(CH₃) | 3-F | CH(CH₃) | X/Y-10 | 1,4-(CH₃)₂ |
| CH₂CH₂ | H | CH₂CH₂ | X/Y-10 | 1-CH₃, 5-Cyclopropyl |
| CH₂CH₂ | H | CH₂CH₂CH₂ | X/Y-10 | 1,5-(CH₃)₂ |
| CH₂CH(CH₃) | H | CH₂CH₂ | X/Y-10 | 1-CH₃, 5-Cyclopropyl |
| CH(CH₃)CH₂ | 3-F | CH₂CH₂ | X/Y-10 | 1-CH₃, 5-Cyclopropyl |
| CH₂ | H | CH₂ | X/Y-7 | — |
| CH₂ | H | CH₂ | X/Y-7 | 3-CH₃ |
| CH(CH₃) | H | CH(CH₃) | X/Y-7 | 3-CH₃ |
| CH(CH₃) | 3-F | CH(CH₃) | X/Y-7 | 3-CH₃ |
| CH₂CH₂ | H | CH₂CH₂ | X/Y-7 | 3-CH₃ |
| CH₂CH₂ | 3-F | CH(CH₃)CH₂ | X/Y-7 | 3-CH₃ |
| CH₂ | H | CH₂ | X/Y-9 | 1-CH₃ |
| CH₂ | H | CH₂ | X/Y-9 | 1,3-(CH₃)₂ |
| CH₂ | H | CH₂ | X/Y-9 | 1,5-(CH₃)₂ |
| CH(CH₃) | H | CH(CH₃) | X/Y-9 | 1,3-(CH₃)₂ |
| CH(CH₃) | 3-F | CH(CH₃) | X/Y-9 | 1,5-(CH₃)₂ |
| CH₂CH₂ | H | CH₂CH₂ | X/Y-9 | 1,3-(CH₃)₂ |
| CH₂CH₂ | H | CH₂CH₂CH₂ | X/Y-9 | 1,5-(CH₃)₂ |
| CH₂CH(CH₃) | H | CH₂CH₂ | X/Y-9 | 1,3-(CH₃)₂ |
| CH(CH₃)CH₂ | 3-F | CH₂CH₂ | X/Y-9 | 1,5-(CH₃)₂ |
| CH₂ | H | CH₂ | X/Y-25 | 5-Cyclopropyl |
| CH₂ | H | CH₂ | X/Y-25 | 5-CH₃ |
| CH₂ | H | CH₂ | X/Y-25 | 5-CH₂CH₃ |
| CH₂ | H | CH₂ | X/Y-25 | 5-CH(CH₃)₂ |
| CH₂ | H | CH₂ | X/Y-25 | 5-OCH₃ |
| CH(CH₃) | H | CH(CH₃) | X/Y-25 | 5-Cyclopropyl |
| CH₂(CH₃) | H | CH(CH₃) | X/Y-25 | 5-CH₃ |
| CH(CH₃) | H | CH(CH₃) | X/Y-25 | 5-OCH₂CH₃ |
| CH(CH₃) | 3-F | CH(CH₃) | X/Y-25 | 5-Cyclopropyl |
| CH₂CH₂ | H | CH₂CH₂ | X/Y-25 | 5-Cyclopropyl |
| CH₂CH₂ | H | CH₂CH₂ | X/Y-25 | 5-CH₃ |
| CH₂CH₂CH₂ | H | CH₂ | X/Y-25 | 5-OCH₂CH₃ |
| CH₂CH₂ | 3-F | CH₂CH(CH₃) | X/Y-25 | 5-Cyclopropyl |
| CH₂ | H | CH(CH₃) | X/Y-25 | 5-Cyclopropyl |
| CH₂ | H | CH₂ | X/Y-23 | — |
| CH₂ | H | CH₂ | X/Y-23 | 5-Cyclopropyl |
| CH₂ | H | CH₂ | X/Y-23 | 5-CH₃ |
| CH₂ | H | CH₂ | X/Y-23 | 5-CH(CH₃)₂ |
| CH₂ | H | CH₂ | X/Y-23 | 5-Cl |
| CH₂ | H | CH₂ | X/Y-23 | 5-OCH₂CH₃ |
| CH₂ | H | CH(CH₃) | X/Y-23 | 5-Cyclopropyl |
| CH₂ | 3-F | CH(CH₃) | X/Y-23 | 5-CH₃ |
| CH₂ | H | CH(CH₃) | X/Y-23 | 5-CH(CH₃)₂ |
| CH(CH₃) | H | CH(CH₃) | X/Y-23 | 5-Cyclopropyl |
| CH₂ | H | CH₂CH₂ | X/Y-23 | 5-Cyclopropyl |
| CH₂CH₂CH₂ | H | CH₂ | X/Y-23 | 5-CH₃ |
| CH₂CH₂ | H | CH₂CH₂ | X/Y-23 | 5-CH(CH₃)₂ |
| CH₂CH₂ | H | CH₂CH₂ | X/Y-23 | 5-Cyclopropyl |
| CH₂ | H | CH₂ | X/Y-26 | 1-CH₃ |
| CH₂ | H | CH₂ | X/Y-26 | 1,5-(CH₃)₂ |
| CH₂ | H | CH₂ | X/Y-26 | 1-CH₃, 5-Cyclopropyl |
| CH(CH₃) | H | CH(CH₃) | X/Y-26 | 1-CH₃, 5-Cyclopropyl |
| CH(CH₃) | H | CH(CH₃) | X/Y-26 | 1,5-(CH₃)₂ |
| CH(CH₃) | 3-F | CH₂ | X/Y-26 | 1-CH₃, 5-Cyclopropyl |
| CH₂CH₂ | H | CH₂CH₂ | X/Y-26 | 1-CH₃, 5-Cyclopropyl |
| CH₂ | H | CH₂CH₂ | X/Y-26 | 1,5-(CH₃)₂ |
| CH₂ | H | CH₂ | X/Y-28 | 1-CH₃ |
| CH₂ | H | CH₂ | X/Y-28 | 1,5-(CH₃)₂ |
| CH₂ | H | CH₂ | X/Y-28 | 1-CH₃, 5-Cyclopropyl |
| CH(CH₃) | H | CH(CH₃) | X/Y-28 | 1-CH₃, 5-Cyclopropyl |
| CH(CH₃) | H | CH(CH₃) | X/Y-28 | 1,5-(CH₃)₂ |
| CH(CH₃) | 3-F | CH₂ | X/Y-28 | 1-CH₃, 5-Cyclopropyl |
| CH₂CH₂ | H | CH₂CH₂ | X/Y-28 | 1-CH₃, 5-Cyclopropyl |
| CH₂ | H | CH₂CH₂ | X/Y-28 | 1,5-(CH₃)₂ |
| CH₂ | H | CH₂ | X/Y-22 | — |
| CH₂ | H | CH₂ | X/Y-22 | 3-CH₃ |
| CH₂ | H | CH₂ | X/Y-22 | 3-Cyclopropyl |
| CH₂ | H | CH₂ | X/Y-22 | 3-OCH₃ |
| CH(CH₃) | H | CH₂ | X/Y-22 | 3-CH₃ |
| CH₂ | H | CH(CH₃) | X/Y-22 | 3-Cyclopropyl |
| CH₂ | 3-F | CH(CH₃) | X/Y-22 | 3-OCH₃ |
| CH₂CH₂ | H | CH₂CH₂ | X/Y-22 | 3-Cyclopropyl |
| CH₂ | H | CH₂CH₂ | X/Y-22 | 3-CH₃ |
| CH₂ | H | CH₂ | X/Y-29 | 1-CH₃ |
| CH₂ | H | CH₂ | X/Y-29 | 1,3-(CH₃)₂ |
| CH₂ | H | CH₂ | X/Y-29 | 1-CH₃, 3-Cyclopropyl |
| CH(CH₃) | H | CH(CH₃) | X/Y-29 | 1,3-(CH₃)₂ |
| CH(CH₃) | 3-F | CH(CH₃) | X/Y-29 | 1-CH₃, 3-Cyclopropyl |
| CH₂CH₂ | H | CH₂CH₂CH₂ | X/Y-29 | 1,3-(CH₃)₂ |
| CH₂CH₂ | H | CH₂CH₂ | X/Y-29 | 1-CH₃, 3-Cyclopropyl |
| CH₂ | H | CH₂ | X/Y-17 | — |
| CH₂ | H | CH₂ | X/Y-17 | 5-Cyclopropyl |
| CH₂ | H | CH₂ | X/Y-17 | 5-CH₃ |
| CH₂ | H | CH₂ | X/Y-17 | 5-OCH₂CH₃ |
| CH₂ | H | CH₂ | X/Y-17 | 5-Cl |
| CH₂ | H | CH₂ | X/Y-17 | 4-CH₃ |
| CH₂ | H | CH₂ | X/Y-17 | 4-Cyclopropyl |
| CH₂ | H | CH₂ | X/Y-17 | 4-OCH₂CH₃ |
| CH₂ | H | CH₂ | X/Y-17 | 4-Cl |
| CH(CH₃) | H | CH(CH₃) | X/Y-17 | 5-Cyclopropyl |
| CH(CH₃) | H | CH(CH₃) | X/Y-17 | 4-Cyclopropyl |
| CH(CH₃) | 3-F | CH(CH₃) | X/Y-17 | 5-OCH₂CH₃ |
| CH₂CH₂ | H | CH₂CH₂ | X/Y-17 | 5-Cyclopropyl |
| CH₂CH₂ | H | CH₂CH₂ | X/Y-17 | 4-Cyclopropyl |
| CH₂CH₂ | H | CH₂CH₂CH₂ | X/Y-17 | 5-CH₃ |
| CH₂ | H | CH₂ | X/Y-14 | — |
| CH₂ | H | CH₂ | X/Y-14 | 5-CH₃ |
| CH₂ | H | CH₂ | X/Y-14 | 5-Cyclopropyl |
| CH₂ | H | CH₂ | X/Y-14 | 4-CH₃ |
| CH₂ | H | CH₂ | X/Y-14 | 4-Cyclopropyl |
| CH₂ | H | CH₂ | X/Y-14 | 4-OCH₂CH₃ |
| CH₂ | H | CH₂ | X/Y-14 | 5-OCH₂CH₃ |
| CH₂ | H | CH₂ | X/Y-14 | 5-Cl |
| CH(CH₃) | H | CH(CH₃) | X/Y-14 | 4-Cyclopropyl |

TABLE A-continued
(for structure I.A)

| A | R¹ | B | Y | Substituent on Y |
|---|---|---|---|---|
| CH(CH₃) | H | CH(CH₃) | X/Y-14 | 5-Cyclopropyl |
| CH(CH₃) | H | CH(CH₃) | X/Y-14 | 4-CH₃ |
| CH(CH₃) | 3-F | CH(CH₃) | X/Y-14 | 4-Cyclopropyl |
| CH₂ | 3-F | CH₂ | X/Y-14 | 5-OCH₂CH₃ |
| CH₂CH₂ | H | CH₂CH₂ | X/Y-14 | 4-Cyclopropyl |
| CH₂CH₂ | H | CH₂CH₂ | X/Y-14 | 5-Cyclopropyl |
| CH₂CH₂ | H | CH₂CH₂CH₂ | X/Y-14 | 5-Cl |
| CH₂CH₂ | H | CH₂CH₂ | X/Y-14 | 4-CH₃ |
| CH₂ | H | CH₂ | X/Y-20 | 1-CH₃ |
| CH₂ | H | CH₂ | X/Y-20 | 1,5-(CH₃)₂ |
| CH(CH₃) | H | CH(CH₃) | X/Y-20 | 1-CH₃ |
| CH(CH₃) | 3-F | CH(CH₃) | X/Y-20 | 1,5-(CH₃)₂ |
| CH₂CH₂ | H | CH₂CH₂ | X/Y-20 | 1-CH₃ |
| CH₂CH₂ | H | CH₂CH₂ | X/Y-20 | 1,5-(CH₃)₂ |
| CH(CH₃)CH₂ | 3-F | CH(CH₃)CH₂ | X/Y-20 | 1,5-(CH₃)₂ |
| CH₂ | H | CH₂ | X/Y-3 | — |
| CH₂ | H | CH₂ | X/Y-3 | 3-CH₃ |
| CH₂ | H | CH₂ | X/Y-3 | 3-CH₂CH₃ |
| CH₂ | H | CH₂ | X/Y-3 | 3-CH(CH₃)₂ |
| CH₂ | H | CH₂ | X/Y-3 | 3-Cyclopropyl |
| CH₂ | H | CH₂ | X/Y-3 | 3-OCHICH₃ |
| CH₂ | H | CH₂ | X/Y-3 | 3-CH₂OCH₃ |
| CH₂ | H | C'2 | X/Y-3 | 3-CF3 |
| CH(CH₃) | H | CH₂ | X/Y-3 | 3-CH₃ |
| CH(CH₃) | H | CH₂ | X/Y-3 | 3-CH(CH₃)₂ |
| CH(CH₃) | H | CH₂ | X/Y-3 | 3-Cyclopropyl |
| CH₂ | H | CH(CH₃) | X/Y-3 | 3-CH₃ |
| CH₂ | H | CH(CH₃) | X/Y-3 | 3-CH(CH₃)₂ |
| CH₂ | H | CH(CH₃) | X/Y-3 | 3-Cyclopropyl |
| CH(CH₃) | H | CH(CH₃) | X/Y-3 | 3-CH₃ |
| CH(CH₃) | 3-F | CH(CH₃) | X/Y-3 | 3-CH(CH₃)₂ |
| CH(CH₃) | H | CH(CH₃) | X/Y-3 | 3-Cyclopropyl |
| CH₂ | H | CH₂CH₂ | X/Y-3 | 3-CH₃ |
| CH₂CH₂ | H | CH₂CH₂CH₂ | X/Y-3 | 3-CH(CH₃)₂ |
| CH₂ | H | CH₂CH₂ | X/Y-3 | 3-Cyclopropyl |
| CH₂CH₂ | H | CH₂CH(CH₃) | X/Y-3 | 3-Cyclopropyl |
| CH₂CH₂ | H | CH₂CH(CH₃) | X/Y-3 | 3-CH(CH₃)₂ |
| CH₂CH₂CH₂ | 3-F | CH(CH₃)CH₂ | X/Y-3 | 3-CH₃ |
| CH₂ | H | CH₂ | X/Y-5 | — |
| CH₂ | H | CH₂ | X/Y-5 | 5-OCH₂CH₃ |
| CH₂ | H | CH₂ | X/Y-5 | 5-Cyclopropyl |
| CH₂ | H | CH₂ | X/Y-5 | 5-CH₃ |
| CH(CH₃) | 3-F | CH(CH₃) | X/Y-5 | 5-CH₃ |
| CH₂ | H | CH(CH₃) | X/Y-5 | 5-Cyclopropyl |
| CH(CH₃) | H | CH₂ | X/Y-5 | 5-Cyclopropyl |
| CH₂ | H | CH₂CH₂ | X/Y-5 | 5-OCH₂CH₃ |
| CH₂CH₂ | H | CH₂CH₂CH₂ | X/Y-5 | 5-CH₃ |
| CH₂ | H | CH₂ | X/Y-4 | — |
| CH₂ | H | CH₂ | X/Y-4 | 3-OCH₂CH₃ |
| CH₂ | H | CH₂ | X/Y-4 | 5-OCH₂CH₃ |
| CH₂ | H | CH₂ | X/Y-4 | 3-CH(CH₃)₂ |
| CH₂ | H | CH₂ | X/Y-4 | 5-CH₃ |
| CH(CH₃) | H | CH(CH₃) | X/Y-4 | 3-CH(CH₃)₂ |
| CH₂ | H | CH₂ | X/Y-11 | — |
| CH₂ | H | CH₂ | X/Y-11 | 3-CH₃ |
| CH₂ | H | CH₂ | X/Y-11 | 5-CH₃ |
| CH₂ | H | CH(CH₃) | X/Y-11 | 3-CH₃ |
| CH₂ | 3-F | CH(CH₃) | X/Y-11 | 5-CH₃ |
| CH(CH₃) | H | CH(CH₃) | X/Y-11 | 5-CH₃ |
| CH₂ | H | CH₂ | X/Y-21 | — |
| CH₂ | H | CH₂ | X/Y-21 | 4-5-Cl₂ |
| CH₂ | H | CH₂ | X/Y-21 | 4,5-(CH₃)₂ |
| CH₂ | H | CH₂ | X/Y-21 | 4,5-Br₂ |
| CH(CH₃) | H | CH(CH₃) | X/Y-21 | 4,5-Cl₂ |
| CH(CH₃) | H | CH(CH₃) | X/Y-21 | 4,5-(CH₃)₂ |
| CH(CH₃) | H | CH(CH₃) | X/Y-21 | 4,5-Br₂ |
| CH₂ | H | CH₂ | X/Y-30 | — |
| CH₂ | H | CH₂ | X/Y-30 | 3,5-(CH₃)₂ |
| CH(CH₃) | H | CH(CH₃) | X/Y-30 | — |
| CH(CH₃) | H | CH(CH₃) | X/Y-30 | 3,5-(CH₃)₂ |
| CH₂ | H | CH₂ | X/Y-27 | — |
| CH₂ | H | CH₂ | X/Y-27 | 2-Cl |
| CH₂ | H | CH₂ | X/Y-27 | 2,5-(CH₃)₂ |
| CH(CH₃) | H | CH(CH₃) | X/Y-27 | 2-Cl |
| CH(CH₃) | H | CH(CH₃) | X/Y-27 | 2,5-(CH₃)₂ |

TABLE B
(for structure I.B)

| A | R¹ | B | Y | Substituent on Y |
|---|---|---|---|---|
| CH₂ | H | CH₂ | X/Y-1 | |
| CH(CH₃) | H | CH₂ | X/Y-1 | |
| CH(CH₂CH₃) | H | CH₂ | X/Y-1 | |
| CH₂ | H | CH(CH₃) | X/Y-1 | |
| CH₂ | H | CH(CH₂CH₃) | X/Y-1 | |
| CH₂ | 3-CH₃ | CH₂ | X/Y-1 | |
| CH₂ | 3-F | CH₂ | X/Y-1 | |
| CH₂ | H | CH₂ | X/Y-1 | 5-CH₃ |
| CH₂ | H | CH₂ | X/Y-1 | 4-CH₃ |
| CH₂ | H | CH₂ | X/Y-1 | 3-CH₃ |
| CH₂ | H | CH₂ | X/Y-1 | 5-Cyclopropyl |
| CH₂ | H | CH₂ | X/Y-1 | 4-Cyclopropyl |
| CH₂ | H | CH₂ | X/Y-1 | 3-Cyclopropyl |
| CH₂ | H | CH₂ | X/Y-1 | 5-Cl |
| CH₂ | H | CH₂ | X/Y-1 | 5-Br |
| CH₂ | H | CH₂ | X/Y-1 | 4-Cl |
| CH₂ | H | CH₂ | X/Y-1 | 4-Br |
| CH₂ | H | CH₂ | X/Y-1 | 4,5-Cl,Cl |
| CH₂ | H | CH₂ | X/Y-1 | 4-OCH₂CH₃ |
| CH(CH₃) | H | CH₂ | X/Y-1 | 5-Br |
| CH(CH₃) | H | CH₂ | X/Y-1 | 4,5-Cl,Cl |
| CH(CH₃) | H | CH₂ | X/Y-1 | 4-Cl |
| CH₂ | H | CH(CH₃) | X/Y-1 | 5-Br |
| CH₂ | H | CH(CH₃) | X/Y-1 | 4,5-Cl,Cl |
| CH(CH₃) | H | CH(CH₃) | X/Y-1 | — |
| CH(CH₃) | H | CH(CH₃) | X/Y-1 | 4,5-Cl,Cl |
| CH(CH₃) | 3-F | CH(CH₃) | X/Y-1 | — |
| CH(CH₃) | 3-F | CH(CH₃) | X/Y-1 | 5-Br |
| CH₂CH₂ | H | CH₂ | X/Y-1 | 5-Br |
| CH₂ | H | CH₂CH₂ | X/Y-1 | 4,5-Cl,Cl |
| CH₂CH₂CH₂ | H | CH₂ | X/Y-1 | 5-Br |
| CH₂CH₂ | H | CH₂CH₂CH₂ | X/Y-1 | 4,5-Cl,Cl |
| CH₂CH(CH₃) | H | CH₂CH₂ | X/Y-1 | 4,5-Cl,Cl |
| CH₂CH₂ | 3-F | CH₂CH(CH₃) | X/Y-1 | 5-Br |
| CH₂ | H | CH₂ | X/Y-2 | — |
| CH₂ | H | CH₂ | X/Y-2 | 4-Cyclopropyl |
| CH₂ | H | CH₂ | X/Y-2 | 5-Cyclopropyl |
| CH₂ | H | CH₂ | X/Y-2 | 5-Cl |
| CH₂ | H | CH₂ | X/Y-2 | 4,5-Cl,Cl |
| CH₂ | H | CH₂ | X/Y-2 | 4,5-Br,Br |
| CH₂ | H | CH₂ | X/Y-2 | 4-CH₃ |
| CH₂ | H | CH₂ | X/Y-2 | 5-CH₃ |
| CH₂ | H | CH₂ | X/Y-2 | 4-OCH₃ |
| CH₂ | H | CH₂ | X/Y-2 | 5-OCH₃ |
| CH(CH₃) | H | CH₂ | X/Y-2 | 4,5-Cl,Cl |
| CH(CH₃) | H | CH₂ | X/Y-2 | 4,5-Br,Br |
| CH₂ | H | CH(CH₃) | X/Y-2 | 4,5-Cl,Cl |
| CH₂ | H | CH(CH₃) | X/Y-2 | 4,5-Br,Br |
| CH(CH₃) | H | CH(CH₃) | X/Y-2 | 4,5-Cl,Cl |
| CH(CH₃) | H | CH(CH₃) | X/Y-2 | 4,5-Br,Br |
| CH(CH₃) | 3-F | CH(CH₃) | X/Y-2 | 4,5-Cl,Cl |
| CH(CH₃) | 3-F | CH(CH₃) | X/Y-2 | 4,5-Br,Br |
| CH₂CH₂ | H | CH₂ | X/Y-2 | 4,5-Cl,Cl |
| CH₂CH₂ | H | CH₂CH₂ | X/Y-2 | 4,5-Br,Br |
| CH₂CH₂CH₂ | H | CH₂ | X/Y-2 | 4,5-Cl,Cl |
| CH₂CH₂CH₂ | H | CH₂CH₂CH₂ | X/Y-2 | 4,5-Br,Br |
| CH₂CH(CH₃) | H | CH₂CH₂ | X/Y-2 | 4,5-Br,Br |
| CH₂CH₂ | 3-F | CH₂CH(CH₃) | X/Y-2 | 4,5-Cl,Cl |
| CH₂ | H | CH₂ | X/Y-15 | — |
| CH₂ | H | CH₂ | X/Y-15 | 2-CH₃ |
| CH₂ | H | CH₂ | X/Y-15 | 2-Cyclopropyl |
| CH₂ | H | CH₂ | X/Y-15 | 2-OCH₂CH₃ |
| CH₂ | H | CH₂ | X/Y-15 | 2-Cl |
| CH(CH₃) | H | CH₂ | X/Y-15 | 2-Cyclopropyl |
| CH(CH₃) | H | CH₂ | X/Y-15 | 2-OCH₂CH₃ |
| CH₂ | H | CH(CH₃) | X/Y-15 | 2-Cyclopropyl |
| CH₂ | H | CH(CH₃) | X/Y-15 | 2-OCH₂CH₃ |
| CH(CH₃) | H | CH(CH₃) | X/Y-15 | 2-Cyclopropyl |
| CH(CH₃) | H | CH(CH₃) | X/Y-15 | 2-OCH₂CH₃ |
| CH(CH₃) | 3-F | CH(CH₃) | X/Y-15 | 2-Cyclopropyl |
| CH(CH₃) | 3-F | CH(CH₃) | X/Y-15 | 2-OCH₂CH₃ |
| CH₂CH₂ | H | CH₂ | X/Y-15 | 2-Cyclopropyl |
| CH₂CH₂ | H | CH₂CH₂ | X/Y-15 | 2-OCH₂CH₃ |
| CH₂CH₂CH₂ | H | CH₂ | X/Y-15 | 2-Cyclopropyl |
| CH₂CH₂ | H | CH₂CH₂CH₂ | X/Y-15 | 2-OCH₂CH₃ |
| CH₂CH(CH₃) | H | CH₂CH₂ | X/Y-15 | 2-Cyclopropyl |
| CH₂CH₂ | 3-F | CH₂CH(CH₃) | X/Y-15 | 2-OCH₂CH₃ |
| CH₂ | H | CH₂ | X/Y-12 | — |

TABLE B-continued (for structure I.B)

| A | R$^1$ | B | Y | Substituent on Y |
|---|---|---|---|---|
| CH$_2$ | H | CH$_2$ | X/Y-12 | 2-CH$_3$ |
| CH$_2$ | H | CH$_2$ | X/Y-12 | 2-Cyclopropyl |
| CH$_2$ | H | CH$_2$ | X/Y-12 | 2-OCH$_2$CH$_3$ |
| CH(CH$_3$) | H | CH$_2$ | X/Y-12 | 2-Cyclopropyl |
| CH(CH$_3$) | H | CH$_2$ | X/Y-12 | 2-OCH$_2$CH$_3$ |
| CH$_2$ | H | CH(CH$_3$) | X/Y-12 | 2-Cyclopropyl |
| CH$_2$ | H | CH(CH$_3$) | X/Y-12 | 2-OCH$_2$CH$_3$ |
| CH(CH$_3$) | H | CH(CH$_3$) | X/Y-12 | 2-Cyclopropyl |
| CH(CH$_3$) | 3-F | CH(CH$_3$) | X/Y-12 | 2-OCH$_2$CH$_3$ |
| CH$_2$CH$_2$ | H | CH$_2$ | X/Y-12 | 2-Cyclopropyl |
| CH$_2$CH$_2$ | H | CH$_2$CH$_2$ | X/Y-12 | 2-OCH$_2$CH$_3$ |
| CH$_2$CH$_2$CH$_2$ | H | CH$_2$ | X/Y-12 | 2-Cyclopropyl |
| CH$_2$CH$_2$ | H | CH$_2$CH$_2$CH$_2$ | X/Y-12 | 2-OCH$_2$CH$_3$ |
| CH$_2$CH(CH$_3$) | H | CH$_2$CH$_2$ | X/Y-12 | 2-Cyclopropyl |
| CH$_2$CH$_2$ | 3-F | CH$_2$CH(CH$_3$) | X/Y-12 | 2-Cyclopropyl |
| CH$_2$ | H | CH$_2$ | X/Y-18 | 1-CH$_3$ |
| CH$_2$ | H | CH$_2$ | X/Y-18 | 1,2-(CH$_3$)$_2$ |
| CH$_2$ | H | CH$_2$ | X/Y-18 | 1,4-(CH$_3$)$_2$ |
| CH$_2$ | H | CH$_2$ | X/Y-18 | 1,2,4-(CH$_3$)$_2$ |
| CH$_2$ | H | CH$_2$ | X/Y-18 | 1-CH$_3$, 2-Cyclopropyl |
| CH(CH$_3$) | H | CH$_2$ | X/Y-18 | 1-CH$_3$, 2-Cyclopropyl |
| CH(CH$_3$) | H | CH$_2$ | X/Y-18 | 1,2,4-(CH$_3$)$_3$ |
| CH$_2$ | H | CH(CH$_3$) | X/Y-18 | 1-CH$_3$, 2-Cyclopropyl |
| CH$_2$ | H | CH(CH$_3$) | X/Y-18 | 1,2,4-(CH$_3$)$_3$ |
| CH(CH$_3$) | H | CH(CH$_3$) | X/Y-18 | 1-CH$_3$, 2-Cyclopropyl |
| CH(CH$_3$) | H | CH(CH$_3$) | X/Y-18 | 1,2,4-(CH$_3$)$_3$ |
| CH(CH$_3$) | 3-F | CH(CH$_3$) | X/Y-18 | 1,2,4-(CH$_3$)$_3$ |
| CH$_2$CH$_2$ | H | CH$_2$ | X/Y-18 | 1-CH$_3$, 2-Cyclopropyl |
| CH$_2$CH$_2$ | H | CH$_2$CH$_2$ | X/Y-18 | 1,2,4-(CH$_3$)$_2$ |
| CH$_2$CH$_2$CH$_2$ | H | CH$_2$ | X/Y-18 | 1-CH$_3$, 2-Cyclopropyl |
| CH$_2$CH$_2$ | H | CH$_2$CH$_2$CH$_2$ | X/Y-18 | 1,2,4-(CH$_3$)$_2$ |
| CH$_2$CH(CH$_3$) | H | CH$_2$CH$_2$ | X/Y-18 | 1-CH$_3$, 2-Cyclopropyl |
| CH$_2$CH$_2$ | 3-F | CH$_2$CH(CH$_3$) | X/Y-18 | 1,2,4-(CH$_3$)$_2$ |
| CH$_2$ | H | CH$_2$ | X/Y-19 | 1-CH$_3$ |
| CH$_2$ | H | CH$_2$ | X/Y-19 | 1,2-(CH$_3$)$_2$ |
| CH$_2$ | H | CH$_2$ | X/Y-19 | 1,5-(CH$_3$)$_2$ |
| CH$_2$ | H | CH$_2$ | X/Y-19 | 1-CH$_3$, 2-Cyclopropyl |
| CH(CH$_3$) | H | CH$_2$ | X/Y-19 | 1,2-(CH$_3$)$_2$ |
| CH(CH$_3$) | H | CH$_2$ | X/Y-19 | 1-CH$_3$, 2-Cyclopropyl |
| CH$_2$ | H | CH(CH$_3$) | X/Y-19 | 1,2-(CH$_3$)$_2$ |
| CH$_2$ | H | CH(CH$_3$) | X/Y-19 | 1-CH$_3$, 2-Cyclopropyl |
| CH(CH$_3$) | H | CH(CH$_3$) | X/Y-19 | 1,2-(CH$_3$)$_2$ |
| CH(CH$_3$) | H | CH(CH$_3$) | X/Y-19 | 1-CH$_3$, 2-Cyclopropyl |
| CH(CH$_3$) | 3-F | CH$_2$ | X/Y-19 | 1-CH$_3$, 2-Cyclopropyl |
| CH$_2$CH$_2$ | H | CH$_2$ | X/Y-19 | 1-CH$_3$, 2-Cyclopropyl |
| CH$_2$CH$_2$ | H | CH$_2$CH$_2$ | X/Y-19 | 1,2-(CH$_3$)$_2$ |
| CH$_2$CH$_2$CH$_2$ | H | CH$_2$ | X/Y-19 | 1-CH$_3$, 2-Cyclopropyl |
| CH$_2$CH$_2$ | H | CH$_2$CH$_2$CH$_2$ | X/Y-19 | 1,2-(CH$_3$)$_2$ |
| CH$_2$CH(CH$_3$) | H | CH$_2$CH$_2$ | X/Y-19 | 1-CH$_3$, 2-Cyclopropyl |
| CH$_2$CH$_2$ | 3-F | CH$_2$CH(CH$_3$) | X/Y-19 | 1,2-(CH$_3$)$_2$ |
| CH$_2$ | H | CH$_2$ | X/Y-16 | — |
| CH$_2$ | H | CH$_2$ | X/Y-16 | 2-CH$_3$ |
| CH$_2$ | H | CH$_2$ | X/Y-16 | 2-Cyclopropyl |
| CH$_2$ | H | CH$_2$ | X/Y-16 | 2-Cl |
| CH$_2$ | H | CH$_2$ | X/Y-16 | 2-OCH$_2$CH$_3$ |
| CH(CH$_3$) | H | CH$_2$ | X/Y-16 | 2-CH$_3$ |
| CH(CH$_3$) | H | CH$_2$ | X/Y-16 | 2-Cyclopropyl |
| CH$_2$ | H | CH(CH$_3$) | X/Y-16 | 2-CH$_3$ |
| CH$_2$ | H | CH(CH$_3$) | X/Y-16 | 2-Cyclopropyl |
| CH$_2$(CH$_3$) | H | CH(CH$_3$) | X/Y-16 | 2-CH$_3$ |
| CH$_2$(CH$_3$) | H | CH(CH$_3$) | X/Y-16 | 2-Cyclopropyl |
| CH$_2$(CH$_3$) | 3-F | CH(CH$_3$) | X/Y-16 | 2-Cyclopropyl |
| CH$_2$CH$_2$ | H | CH$_2$ | X/Y-16 | 2-Cyclopropyl |
| CH$_2$CH$_2$ | H | CH$_2$CH$_2$ | X/Y-16 | 2-CH$_3$ |
| CH$_2$CH$_2$CH$_2$ | H | CH$_2$ | X/Y-16 | 2-Cyclopropyl |
| CH$_2$CH$_2$ | H | CH$_2$CH$_2$CH$_2$ | X/Y-16 | 2-CH$_3$ |
| CH$_2$CH(CH$_3$) | H | CH$_2$CH$_2$ | X/Y-16 | 2-Cyclopropyl |
| CH$_2$CH$_2$ | 3-F | CH$_2$CH(CH$_3$) | X/Y-16 | 2-CH$_3$ |
| CH$_2$ | H | CH$_2$ | X/Y-13 | — |
| CH$_2$ | H | CH$_2$ | X/Y-13 | 2-CH$_3$ |
| CH$_2$ | H | CH$_2$ | X/Y-13 | 2-Cyclopropyl |
| CH$_2$ | H | CH$_2$ | X/Y-13 | 2-OCH$_2$CH$_3$ |
| CH(CH$_3$) | H | CH$_2$ | X/Y-13 | 2-OCH$_2$CH$_3$ |
| CH(CH$_3$) | H | CH$_2$ | X/Y-13 | 2-Cyclopropyl |
| CH$_2$ | H | CH(CH$_3$) | X/Y-13 | 2-OCH$_2$CH$_3$ |
| CH$_2$ | H | CH(CH$_3$) | X/Y-13 | 2-Cyclopropyl |
| CH(CH$_3$) | H | CH(CH$_3$) | X/Y-13 | 2-OCH$_2$CH$_3$ |
| CH(CH$_3$) | 3-F | CH(CH$_3$) | X/Y-13 | 2-Cyclopropyl |
| CH$_2$CH$_2$ | H | CH$_2$ | X/Y-13 | 2-Cyclopropyl |
| CH$_2$CH$_2$ | H | CH$_2$CH$_2$ | X/Y-13 | 2-CH$_3$ |
| CH$_2$CH$_2$CH$_2$ | H | CH$_2$ | X/Y-13 | 2-Cyclopropyl |
| CH$_2$CH$_2$ | H | CH$_2$CH$_2$CH$_2$ | X/Y-13 | 2-CH$_3$ |
| CH(CH$_3$)CH$_2$ | 3-F | CH$_2$CH$_2$ | X/Y-13 | 2-Cyclopropyl |
| CH$_2$CH$_2$ | H | CH(CH$_3$)CH$_2$ | X/Y-13 | 2-CH$_3$ |
| CH$_2$ | H | CH$_2$ | X/Y-6 | — |
| CH$_2$ | H | CH$_2$ | X/Y-6 | 3-CH$_3$ |
| CH$_2$ | H | CH$_2$ | X/Y-6 | 3-Cyclopropyl |
| CH$_2$ | H | CH$_2$ | X/Y-6 | 3-OCH$_2$CH$_3$ |
| CH(CH$_3$) | H | CH(CH$_3$) | X/Y-6 | 3-Cyclopropyl |
| CH(CH$_3$) | 3-F | CH(CH$_3$) | X/Y-6 | 3-Cyclopropyl |
| CH$_2$CH$_2$ | H | CH$_2$CH$_2$ | X/Y-6 | 3-Cyclopropyl |
| CH$_2$CH$_2$ | H | CH$_2$CH$_2$CH$_2$ | X/Y-6 | 3-CH$_3$ |
| CH(CH$_3$)CH$_2$ | 3-F | CH$_2$CH$_2$ | X/Y-6 | 3-Cyclopropyl |
| CH$_2$CH$_2$ | H | CH(CH$_3$)CH$_2$ | X/Y-6 | 3-Cyclopropyl |
| CH$_2$ | H | CH$_2$ | X/Y-8 | 1-CH$_3$ |
| CH$_2$ | H | CH$_2$ | X/Y-8 | 1,3-(CH$_3$)$_2$ |
| CH$_2$ | H | CH$_2$ | X/Y-8 | 1,4-(CH$_3$)$_2$ |
| CH$_2$ | H | CH$_2$ | X/Y-8 | 1-CH$_3$, 3-Cyclopropyl |
| CH(CH$_3$) | H | CH(CH$_3$) | X/Y-8 | 1-CH$_3$, 3-Cyclopropyl |
| CH(CH$_3$) | 3-F | CH(CH$_3$) | X/Y-8 | 1-CH$_3$, 3-Cyclopropyl |
| CH$_2$CH$_2$ | H | CH$_2$CH$_2$ | X/Y-8 | 1-CH$_3$, 3-Cyclopropyl |
| CH$_2$CH$_2$ | H | CH$_2$CH$_2$CH$_2$ | X/Y-8 | 1,3-(CH$_3$)$_2$ |
| CH$_2$CH(CH$_3$) | H | CH$_2$CH$_2$ | X/Y-8 | 1-CH$_3$, 3-Cyclopropyl |
| CH(CH$_3$)CH$_2$ | 3-F | CH$_2$CH$_2$ | X/Y-8 | 1-CH$_3$, 3-Cyclopropyl |
| CH$_2$ | H | CH$_2$ | X/Y-10 | 1-CH$_3$ |
| CH$_2$ | H | CH$_2$ | X/Y-10 | 1,4-(CH$_3$)$_2$ |
| CH$_2$ | H | CH$_2$ | X/Y-10 | 1-CH$_3$, 4-OCH$_3$ |
| CH$_2$ | H | CH$_2$ | X/Y-10 | 1-CH$_3$, 5-CH(CH$_3$)$_2$ |
| CH$_2$ | H | CH$_2$ | X/Y-10 | 1-CH$_3$, 5-Cyclopropyl |
| CH(CH$_3$) | H | CH(CH$_3$) | X/Y-10 | 1-CH$_3$, 5-Cyclopropyl |
| CH(CH$_3$) | 3-F | CH(CH$_3$) | X/Y-10 | 1,4-(CH$_3$)$_2$ |
| CH$_2$CH$_2$ | H | CH$_2$CH$_2$ | X/Y-10 | 1-CH$_3$, 5-Cyclopropyl |
| CH$_2$CH$_2$ | H | CH$_2$CH$_2$CH$_2$ | X/Y-10 | 1,5-(CH$_3$)$_2$ |
| CH$_2$CH(CH$_3$) | H | CH$_2$CH$_2$ | X/Y-10 | 1-CH$_3$, 5-Cyclopropyl |
| CH(CH$_3$)CH$_2$ | 3-F | CH$_2$CH$_2$ | X/Y-10 | 1-CH$_3$, 5-Cyclopropyl |
| CH$_2$ | H | CH$_2$ | X/Y-7 | — |
| CH$_2$ | H | CH$_2$ | X/Y-7 | 3-CH$_3$ |
| CH(CH$_3$) | H | CH(CH$_3$) | X/Y-7 | 3-CH$_3$ |
| CH(CH$_3$) | 3-F | CH(CH$_3$) | X/Y-7 | 3-CH$_3$ |
| CH$_2$CH$_2$ | H | CH$_2$CH$_2$ | X/Y-7 | 3-CH$_3$ |
| CH$_2$CH$_2$ | 3-F | CH(CH$_3$)CH$_2$CH$_2$ | X/Y-7 | 3-CH$_3$ |
| CH$_2$ | H | CH$_2$ | X/Y-9 | 1-CH$_3$ |
| CH$_2$ | H | CH$_2$ | X/Y-9 | 1,3-(CH$_3$)$_2$ |
| CH$_2$ | H | CH$_2$ | X/Y-9 | 1,5-(CH$_3$)$_2$ |
| CH(CH$_3$) | H | CH(CH$_3$) | X/Y-9 | 1,3-(CH$_3$)$_2$ |
| CH(CH$_3$) | 3-F | CH(CH$_3$) | X/Y-9 | 1,5-(CH$_3$)$_2$ |
| CH$_2$CH$_2$ | H | CH$_2$CH$_2$ | X/Y-9 | 1,3-(CH$_3$)$_2$ |
| CH$_2$CH$_2$ | H | CH$_2$CH$_2$CH$_2$ | X/Y-9 | 1,5-(CH$_3$)$_2$ |

TABLE B-continued (for structure I.B)

| A | R¹ | B | Y | Substituent on Y |
|---|----|---|---|------------------|
| CH₂CH(CH₃) | H | CH₂CH₂ | X/Y-9 | 1,3-(CH₃)₂ |
| CH(CH₃)CH₂ | 3-F | CH₂CH₂ | X/Y-9 | 1,5-(CH₃)₂ |
| CH₂ | H | CH₂ | X/Y-25 | 5-Cyclopropyl |
| CH₂ | H | CH₂ | X/Y-25 | 5-CH₃ |
| CH₂ | H | CH₂ | X/Y-25 | 5-CH₂CH₃ |
| CH₂ | H | CH₂ | X/Y-25 | 5-CH(CH₃)₂ |
| CH₂ | H | CH₂ | X/Y-25 | 5-OCH₃ |
| CH(CH₃) | H | CH(CH₃) | X/Y-25 | 5-Cyclopropyl |
| CH₂(CH₃) | H | CH(CH₃) | X/Y-25 | 5-CH₃ |
| CH(CH₃) | H | CH(CH₃) | X/Y-25 | 5-OCH₂CH₃ |
| CH(CH₃) | 3-F | CH(CH₃) | X/Y-25 | 5-Cyclopropyl |
| CH₂CH₂ | H | CH₂ | X/Y-25 | 5-Cyclopropyl |
| CH₂CH₂ | H | CH₂CH₂ | X/Y-25 | 5-CH₃ |
| CH₂CH₂CH₂ | H | CH₂ | X/Y-25 | 5-OCH₂CH₃ |
| CH₂CH₂ | 3-F | CH₂CH(CH₃) | X/Y-25 | 5-Cyclopropyl |
| CH₂ | H | CH(CH₃) | X/Y-25 | 5-Cyclopropyl |
| CH₂ | H | CH₂ | X/Y-23 | — |
| CH₂ | H | CH₂ | X/Y-23 | 5-Cyclopropyl |
| CH₂ | H | CH₂ | X/Y-23 | 5-CH₃ |
| CH₂ | H | CH₂ | X/Y-23 | 5-CH(CH₃)₂ |
| CH₂ | H | CH₂ | X/Y-23 | 5-Cl |
| CH₂ | H | CH₂ | X/Y-23 | 5-OCH₂CH₃ |
| CH₂ | H | CH(CH₃) | X/Y-23 | 5-Cyclopropyl |
| CH₂ | 3-F | CH(CH₃) | X/Y-23 | 5-CH₃ |
| CH₂ | H | CH(CH₃) | X/Y-23 | 5-CH(CH₃)₂ |
| CH(CH₃) | H | CH(CH₃) | X/Y-23 | 5-Cyclopropyl |
| CH₂ | H | CH₂CH₂ | X/Y-23 | 5-Cyclopropyl |
| CH₂CH₂CH₂ | H | CH₂ | X/Y-23 | 5-CH₃ |
| CH₂CH₂ | H | CH₂CH₂ | X/Y-23 | 5-CH(CH₃)₂ |
| CH₂CH₂ | H | CH₂CH₂ | X/Y-23 | 5-Cyclopropyl |
| CH₂ | H | CH₂ | X/Y-26 | 1-CH₃ |
| CH₂ | H | CH₂ | X/Y-26 | 1,5-(CH₃)₂ |
| CH₂ | H | CH₂ | X/Y-26 | 1-CH₃, 5-Cyclopropyl |
| CH(CH₃) | H | CH(CH₃) | X/Y-26 | 1-CH₃, 5-Cyclopropyl |
| CH(CH₃) | H | CH(CH₃) | X/Y-26 | 1,5-(CH₃)₂ |
| CH(CH₃) | 3-F | CH₂ | X/Y-26 | 1-CH₃, 5-Cyclopropyl |
| CH₂CH₂ | H | CH₂CH₂ | X/Y-26 | 1-CH₃, 5-Cyclopropyl |
| CH₂ | H | CH₂CH₂ | X/Y-26 | 1,5-(CH₃)₂ |
| CH₂ | H | CH₂ | X/Y-28 | 1-CH₃ |
| CH₂ | H | CH₂ | X/Y-28 | 1,5-(CH₃)₂ |
| CH₂ | H | CH₂ | X/Y-28 | 1-CH₃, 5-Cyclopropyl |
| CH(CH₃) | H | CH(CH₃) | X/Y-28 | 1-CH₃, 5-Cyclopropyl |
| CH(CH₃) | H | CH(CH₃) | X/Y-28 | 1,5-(CH₃)₂ |
| CH(CH₃) | 3-F | CH₂ | X/Y-28 | 1-CH₃, 5-Cyclopropyl |
| CH₂CH₂ | H | CH₂CH₂ | X/Y-28 | 1-CH₃, 5-Cyclopropyl |
| CH₂ | H | CH₂CH₂ | X/Y-28 | 1,5-(CH₃)₂ |
| CH₂ | H | CH₂ | X/Y-22 | — |
| CH₂ | H | CH₂ | X/Y-22 | 3-CH₃ |
| CH₂ | H | CH₂ | X/Y-22 | 3-Cyclopropyl |
| CH₂ | H | CH₂ | X/Y-22 | 3-OCH₃ |
| CH(CH₃) | H | CH₂ | X/Y-22 | 3-CH₃ |
| CH₂ | H | CH(CH₃) | X/Y-22 | 3-Cyclopropyl |
| CH₂ | 3-F | CH(CH₃) | X/Y-22 | 3-OCH₃ |
| CH₂CH₂ | H | CH₂CH₂ | X/Y-22 | 3-Cyclopropyl |
| CH₂ | H | CH₂CH₂ | X/Y-22 | 3-CH₃ |
| CH₂ | H | CH₂ | X/Y-29 | 1-CH₃ |
| CH₂ | H | CH₂ | X/Y-29 | 1,3-(CH₃)₂ |
| CH₂ | H | CH₂ | X/Y-29 | 1-CH₃, 3-Cyclopropyl |
| CH(CH₃) | H | CH(CH₃) | X/Y-29 | 1,3-(CH₃)₂ |
| CH(CH₃) | 3-F | CH(CH₃) | X/Y-29 | 1-CH₃, 3-Cyclopropyl |
| CH₂CH₂ | H | CH₂CH₂CH₂ | X/Y-29 | 1,3-(CH₃)₂ |
| CH₂CH₂ | H | CH₂CH₂ | X/Y-29 | 1-CH₃, 3-Cyclopropyl |
| CH₂ | H | CH₂ | X/Y-17 | — |
| CH₂ | H | CH₂ | X/Y-17 | 5-Cyclopropyl |
| CH₂ | H | CH₂ | X/Y-17 | 5-CH₃ |
| CH₂ | H | CH₂ | X/Y-17 | 5-OCH₂CH₃ |
| CH₂ | H | CH₂ | X/Y-17 | 5-Cl |
| CH₂ | H | CH₂ | X/Y-17 | 4-CH₃ |
| CH₂ | H | CH₂ | X/Y-17 | 4-Cyclopropyl |
| CH₂ | H | CH₂ | X/Y-17 | 4-OCH₂CH₃ |
| CH₂ | H | CH₂ | X/Y-17 | 4-Cl |
| CH(CH₃) | H | CH(CH₃) | X/Y-17 | 5-Cyclopropyl |
| CH(CH₃) | H | CH(CH₃) | X/Y-17 | 4-Cyclopropyl |
| CH(CH₃) | 3-F | CH(CH₃) | X/Y-17 | 5-OCH₂CH₃ |
| CH₂CH₂ | H- | CH₂CH₂ | X/Y-17 | 5-Cyclopropyl |
| CH₂CH₂ | H | CH₂CH₂ | X/Y-17 | 4-Cyclopropyl |
| CH₂CH₂ | H | CH₂CH₂CH₂ | X/Y-17 | 5-CH₃ |
| CH₂ | H | CH₂ | X/Y-14 | — |
| CH₂ | H | CH₂ | X/Y-14 | 5-CH₃ |
| CH₂ | H | CH₂ | X/Y-14 | 4-CH₃ |
| CH₂ | H | CH₂ | X/Y-14 | 4-Cyclopropyl |
| CH₂ | H | CH₂ | X/Y-14 | 4-OCH₂CH₃ |
| CH₂ | H | CH₂ | X/Y-14 | 5-OCH₂CH₃ |
| CH₂ | H | CH₂ | X/Y-14 | 5-Cl |
| CH(CH₃) | H | CH(CH₃) | X/Y-14 | 4-Cyclopropyl |
| CH(CH₃) | H | CH(CH₃) | X/Y-14 | 5-Cyclopropyl |
| CH(CH₃) | H | CH(CH₃) | X/Y-14 | 4-CH₃ |
| CH(CH₃) | 3-F | CH(CH₃) | X/Y-14 | 5-OCH₂CH₃ |
| CH₂ | 3-F | CH₂ | X/Y-14 | 5-OCH₂CH₃ |
| CH₂CH₂ | H | CH₂CH₂ | X/Y-14 | 4-Cyclopropyl |
| CH₂CH₂ | H | CH₂CH₂ | X/Y-14 | 5-Cyclopropyl |
| CH₂CH₂ | H | CH₂CH₂CH₂ | X/Y-14 | 5-Cl |
| CH₂CH₂ | H | CH₂CH₂ | X/Y-14 | 4-CH₃ |
| CH₂ | H | CH₂ | X/Y-20 | 1-CH₃ |
| CH₂ | H | CH₂ | X/Y-20 | 1,5-(CH₃)₂ |
| CH(CH₃) | H | CH(CH₃) | X/Y-20 | 1-CH₃ |
| CH(CH₃) | 3-F | CH(CH₃) | X/Y-20 | 1,5-(CH₃)₂ |
| CH₂CH₂ | H | CH₂CH₂ | X/Y-20 | 1-CH₃ |
| CH₂CH₂ | H | CH₂CH₂ | X/Y-20 | 1,5-(CH₃)₂ |
| CH(CH₃)CH₂ | 3-F | CH(CH₃)CH₂ | X/Y-20 | 1,5-(CH₃)₂ |
| CH₂ | H | CH₂ | X/Y-3 | — |
| CH₂ | H | CH₂ | X/Y-3 | 3-CH₃ |
| CH₂ | H | CH₂ | X/Y-3 | 3-CH₂CH₃ |
| CH₂ | H | CH₂ | X/Y-3 | 3-CH(CH₃)₂ |
| CH₂ | H | CH₂ | X/Y-3 | 3-Cyclopropyl |
| CH₂ | H | CH₂ | X/Y-3 | 3-OCH₂CH₃ |
| CH₂ | H | CH₂ | X/Y-3 | 3-CH₂OCH₃ |
| CH₂ | H | CH₂ | X/Y-3 | 3-CF₃ |
| CH(CH₃) | H | CH₂ | X/Y-3 | 3-CH₃ |
| CH(CH₃) | H | CH₂ | X/Y-3 | 3-CH(CH₃)₂ |
| CH(CH₃) | H | CH₂ | X/Y-3 | 3-Cyclopropyl |
| CH₂ | H | CH(CH₃) | X/Y-3 | 3-CH₃ |
| CH₂ | H | CH(CH₃) | X/Y-3 | 3-CH(CH₃)₂ |
| CH₂ | H | CH(CH₃) | X/Y-3 | 3-Cyclopropyl |
| CH(CH₃) | H | CH(CH₃) | X/Y-3 | 3-CH₃ |
| CH(CH₃) | 3-F | CH(CH₃) | X/Y-3 | 3-CH(CH₃)₂ |
| CH(CH₃) | H | CH(CH₃) | X/Y-3 | 3-Cyclopropyl |
| CH₂ | H | CH₂CH₂ | X/Y-3 | 3-CH₃ |
| CH₂CH₂ | H | CH₂CH₂CH₂ | X/Y-3 | 3-CH(CH₃)₂ |
| CH₂CH₂ | H | CH₂CH₂ | X/Y-3 | 3-Cyclopropyl |
| CH₂CH₂ | H | CH₂CH(CH₃) | X/Y-3 | 3-Cyclopropyl |
| CH₂CH₂ | H | CH₂CH(CH₃) | X/Y-3 | 3-CH(CH₃)₂ |
| CH₂CH₂CH₂ | 3-F | CH(CH₃)CH₂ | X/Y-3 | 3-CH₃ |
| CH₂ | H | CH₂ | X/Y-5 | — |
| CH₂ | H | CH₂ | X/Y-5 | 5-OCH₂CH₃ |
| CH₂ | H | CH₂ | X/Y-5 | 5-Cyclopropyl |
| CH₂ | H | CH₂ | X/Y-5 | 5-CH₃ |
| CH(CH₃) | 3-F | CH(CH₃) | X/Y-5 | 5-CH₃ |
| CH(CH₃) | H | CH(CH₃) | X/Y-5 | 5-Cyclopropyl |
| CH(CH₃) | H | CH₂ | X/Y-5 | 5-Cyclopropyl |
| CH₂ | H | CH₂CH₂ | X/Y-5 | 5-OCH₂CH₃ |
| CH₂CH₂ | H | CH₂CH₂CH₂ | X/Y-5 | 5-CH₃ |
| CH₂ | H | CH₂ | X/Y-4 | — |
| CH₂ | H | CH₂ | X/Y-4 | 3-OCH₂CH₃ |
| CH₂ | H | CH₂ | X/Y-4 | 5-OCH₂CH₃ |
| CH₂ | H | CH₂ | X/Y-4 | 3-CH(CH₃)₂ |
| CH₂ | H | CH₂ | X/Y-4 | 5-CH₃ |
| CH(CH₃) | H | CH(CH₃) | X/Y-4 | 3-CH(CH₃)₂ |
| CH₂ | H | CH₂ | X/Y-11 | — |
| CH₂ | H | CH₂ | X/Y-11 | 3-CH₃ |
| CH₂ | H | CH₂ | X/Y-11 | 5-CH₃ |
| CH₂ | H | CH(CH₃) | X/Y-11 | 3-CH₃ |
| CH₂ | 3-F | CH(CH₃) | X/Y-11 | 5-CH₃ |
| CH(CH₃) | H | CH(CH₃) | X/Y-11 | 5-CH₃ |

TABLE B-continued (for structure I.B)

| A | R¹ | B | Y | Substituent on Y |
|---|---|---|---|---|
| CH₂ | H | CH₂ | X/Y-21 | — |
| CH₂ | H | CH₂ | X/Y-21 | 4,5-(CH₃)₂ |
| CH₂ | H | CH₂ | X/Y-21 | 4,5-Br₂ |
| CH(CH₃) | H | CH(CH₃) | X/Y-21 | 4,5-Cl₂ |
| CH(CH₃) | H | CH(CH₃) | X/Y-21 | 4,5-(CH₃)₂ |
| CH(CH₃) | H | CH(CH₃) | X/Y-21 | 4,5-Br₂ |
| CH₂ | H | CH₂ | X/Y-30 | — |
| CH₂ | H | CH₂ | X/Y-30 | 3,5-(CH₃)₂ |
| CH(CH₃) | H | CH(CH₃) | X/Y-30 | — |
| CH(CH₃) | H | CH(CH₃) | X/Y-30 | 3,5-(CH₃)₂ |
| CH₂ | H | CH₂ | X/Y-27 | — |
| CH₂ | H | CH₂ | X/Y-27 | 2-Cl |
| CH₂ | H | CH₂ | X/Y-27 | 2,5-(CH₃)₂ |
| CH(CH₃) | H | CH(CH₃) | X/Y-27 | — |
| CH(CH₃) | H | CH(CH₃) | X/Y-27 | 2-Cl |
| CH(CH₃) | H | CH(CH₃) | X/Y-27 | 2,5-(CH₃)₂ |

TABLE C (for structure I.C)

| A | R¹ | B | Y | Substituent on Y |
|---|---|---|---|---|
| CH₂ | H | CH₂ | X/Y-1 | |
| CH(CH₃) | H | CH₂ | X/Y-1 | |
| CH(CH₂CH₃) | H | CH₂ | X/Y-1 | |
| CH₂ | H | CH(CH₃) | X/Y-1 | |
| CH₂ | H | CH(CH₂CH₃) | X/Y-1 | |
| CH₂ | 3-CH₃ | CH₂ | X/Y-1 | |
| CH₂ | 3-F | CH₂ | X/Y-1 | |
| CH₂ | H | CH₂ | X/Y-1 | 5-CH₃ |
| CH₂ | H | CH₂ | X/Y-1 | 4-CH₃ |
| CH₂ | H | CH₂ | X/Y-1 | 3-CH₃ |
| CH₂ | H | CH₂ | X/Y-1 | 5-Cyclopropyl |
| CH₂ | H | CH₂ | X/Y-1 | 4-Cyclopropyl |
| CH₂ | H | CH₂ | X/Y-1 | 3-Cyclopropyl |
| CH₂ | H | CH₂ | X/Y-1 | 5-Cl |
| CH₂ | H | CH₂ | X/Y-1 | 5-Br |
| CH₂ | H | CH₂ | X/Y-1 | 4-Cl |
| CH₂ | H | CH₂ | X/Y-1 | 4-Br |
| CH₂ | H | CH₂ | X/Y-1 | 4,5-Cl,Cl |
| CH₂ | H | CH₂ | X/Y-1 | 4-OCH₂CH₃ |
| CH(CH₃) | H | CH₂ | X/Y-1 | 5-Br |
| CH(CH₃) | H | CH₂ | X/Y-1 | 4,5-Cl,Cl |
| CH(CH₃) | H | CH₂ | X/Y-1 | 4-Cl |
| CH₂ | H | CH(CH₃) | X/Y-1 | 5-Br |
| CH₂ | H | CH(CH₃) | X/Y-1 | 4,5-Cl,Cl |
| CH(CH₃) | H | CH(CH₃) | X/Y-1 | — |
| CH(CH₃) | H | CH(CH₃) | X/Y-1 | 4,5-Cl,Cl |
| CH(CH₃) | 3-F | CH(CH₃) | X/Y-1 | — |
| CH(CH₃) | 3-F | CH(CH₃) | X/Y-1 | 5-Br |
| CH₂CH₂ | H | CH₂ | X/Y-1 | 5-Br |
| CH₂CH₂ | H | CH₂CH₂ | X/Y-1 | 4,5-Cl,Cl |
| CH₂CH₂CH₂ | H | CH₂ | X/Y-1 | 5-Br |
| CH₂CH₂ | H | CH₂CH₂CH₂ | X/Y-1 | 4,5-Cl,Cl |
| CH₂CH(CH₃) | H | CH₂CH₂ | X/Y-1 | 4,5-Cl,Cl |
| CH₂CH₂ | 3-F | CH₂CH(CH₃) | X/Y-1 | 5-Br |
| CH₂ | H | CH₂ | X/Y-2 | — |
| CH₂ | H | CH₂ | X/Y-2 | 4-Cyclopropy |
| CH₂ | H | CH₂ | X/Y-2 | 5-Cyclopropy |
| CH₂ | H | CH₂ | X/Y-2 | 5-Cl |
| CH₂ | H | CH₂ | X/Y-2 | 4,5-Cl,Cl |
| CH₂ | H | CH₂ | X/Y-2 | 4,5-Br,Br |
| CH₂ | H | CH₂ | X/Y-2 | 4-CH₃ |
| CH₂ | H | CH₂ | X/Y-2 | 5-CH₃ |
| CH₂ | H | CH₂ | X/Y-2 | 4-OCH₃ |
| CH₂ | H | CH₂ | X/Y-2 | 5-OCH₃ |
| CH(CH₃) | H | CH₂ | X/Y-2 | 4,5-Cl,Cl |
| CH(CH₃) | H | CH₂ | X/Y-2 | 4,5-Br,Br |
| CH₂ | H | CH(CH₃) | X/Y-2 | 4,5-Cl,Cl |
| CH₂ | H | CH(CH₃) | X/Y-2 | 4,5-Br,Br |
| CH(CH₃) | H | CH(CH₃) | X/Y-2 | 4,5-Cl,Cl |
| CH(CH₃) | H | CH(CH₃) | X/Y-2 | 4,5-Br,Br |
| CH(CH₃) | 3-F | CH(CH₃) | X/Y-2 | 4,5-Cl,Cl |
| CH(CH₃) | 3-F | CH(CH₃) | X/Y-2 | 4,5-Br,Br |
| CH₂CH₂ | H | CH₂ | X/Y-2 | 4,5-Cl,Cl |
| CH₂CH₂ | H | CH₂CH₂ | X/Y-2 | 4,5-Br,Br |
| CH₂CH₂CH₂ | H | CH₂ | X/Y-2 | 4,5-Cl,Cl |

TABLE C-continued (for structure I.C)

| A | R¹ | B | Y | Substituent on Y |
|---|---|---|---|---|
| CH₂CH₂ | H | CH₂CH₂CH₂ | X/Y-2 | 4,5-Br,Br |
| CH₂CH(CH₃) | H | CH₂CH₂ | X/Y-2 | 4,5-Br,Br |
| CH₂CH₂ | 3-F | CH₂CH(CH₃) | X/Y-2 | 4,5-Cl,Cl |
| CH₂ | H | CH₂ | X/Y-15 | — |
| CH₂ | H | CH₂ | X/Y-15 | 2-CH₃ |
| CH₂ | H | CH₂ | X/Y-15 | 2-Cyclopropyl |
| CH₂ | H | CH₂ | X/Y-15 | 2-OCH₂CH₃ |
| CH₂ | H | CH₂ | X/Y-15 | 2-Cl |
| CH(CH₃) | H | CH₂ | X/Y-15 | 2-Cyclopropyl |
| CH(CH₃) | H | CH₂ | X/Y-15 | 2-OCH₂CH₃ |
| CH₂ | H | CH(CH₃) | X/Y-15 | 2-Cyclopropyl |
| CH₂ | H | CH(CH₃) | X/Y-15 | 2-OCH₂CH₃ |
| CH(CH₃) | H | CH(CH₃) | X/Y-15 | 2-Cyclopropyl |
| CH(CH₃) | H | CH(CH₃) | X/Y-15 | 2-OCH₂CH₃ |
| CH(CH₃) | 3-F | CH(CH₃) | X/Y-15 | 2-Cyclopropyl |
| CH(CH₃) | 3-F | CH(CH₃) | X/Y-15 | 2-OCH₂CH₃ |
| CH₂CH₂ | H | CH₂ | X/Y-15 | 2-Cyclopropyl |
| CH₂CH₂ | H | CH₂CH₂ | X/Y-15 | 2-OCH₂CH₃ |
| CH₂CH₂CH₂ | H | CH₂ | X/Y-15 | 2-Cyclopropyl |
| CH₂CH₂ | H | CH₂CH₂CH₂ | X/Y-15 | 2-OCH₂CH₃ |
| CH₂CH(CH₃) | H | CH₂CH₂ | X/Y-15 | 2-Cyclopropyl |
| CH₂CH₂ | 3-F | CH₂CH(CH₃) | X/Y-15 | 2-OCH₂CH₃ |
| CH₂ | H | CH₂ | X/Y-12 | — |
| CH₂ | H | CH₂ | X/Y-12 | 2-CH₃ |
| CH₂ | H | CH₂ | X/Y-12 | 2-Cyclopropyl |
| CH₂ | H | CH₂ | X/Y-12 | 2-OCH₂CH₃ |
| CH(CH₃) | H | CH₂ | X/Y-12 | 2-Cyclopropyl |
| CH(CH₃) | H | CH₂ | X/Y-12 | 2-OCH₂CH₃ |
| CH₂ | H | CH(CH₃) | X/Y-12 | 2-Cyclopropyl |
| CH₂ | H | CH(CH₃) | X/Y-12 | 2-OCH₂CH₃ |
| CH(CH₃) | H | CH(CH₃) | X/Y-12 | 2-Cyclopropyl |
| CH(CH₃) | 3-F | CH(CH₃) | X/Y-12 | 2-OCH₂CH₃ |
| CH₂CH₂ | H | CH₂ | X/Y-12 | 2-Cyclopropyl |
| CH₂CH₂ | H | CH₂CH₂ | X/Y-12 | 2-OCH₂CH₃ |
| CH₂CH₂CH₂ | H | CH₂ | X/Y-12 | 2-Cyclopropyl |
| CH₂CH₂ | H | CH₂CH₂CH₂ | X/Y-12 | 2-OCH₂CH₃ |
| CH₂CH(CH₃) | H | CH₂CH₂ | X/Y-12 | 2-Cyclopropyl |
| CH₂CH₂ | 3-F | CH₂CH(CH₃) | X/Y-12 | 2-Cyclopropyl |
| CH₂ | H | CH₂ | X/Y-18 | 1-CH₃ |
| CH₂ | H | CH₂ | X/Y-18 | 1,2-(CH₃)₂ |
| CH₂ | H | CH₂ | X/Y-18 | 1,4-(CH₃)₂ |
| CH₂ | H | CH₂ | X/Y-18 | 1,2,4-(CH₃)₃ |
| CH₂ | H | CH₂ | X/Y-18 | 1-CH₃, 2-Cyclopropyl |
| CH(CH₃) | H | CH₂ | X/Y-18 | 1-CH₃, 2-Cyclopropyl |
| CH(CH₃) | H | CH₂ | X/Y-18 | 1,2,4-(CH₃)₃ |
| CH₂ | H | CH(CH₃) | X/Y-18 | 1-CH₃, 2-Cyclopropyl |
| CH₂ | H | CH(CH₃) | X/Y-18 | 1,2,4-(CH₃)₃ |
| CH(CH₃) | H | CH(CH₃) | X/Y-18 | 1-CH₃, 2-Cyclopropyl |
| CH(CH₃) | 3-F | CH(CH₃) | X/Y-18 | 1,2,4-(CH₃)₃ |
| CH₂CH₂ | H | CH₂ | X/Y-18 | 1-CH₃, 2-Cyclopropyl |
| CH₂CH₂ | H | CH₂CH₂ | X/Y-18 | 1,2,4-(CH₃)₂ |
| CH₂CH₂CH₂ | H | CH₂ | X/Y-18 | 1-CH₃, 2-Cyclopropyl |
| CH₂CH₂ | H | CH₂CH₂CH₂ | X/Y-18 | 1,2,4-(CH₃)₂ |
| CH₂CH(CH₃) | H | CH₂CH₂ | X/Y-18 | 1-CH₃, 2-Cyclopropyl |
| CH₂CH₂ | 3-F | CH₂CH(CH₃) | X/Y-18 | 1,2,4-(CH₃)₂ |
| CH₂ | H | CH₂ | X/Y-19 | 1-CH₃ |
| CH₂ | H | CH₂ | X/Y-19 | 1,2-(CH₃)₂ |
| CH₂ | H | CH₂ | X/Y-19 | 1,5-(CH₃)₂ |
| CH₂ | H | CH₂ | X/Y-19 | 1-CH₃, 2-Cyclopropyl |
| CH(CH₃) | H | CH₂ | X/Y-19 | 1,2-(CH₃)₂ |
| CH(CH₃) | H | CH₂ | X/Y-19 | 1-CH₃, 2-Cyclopropyl |
| CH₂ | H | CH(CH₃) | X/Y-19 | 1,2-(CH₃)₂ |
| CH₂ | H | CH(CH₃) | X/Y-19 | 1-CH₃, 2-Cyclopropyl |
| CH(CH₃) | H | CH(CH₃) | X/Y-19 | 1,2-(CH₃)₂ |
| CH(CH₃) | H | CH(CH₃) | X/Y-19 | 1-CH₃, 2-Cyclopropyl |
| CH(CH₃) | 3-F | CH₂ | X/Y-19 | 1-CH₃, 2-Cyclopropyl |

TABLE C-continued (for structure I.C)

| A | R¹ | B | Y | Substituent on Y |
|---|---|---|---|---|
| CH₂CH₂ | H | CH₂ | X/Y-19 | 1-CH₃, 2-Cyclopropyl |
| CH₂CH₂ | H | CH₂CH₂ | X/Y-19 | 1,2-(CH₃)₂ |
| CH₂CH₂CH₂ | H | CH₂ | X/Y-19 | 1-CH₃, 2-Cyclopropyl |
| CH₂CH₂ | H | CH₂CH₂CH₂ | X/Y-19 | 1,2-(CH₃)₂ |
| CH₂CH(CH₃) | H | CH₂CH₂ | X/Y-19 | 1-CH₃, 2-Cyclopropyl |
| CH₂CH₂ | 3-F | CH₂CH(CH₃) | X/Y-19 | 1,2-(CH₃)₂ |
| CH₂ | H | CH₂ | X/Y-16 | — |
| CH₂ | H | CH₂ | X/Y-16 | 2-CH₃ |
| CH₂ | H | CH₂ | X/Y-16 | 2-Cyclopropyl |
| CH₂ | H | CH₂ | X/Y-16 | 2-Cl |
| CH₂ | H | CH₂ | X/Y-16 | 2-OCH₂CH₃ |
| CH(CH₃) | H | CH₂ | X/Y-16 | 2-CH₃ |
| CH(CH₃) | H | CH₂ | X/Y-16 | 2-Cyclopropyl |
| CH₂ | H | CH(CH₃) | X/Y-16 | 2-CH₃ |
| CH₂ | H | CH(CH₃) | X/Y-16 | 2-Cyclopropyl |
| CH₂(CH₃) | H | CH(CH₃) | X/Y-16 | 2-CH₃ |
| CH₂(CH₃) | H | CH(CH₃) | X/Y-16 | 2-Cyclopropyl |
| CH₂(CH₃) | 3-F | CH(CH₃) | X/Y-16 | 2-Cyclopropyl |
| CH₂CH₂ | H | CH₂ | X/Y-16 | 2-Cyclopropyl |
| CH₂CH₂ | H | CH₂CH₂ | X/Y-16 | 2-CH₃ |
| CH₂CH₂CH₂ | H | CH₂ | X/Y-16 | 2-Cyclopropyl |
| CH₂CH₂ | H | CH₂CH₂CH₂ | X/Y-16 | 2-CH₃ |
| CH₂CH(CH₃) | H | CH₂CH₂ | X/Y-16 | 2-Cyclopropyl |
| CH₂CH₂ | 3-F | CH₂CH(CH₃) | X/Y-16 | 2-CH₃ |
| CH₂ | H | CH₂ | X/Y-13 | — |
| CH₂ | H | CH₂ | X/Y-13 | 2-CH₃ |
| CH₂ | H | CH₂ | X/Y-13 | 2-Cyclopropyl |
| CH₂ | H | CH₂ | X/Y-13 | 2-OCH₂CH₃ |
| CH(CH₃) | H | CH₂ | X/Y-13 | 2-OCH₂CH₃ |
| CH(CH₃) | H | CH₂ | X/Y-13 | 2-Cyclopropyl |
| CH₂ | H | CH(CH₃) | X/Y-13 | 2-OCH₂CH₃ |
| CH₂ | H | CH(CH₃) | X/Y-13 | 2-Cyclopropyl |
| CH(CH₃) | H | CH(CH₃) | X/Y-13 | 2-OCH₂CH₃ |
| CH(CH₃) | 3-F | CH(CH₃) | X/Y-13 | 2-Cyclopropyl |
| CH₂CH₂ | H | CH₂ | X/Y-13 | 2-Cyclopropyl |
| CH₂CH₂ | H | CH₂CH₂ | X/Y-13 | 2-CH₃ |
| CH₂CH₂CH₂ | H | CH₂ | X/Y-13 | 2-Cyclopropyl |
| CH₂CH₂ | H | CH₂CH₂CH₂ | X/Y-13 | 2-CH₃ |
| CH(CH₃)CH₂ | 3-F | CH₂CH₂ | X/Y-13 | 2-Cyclopropyl |
| CH₂CH₂ | H | CH(CH₃)CH₂ | X/Y-13 | 2-CH₃ |
| CH₂ | H | CH₂ | X/Y-6 | — |
| CH₂ | H | CH₂ | X/Y-6 | 3-CH₃ |
| CH₂ | H | CH₂ | X/Y-6 | 3-Cyclopropyl |
| CH₂ | H | CH₂ | X/Y-6 | 3-OCH₂CH₃ |
| CH(CH₃) | H | CH(CH₃) | X/Y-6 | 3-Cyclopropyl |
| CH(CH₃) | 3-F | CH(CH₃) | X/Y-6 | 3-Cyclopropyl |
| CH₂CH₂ | H | CH₂CH₂ | X/Y-6 | 3-Cyclopropyl |
| CH₂CH₂ | H | CH₂CH₂CH₂ | X/Y-6 | 3-CH₃ |
| CH(CH₃)CH₂ | 3-F | CH₂CH₂ | X/Y-6 | 3-Cyclopropyl |
| CH₂CH₂ | H | CH(CH₃)CH₂ | X/Y-6 | 3-Cyclopropyl |
| CH₂ | H | CH₂ | X/Y-8 | 1-CH₃ |
| CH₂ | H | CH₂ | X/Y-8 | 1,3-(CH₃)₂ |
| CH₂ | H | CH₂ | X/Y-8 | 1,4-(CH₃)₂ |
| CH₂ | H | CH₂ | X/Y-8 | 1-CH₃, 3-Cyclopropyl |
| CH(CH₃) | H | CH(CH₃) | X/Y-8 | 1-CH₃, 3-Cyclopropyl |
| CH(CH₃) | 3-F | CH(CH₃) | X/Y-8 | 1-CH₃, 3-Cyclopropyl |
| CH₂CH₂ | H | CH₂CH₂ | X/Y-8 | 1-CH₃, 3-Cyclopropyl |
| CH₂CH₂ | H | CH₂CH₂CH₂ | X/Y-8 | 1,3-(CH₃)₂ |
| CH₂CH(CH₃) | H | CH₂CH₂ | X/Y-8 | 1-CH₃, 3-Cyclopropyl |
| CH(CH₃)CH₂ | 3-F | CH₂CH₂ | X/Y-8 | 1-CH₃, 3-Cyclopropyl |
| CH₂ | H | CH₂ | X/Y-10 | 1-CH₃ |
| CH₂ | H | CH₂ | X/Y-10 | 1,4-(CH₃)₂ |
| CH₂ | H | CH₂ | X/Y-10 | 1-CH₃, 4-OCH₃ |
| CH₂ | H | CH₂ | X/Y-10 | 1-CH₃, 5-CH(CH₃)₂ |
| CH₂ | H | CH₂ | X/Y-10 | 1-CH₃, 5-Cyclopropyl |
| CH(CH₃) | H | CH(CH₃) | X/Y-10 | 1-CH₃, 5-Cyclopropyl |
| CH(CH₃) | 3-F | CH(CH₃) | X/Y-10 | 1,4-(CH₃)₂ |
| CH₂CH₂ | H | CH₂CH₂ | X/Y-10 | 1-CH₃, 5-Cyclopropyl |
| CH₂CH₂ | H | CH₂CH₂CH₂ | X/Y-10 | 1,5-(CH₃)₂ |
| CH₂CH(CH₃) | H | CH₂CH₂ | X/Y-10 | 1-CH₃, 5-Cyclopropyl |
| CH(CH₃)CH₂ | 3-F | CH₂CH₂ | X/Y-10 | 1-CH₃, 5-Cyclopropyl |
| CH₂ | H | CH₂ | X/Y-7 | — |
| CH₂ | H | CH₂ | X/Y-7 | 3-CH₃ |
| CH(CH₃) | H | CH(CH₃) | X/Y-7 | 3-CH₃ |
| CH(CH₃) | 3-F | CH(CH₃) | X/Y-7 | 3-CH₃ |
| CH₂CH₂ | H | CH₂ | X/Y-7 | 3-CH₃ |
| CH₂CH₂ | 3-F | CH(CH₃)CH₂ | X/Y-7 | 3-CH₃ |
| CH₂ | H | CH₂ | X/Y-9 | 1-CH₃ |
| CH₂ | H | CH₂ | X/Y-9 | 1,3-(CH₃)₂ |
| CH₂ | H | CH₂ | X/Y-9 | 1,5-(CH₃)₂ |
| CH(CH₃) | H | CH(CH₃) | X/Y-9 | 1,3-(CH₃)₂ |
| CH(CH₃) | 3-F | CH(CH₃) | X/Y-9 | 1,5-(CH₃)₂ |
| CH₂CH₂ | H | CH₂CH₂ | X/Y-9 | 1,3-(CH₃)₂ |
| CH₂CH₂ | H | CH₂CH₂CH₂ | X/Y-9 | 1,5-(CH₃)₂ |
| CH₂CH(CH₃) | H | CH₂CH₂ | X/Y-9 | 1,3-(CH₃)₂ |
| CH(CH₃)CH₂ | 3-F | CH₂CH₂ | X/Y-9 | 1,5-(CH₃)₂ |
| CH₂ | H | CH₂ | X/Y-25 | 5-CH₂CH₃ |
| CH₂ | H | CH₂ | X/Y-25 | 5-CH(CH₃)₂ |
| CH₂ | H | CH₂ | X/Y-25 | 5-OCH₃ |
| CH(CH₃) | H | CH(CH₃) | X/Y-25 | 5-Cyclopropyl |
| CH₂(CH₃) | H | CH(CH₃) | X/Y-25 | 5-CH₃ |
| CH(CH₃) | H | CH(CH₃) | X/Y-25 | 5-OCH₂CH₃ |
| CH(CH₃) | 3-F | CH(CH₃) | X/Y-25 | 5-Cyclopropyl |
| CH₂CH₂ | H | CH₂ | X/Y-25 | 5-Cyclopropyl |
| CH₂CH₂ | H | CH₂CH₂ | X/Y-25 | 5-CH₃ |
| CH₂CH₂CH₂ | H | CH₂ | X/Y-25 | 5-OCH₂CH₃ |
| CH₂CH₂ | 3-F | CH₂CH(CH₃) | X/Y-25 | 5-Cyclopropyl |
| CH₂CH₂ | H | CH(CH₃) | X/Y-25 | 5-Cyclopropyl |
| CH₂ | H | CH₂ | X/Y-23 | — |
| CH₂ | H | CH₂ | X/Y-23 | 5-CH₃ |
| CH₂ | H | CH₂ | X/Y-23 | 5-CH(CH₃)₂ |
| CH₂ | H | CH₂ | X/Y-23 | 5-Cl |
| CH₂ | H | CH₂ | X/Y-23 | 5-OCH₂CH₃ |
| CH₂ | H | CH(CH₃) | X/Y-23 | 5-Cyclopropyl |
| CH₂ | 3-F | CH(CH₃) | X/Y-23 | 5-CH₃ |
| CH₂ | H | CH(CH₃) | X/Y-23 | 5-CH(CH₃)₂ |
| CH(CH₃) | H | CH(CH₃) | X/Y-23 | 5-Cyclopropyl |
| CH₂ | H | CH₂CH₂ | X/Y-23 | 5-Cyclopropyl |
| CH₂CH₂CH₂ | H | CH₂ | X/Y-23 | 5-CH₃ |
| CH₂CH₂ | H | CH₂CH₂ | X/Y-23 | 5-CH(CH₃)₂ |
| CH₂CH₂ | H | CH₂CH₂ | X/Y-23 | 5-Cyclopropyl |
| CH₂ | H | CH₂ | X/Y-26 | 1-CH₃ |
| CH₂ | H | CH₂ | X/Y-26 | 1,5-(CH₃)₂ |
| CH₂ | H | CH₂ | X/Y-26 | 1-CH₃, 5-Cyclopropyl |
| CH(CH₃) | H | CH(CH₃) | X/Y-26 | 1-CH₃, 5-Cyclopropyl |
| CH(CH₃) | H | CH(CH₃) | X/Y-26 | 1,5-(CH₃)₂ |
| CH(CH₃) | 3-F | CH₂ | X/Y-26 | 1-CH₃, 5-Cyclopropyl |
| CH₂CH₂ | H | CH₂CH₂ | X/Y-26 | 1-CH₃, 5-Cyclopropyl |
| CH₂ | H | CH₂CH₂ | X/Y-26 | 1,5-(CH₃)₂ |
| CH₂ | H | CH₂ | X/Y-28 | 1-CH₃ |
| CH₂ | H | CH₂ | X/Y-28 | 1,5-(CH₃)₂ |
| CH₂ | H | CH₂ | X/Y-28 | 1-CH₃, 5-Cyclopropyl |
| CH(CH₃) | H | CH(CH₃) | X/Y-28 | 1-CH₃, 5-Cyclopropyl |
| CH(CH₃) | H | CH(CH₃) | X/Y-28 | 1,5-(CH₃)₂ |
| CH(CH₃) | 3-F | CH₂ | X/Y-28 | 1-CH₃, 5-Cyclopropyl |
| CH₂CH₂ | H | CH₂CH₂ | X/Y-28 | 1-CH₃, 5-Cyclopropyl |
| CH₂CH₂ | H | CH₂CH₂ | X/Y-28 | 1,5-(CH₃)₂ |
| CH₂ | H | CH₂ | X/Y-22 | — |
| CH₂ | H | CH₂ | X/Y-22 | 3-CH₃ |
| CH₂ | H | CH₂ | X/Y-22 | 3-Cyclopropyl |
| CH₂ | H | CH₂ | X/Y-22 | 3-OCH₃ |

TABLE C-continued (for structure I.C)

| A | R¹ | B | Y | Substituent on Y |
|---|---|---|---|---|
| CH(CH₃) | H | CH₂ | X/Y-22 | 3-CH₃ |
| CH₂ | H | CH(CH₃) | X/Y-22 | 3-Cyclopropyl |
| CH₂ | 3-F | CH(CH₃) | X/Y-22 | 3-OCH₃ |
| CH₂CH₂ | H | CH₂CH₂ | X/Y-22 | 3-Cyclopropyl |
| CH₂ | H | CH₂CH₂ | X/Y-22 | 3-CH₃ |
| CH₂ | H | CH₂ | X/Y-29 | 1-CH₃ |
| CH₂ | H | CH₂ | X/Y-29 | 1,3-(CH₃)₂ |
| CH₂ | H | CH₂ | X/Y-29 | 1-CH₃, 3-Cyclopropyl |
| CH(CH₃) | H | CH(CH₃) | X/Y-29 | 1,3-(CH₃)₂ |
| CH(CH₃) | 3-F | CH(CH₃) | X/Y-29 | 1-CH₃, 3-Cyclopropyl |
| CH₂CH₂ | H | CH₂CH₂ | X/Y-29 | 1,3-(CH₃)₂ |
| CH₂CH₂ | H | CH₂CH₂ | X/Y-29 | 1-CH₃, 3-Cyclopropyl |
| CH₂ | H | CH₂ | X/Y-17 | — |
| CH₂ | H | CH₂ | X/Y-17 | 5-Cyclopropyl |
| CH₂ | H | CH₂ | X/Y-17 | 5-CH₃ |
| CH₂ | H | CH₂ | X/Y-17 | 5-OCH₂CH₃ |
| CH₂ | H | CH₂ | X/Y-17 | 5-Cl |
| CH₂ | H | CH₂ | X/Y-17 | 4-CH₃ |
| CH₂ | H | CH₂ | X/Y-17 | 4-Cyclopropyl |
| CH₂ | H | CH₂ | X/Y-17 | 4-OCH₂CH₃ |
| CH₂ | H | CH₂ | X/Y-17 | 4-Cl |
| CH(CH₃) | H | CH(CH₃) | X/Y-17 | 5-CH₃ |
| CH(CH₃) | H | CH(CH₃) | X/Y-17 | 4-Cyclopropyl |
| CH(CH₃) | 3-F | CH(CH₃) | X/Y-17 | 5-OCH₂CH₃ |
| CH₂CH₂ | H | CH₂CH₂ | X/Y-17 | 5-Cyclopropyl |
| CH₂CH₂ | H | CH₂CH₂ | X/Y-17 | 4-Cyclopropyl |
| CH₂CH₂ | H | CH₂CH₂CH₂ | X/Y-17 | 5-CH₃ |
| CH₂ | H | CH₂ | X/Y-14 | — |
| CH₂ | H | CH₂ | X/Y-14 | 5-CH₃ |
| CH₂ | H | CH₂ | X/Y-14 | 5-Cyclopropyl |
| CH₂ | H | CH₂ | X/Y-14 | 4-CH₃ |
| CH₂ | H | CH₂ | X/Y-14 | 4-Cyclopropyl |
| CH₂ | H | CH₂ | X/Y-14 | 4-OCH₂CH₃ |
| CH₂ | H | CH₂ | X/Y-14 | 5-OCH₂CH₃ |
| CH₂ | H | CH₂ | X/Y-14 | 5-Cl |
| CH(CH₃) | H | CH(CH₃) | X/Y-14 | 4-Cyclopropyl |
| CH(CH₃) | H | CH(CH₃) | X/Y-14 | 5-Cyclopropyl |
| CH(CH₃) | H | CH(CH₃) | X/Y-14 | 4-CH₃ |
| CH(CH₃) | 3-F | CH(CH₃) | X/Y-14 | 4-Cyclopropyl |
| CH₂ | 3-F | CH₂ | X/Y-14 | 5-OCH₂CH₃ |
| CH₂CH₂ | H | CH₂CH₂ | X/Y-14 | 4-Cyclopropyl |
| CH₂CH₂ | H | CH₂CH₂ | X/Y-14 | 5-Cyclopropyl |
| CH₂CH₂ | H | CH₂CH₂CH₂ | X/Y-14 | 5-Cl |
| CH₂CH₂ | H | CH₂CH₂ | X/Y-14 | 4-CH₃ |
| CH₂ | H | CH₂ | X/Y-20 | 1-CH₃ |
| CH₂ | H | CH₂ | X/Y-20 | 1,5-(CH₃)₂ |
| CH(CH₃) | H | CH(CH₃) | X/Y-20 | 1-CH₃ |
| CH(CH₃) | 3-F | CH(CH₃) | X/Y-20 | 1,5-(CH₃)₂ |
| CH₂CH₂ | H | CH₂CH₂ | X/Y-20 | 1-CH₃ |
| CH₂CH₂ | H | CH₂CH₂ | X/Y-20 | 1,5-(CH₃)₂ |
| CH(CH₃)CH₂ | 3-F | CH(CH₃)CH₂ | X/Y-20 | 1,5-(CH₃)₂ |
| CH₂ | H | CH₂ | X/Y-3 | — |
| CH₂ | H | CH₂ | X/Y-3 | 3-CH₃ |
| CH₂ | H | CH₂ | X/Y-3 | 3-CH₂CH₃ |
| CH₂ | H | CH₂ | X/Y-3 | 3-CH(CH₃)₂ |
| CH₂ | H | CH₂ | X/Y-3 | 3-OCH₂CH₃ |
| CH₂ | H | CH₂ | X/Y-3 | 3-CH₂OCH₃ |
| CH₂ | H | CH₂ | X/Y-3 | 3-CF₃ |
| CH(CH₃) | H | CH₂ | X/Y-3 | 3-CH₃ |
| CH(CH₃) | H | CH₂ | X/Y-3 | 3-CH(CH₃)₂ |
| CH(CH₃) | H | CH₂ | X/Y-3 | 3-Cyclopropyl |
| CH₂ | H | CH(CH₃) | X/Y-3 | 3-CH₃ |
| CH₂ | H | CH(CH₃) | X/Y-3 | 3-CH(CH₃)₂ |
| CH₂ | H | CH(CH₃) | X/Y-3 | 3-Cyclopropyl |
| CH(CH₃) | H | CH(CH₃) | X/Y-3 | 3-CH₃ |
| CH(CH₃) | 3-F | CH(CH₃) | X/Y-3 | 3-CH(CH₃)₂ |
| CH(CH₃) | H | CH(CH₃) | X/Y-3 | 3-Cyclopropyl |
| CH₂ | H | CH₂CH₂ | X/Y-3 | 3-CH₃ |
| CH₂CH₂ | H | CH₂CH₂CH₂ | X/Y-3 | 3-CH(CH₃)₂ |
| CH₂ | H | CH₂CH₂ | X/Y-3 | 3-Cyclopropyl |
| CH₂CH₂ | H | CH₂CH(CH₃) | X/Y-3 | 3-Cyclopropyl |
| CH₂CH₂ | H | CH₂CH(CH₃) | X/Y-3 | 3-CH(CH₃)₂ |
| CH₂CH₂CH₂ | 3-F | CH(CH₃)CH₂ | X/Y-3 | 3-CH₃ |
| CH₂ | H | CH₂ | X/Y-5 | — |
| CH₂ | H | CH₂ | X/Y-5 | 5-OCH₂CH₃ |
| CH₂ | H | CH₂ | X/Y-5 | 5-Cyclopropyl |
| CH₂ | H | CH₂ | X/Y-5 | 5-CH₃ |
| CH(CH₃) | 3-F | CH(CH₃) | X/Y-5 | 5-CH₃ |
| CH₂ | H | CH(CH₃) | X/Y-5 | 5-Cyclopropyl |
| CH(CH₃) | H | CH₂ | X/Y-5 | 5-Cyclopropyl |
| CH₂ | H | CH₂CH₂ | X/Y-5 | 5-OCH₂CH₃ |
| CH₂CH₂ | H | CH₂CH₂CH₂ | X/Y-5 | 5-CH₃ |
| CH₂ | H | CH₂ | X/Y-4 | — |
| CH₂ | H | CH₂ | X/Y-4 | 3-OCH₂CH₃ |
| CH₂ | H | CH₂ | X/Y-4 | 5-OCH₂CH₃ |
| CH₂ | H | CH₂ | X/Y-4 | 3-CH(CH₃)₂ |
| CH₂ | H | CH₂ | X/Y-4 | 5-CH₃ |
| CH(CH₃) | 3-F | CH(CH₃) | X/Y-4 | 3-CH(CH₃)₂ |
| CH₂ | H | CH₂ | X/Y-11 | — |
| CH₂ | H | CH₂ | X/Y-11 | 3-CH₃ |
| CH₂ | H | CH₂ | X/Y-11 | 5-CH₃ |
| CH₂ | H | CH(CH₃) | X/Y-11 | 3-CH₃ |
| CH₂ | 3-F | CH(CH₃) | X/Y-11 | 5-CH₃ |
| CH(CH₃) | H | CH(CH₃) | X/Y-11 | 5-CH₃ |
| CH₂ | H | CH₂ | X/Y-21 | — |
| CH₂ | H | CH₂ | X/Y-21 | 4,5-(CH₃)₂ |
| CH₂ | H | CH₂ | X/Y-21 | 4,5-Br₂ |
| CH(CH₃) | H | CH(CH₃) | X/Y-21 | 4,5-Cl₂ |
| CH(CH₃) | H | CH(CH₃) | X/Y-21 | 4,5-(CH₃)₂ |
| CH(CH₃) | H | CH(CH₃) | X/Y-21 | 4,5-Br₂ |
| CH₂ | H | CH₂ | X/Y-30 | — |
| CH₂ | H | CH₂ | X/Y-30 | 3,5-(CH₃)₂ |
| CH(CH₃) | H | CH(CH₃) | X/Y-30 | — |
| CH(CH₃) | H | CH(CH₃) | X/Y-30 | 3,5-(CH₃)₂ |
| CH₂ | H | CH₂ | X/Y-27 | — |
| CH₂ | H | CH₂ | X/Y-27 | 2-Cl |
| CH₂ | H | CH₂ | X/Y-27 | 2,5-(CH₃)₂ |
| CH(CH₃) | H | CH(CH₃) | X/Y-27 | — |
| CH(CH₃) | H | CH(CH₃) | X/Y-27 | 2-Cl |
| CH(CH₃) | H | CH(CH₃) | X/Y-27 | 2,5-(CH₃)₂ |

TABLE D (for structure I.D)

| A | R¹ | B | Y | Substituent on Y |
|---|---|---|---|---|
| CH₂ | H | CH₂ | X/Y-1 | |
| CH(CH₃) | H | CH₂ | X/Y-1 | |
| CH(CH₂CH₃) | H | CH₂ | X/Y-1 | |
| CH₂ | H | CH(CH₃) | X/Y-1 | |
| CH₂ | H | CH(CH₂CH₃) | X/Y-1 | |
| CH₂ | 3-CH₃ | CH₂ | X/Y-1 | |
| CH₂ | 3-F | CH₂ | X/Y-1 | |
| CH₂ | H | CH₂ | X/Y-1 | 5-CH₃ |
| CH₂ | H | CH₂ | X/Y-1 | 4-CH₃ |
| CH₂ | H | CH₂ | X/Y-1 | 3-CH₃ |
| CH₂ | H | CH₂ | X/Y-1 | 5-Cyclopropyl |
| CH₂ | H | CH₂ | X/Y-1 | 4-Cyclopropyl |
| CH₂ | H | CH₂ | X/Y-1 | 3-Cyclopropyl |
| CH₂ | H | CH₂ | X/Y-1 | 5-Cl |
| CH₂ | H | CH₂ | X/Y-1 | 5-Br |
| CH₂ | H | CH₂ | X/Y-1 | 4-Cl |

TABLE D-continued (for structure I.D)

| A | R¹ | B | Y | Substituent on Y |
|---|---|---|---|---|
| $CH_2$ | H | $CH_2$ | X/Y-1 | 4-Br |
| $CH_2$ | H | $CH_2$ | X/Y-1 | 4,5-Cl,Cl |
| $CH_2$ | H | $CH_2$ | X/Y-1 | 4-OCH$_2$CH$_3$ |
| $CH(CH_3)$ | H | $CH_2$ | X/Y-1 | 5-Br |
| $CH(CH_3)$ | H | $CH_2$ | X/Y-1 | 4,5-Cl,Cl |
| $CH(CH_3)$ | H | $CH_2$ | X/Y-1 | 4-Cl |
| $CH_2$ | H | $CH(CH_3)$ | X/Y-1 | 5-Br |
| $CH_2$ | H | $CH(CH_3)$ | X/Y-1 | 4,5-Cl,Cl |
| $CH(CH_3)$ | H | $CH(CH_3)$ | X/Y-1 | — |
| $CH(CH_3)$ | H | $CH(CH_3)$ | X/Y-1 | 4,5-Cl,Cl |
| $CH(CH_3)$ | 3-F | $CH(CH_3)$ | X/Y-1 | — |
| $CH(CH_3)$ | 3-F | $CH(CH_3)$ | X/Y-1 | 5-Br |
| $CH_2CH_2$ | H | $CH_2$ | X/Y-1 | 5-Br |
| $CH_2CH_2$ | H | $CH_2CH_2$ | X/Y-1 | 4,5-Cl,Cl |
| $CH_2CH_2CH_2$ | H | $CH_2$ | X/Y-1 | 5-Br |
| $CH_2CH_2$ | H | $CH_2CH_2CH_2$ | X/Y-1 | 4,5-Cl,Cl |
| $CH_2CH(CH_3)$ | H | $CH_2CH_2$ | X/Y-1 | 4,5-Cl,Cl |
| $CH_2CH_2$ | 3-F | $CH_2CH(CH_3)$ | X/Y-1 | 5-Br |
| $CH_2$ | H | $CH_2$ | X/Y-2 | — |
| $CH_2$ | H | $CH_2$ | X/Y-2 | 4-Cyclopropyl |
| $CH_2$ | H | $CH_2$ | X/Y-2 | 5-Cyclopropyl |
| $CH_2$ | H | $CH_2$ | X/Y-2 | 5-Cl |
| $CH_2$ | H | $CH_2$ | X/Y-2 | 4,5-Cl,Cl |
| $CH_2$ | H | $CH_2$ | X/Y-2 | 4,5-Br,Br |
| $CH_2$ | H | $CH_2$ | X/Y-2 | 4-CH$_3$ |
| $CH_2$ | H | $CH_2$ | X/Y-2 | 5-CH$_3$ |
| $CH_2$ | H | $CH_2$ | X/Y-2 | 4-OCH$_3$ |
| $CH_2$ | H | $CH_2$ | X/Y-2 | 5-OCH$_3$ |
| $CH(CH_3)$ | H | $CH_2$ | X/Y-2 | 4,5-Cl,Cl |
| $CH(CH_3)$ | H | $CH_2$ | X/Y-2 | 4,5-Br,Br |
| $CH_2$ | H | $CH(CH_3)$ | X/Y-2 | 4,5-Cl,Cl |
| $CH_2$ | H | $CH(CH_3)$ | X/Y-2 | 4,5-Br,Br |
| $CH(CH_3)$ | H | $CH(CH_3)$ | X/Y-2 | 4,5-Cl,Cl |
| $CH(CH_3)$ | H | $CH(CH_3)$ | X/Y-2 | 4,5-Br,Br |
| $CH(CH_3)$ | 3-F | $CH(CH_3)$ | X/Y-2 | 4,5-Cl,Cl |
| $CH(CH_3)$ | 3-F | $CH(CH_3)$ | X/Y-2 | 4,5-Br,Br |
| $CH_2CH_2$ | H | $CH_2$ | X/Y-2 | 4,5-Cl,Cl |
| $CH_2CH_2$ | H | $CH_2CH_2$ | X/Y-2 | 4,5-Br,Br |
| $CH_2CH_2CH_2$ | H | $CH_2$ | X/Y-2 | 4,5-Cl,Cl |
| $CH_2CH_2$ | H | $CH_2CH_2CH_2$ | X/Y-2 | 4,5-Br,Br |
| $CH_2CH(CH_3)$ | H | $CH_2CH_2$ | X/Y-2 | 4,5-Br,Br |
| $CH_2CH_2$ | 3-F | $CH_2CH(CH_3)$ | X/Y-2 | 4,5-Cl,Cl |
| $CH_2$ | H | $CH_2$ | X/Y-15 | — |
| $CH_2$ | H | $CH_2$ | X/Y-15 | 2-CH$_3$ |
| $CH_2$ | H | $CH_2$ | X/Y-15 | 2-Cyclopropyl |
| $CH_2$ | H | $CH_2$ | X/Y-15 | 2-OCH$_2$CH$_3$ |
| $CH_2$ | H | $CH_2$ | X/Y-15 | 2-Cl |
| $CH(CH_3)$ | H | $CH_2$ | X/Y-15 | 2-Cyclopropyl |
| $CH(CH_3)$ | H | $CH_2$ | X/Y-15 | 2-OCH$_2$CH$_3$ |
| $CH_2$ | H | $CH(CH_3)$ | X/Y-15 | 2-Cyclopropyl |
| $CH_2$ | H | $CH(CH_3)$ | X/Y-15 | 2-OCH$_2$CH$_3$ |
| $CH(CH_3)$ | H | $CH(CH_3)$ | X/Y-15 | 2-Cyclopropyl |
| $CH(CH_3)$ | H | $CH(CH_3)$ | X/Y-15 | 2-OCH$_2$CH$_3$ |
| $CH(CH_3)$ | 3-F | $CH(CH_3)$ | X/Y-15 | 2-Cyclopropyl |
| $CH(CH_3)$ | 3-F | $CH(CH_3)$ | X/Y-15 | 2-OCH$_2$CH$_3$ |
| $CH_2CH_2$ | H | $CH_2$ | X/Y-15 | 2-Cyclopropyl |
| $CH_2CH_2$ | H | $CH_2CH_2$ | X/Y-15 | 2-OCH$_2$CH$_3$ |
| $CH_2CH_2CH_2$ | H | $CH_2$ | X/Y-15 | 2-Cyclopropyl |
| $CH_2CH_2$ | H | $CH_2CH_2CH_2$ | X/Y-15 | 2-OCH$_2$CH$_3$ |
| $CH_2CH(CH_3)$ | H | $CH_2CH_2$ | X/Y-15 | 2-Cyclopropyl |
| $CH_2CH_2$ | 3-F | $CH_2CH(CH_3)$ | X/Y-15 | 2-OCH$_2$CH$_3$ |
| $CH_2$ | H | $CH_2$ | X/Y-12 | — |
| $CH_2$ | H | $CH_2$ | X/Y-12 | 2-CH$_3$ |
| $CH_2$ | H | $CH_2$ | X/Y-12 | 2-Cyclopropyl |
| $CH_2$ | H | $CH_2$ | X/Y-12 | 2-OCH$_2$CH$_3$ |
| $CH(CH_3)$ | H | $CH_2$ | X/Y-12 | 2-Cyclopropyl |
| $CH(CH_3)$ | H | $CH_2$ | X/Y-12 | 2-OCH$_2$CH$_3$ |
| $CH_2$ | H | $CH(CH_3)$ | X/Y-12 | 2-Cyclopropyl |
| $CH_2$ | H | $CH(CH_3)$ | X/Y-12 | 2-OCH$_2$CH$_3$ |
| $CH(CH_3)$ | H | $CH(CH_3)$ | X/Y-12 | 2-Cyclopropyl |
| $CH(CH_3)$ | 3-F | $CH(CH_3)$ | X/Y-12 | 2-OCH$_2$CH$_3$ |
| $CH_2CH_2$ | H | $CH_2$ | X/Y-12 | 2-Cyclopropyl |
| $CH_2CH_2$ | H | $CH_2CH_2$ | X/Y-12 | 2-OCH$_2$CH$_3$ |
| $CH_2CH_2CH_2$ | H | $CH_2$ | X/Y-12 | 2-Cyclopropyl |
| $CH_2CH_2$ | H | $CH_2CH_2CH_2$ | X/Y-12 | 2-OCH$_2$CH$_3$ |
| $CH_2CH(CH_3)$ | H | $CH_2CH_2$ | X/Y-12 | 2-Cyclopropyl |
| $CH_2CH_2$ | 3-F | $CH_2CH(CH_3)$ | X/Y-12 | 2-Cyclopropyl |
| $CH_2$ | H | $CH_2$ | X/Y-18 | 1-CH$_3$ |
| $CH_2$ | H | $CH_2$ | X/Y-18 | 1,2-(CH$_3$)$_2$ |
| $CH_2$ | H | $CH_2$ | X/Y-18 | 1,4-(CH$_3$)$_2$ |

TABLE D-continued (for structure I.D)

| A | R¹ | B | Y | Substituent on Y |
|---|---|---|---|---|
| CH₂ | H | CH₂ | X/Y-18 | 1,2,4-(CH₃)₂ |
| CH₂ | H | CH₂ | X/Y-18 | 1-CH₃, 2-Cyclopropyl |
| CH(CH₃) | H | CH₂ | X/Y-18 | 1-CH₃, 2-Cyclopropyl |
| CH(CH₃) | H | CH₂ | X/Y-18 | 1,2,4-(CH₃)₃ |
| CH₂ | H | CH(CH₃) | X/Y-18 | 1-CH₃, 2-Cyclopropyl |
| CH₂ | H | CH(CH₃) | X/Y-18 | 1,2,4-(CH₃)₃ |
| CH(CH₃) | H | CH(CH₃) | X/Y-18 | 1-CH₃, 2-Cyclopropyl |
| CH(CH₃) | 3-F | CH(CH₃) | X/Y-18 | 1,2,4-(CH₃)₃ |
| CH₂CH₂ | H | CH₂ | X/Y-18 | 1-CH₃, 2-Cyclopropyl |
| CH₂CH₂ | H | CH₂CH₂ | X/Y-18 | 1,2,4-(CH₃)₂ |
| CH₂CH₂CH₂ | H | CH₂ | X/Y-18 | 1-CH₃, 2-Cyclopropyl |
| CH₂CH₂ | H | CH₂CH₂CH₂ | X/Y-18 | 1,2,4-(CH₃)₂ |
| CH₂CH(CH₃) | H | CH₂CH₂ | X/Y-18 | 1-CH₃, 2-Cyclopropyl |
| CH₂CH₂ | 3-F | CH₂CH(CH₃) | X/Y-18 | 1,2,4-(CH₃)₂ |
| CH₂ | H | CH₂ | X/Y-19 | 1-CH₃ |
| CH₂ | H | CH₂ | X/Y-19 | 1,2-(CH₃)₂ |
| CH₂ | H | CH₂ | X/Y-19 | 1,5-(CH₃)₂ |
| CH₂ | H | CH₂ | X/Y-19 | 1-CH₃, 2-Cyclopropyl |
| CH(CH₃) | H | CH₂ | X/Y-19 | 1,2-(CH₃)₂ |
| CH(CH₃) | H | CH₂ | X/Y-19 | 1-CH₃, 2-Cyclopropyl |
| CH₂ | H | CH(CH₃) | X/Y-19 | 1,2-(CH₃)₂ |
| CH₂ | H | CH(CH₃) | X/Y-19 | 1-CH₃, 2-Cyclopropyl |
| CH(CH₃) | H | CH(CH₃) | X/Y-19 | 1,2-(CH₃)₂ |
| CH(CH₃) | H | CH(CH₃) | X/Y-19 | 1-CH₃, 2-Cyclopropyl |
| CH(CH₃) | 3-F | CH₂ | X/Y-19 | 1-CH₃, 2-Cyclopropyl |
| CH₂CH₂ | H | CH₂ | X/Y-19 | 1-CH₃, 2-Cyclopropyl |
| CH₂CH₂ | H | CH₂CH₂ | X/Y-19 | 1,2-(CH₃)₂ |
| CH₂CH₂CH₂ | H | CH₂ | X/Y-19 | 1-CH₃, 2-Cyclopropyl |
| CH₂CH₂ | H | CH₂CH₂CH₂ | X/Y-19 | 1,2-(CH₃)₂ |
| CH₂CH(CH₃) | H | CH₂CH₂ | X/Y-19 | 1-CH₃, 2-Cyclopropyl |
| CH₂CH₂ | 3-F | CH₂CH(CH₃) | X/Y-19 | 1,2-(CH₃)₂ |
| CH₂ | H | CH₂ | X/Y-16 | — |
| CH₂ | H | CH₂ | X/Y-16 | 2-CH₃ |
| CH₂ | H | CH₂ | X/Y-16 | 2-Cyclopropyl |
| CH₂ | H | CH₂ | X/Y-16 | 2-Cl |
| CH₂ | H | CH₂ | X/Y-16 | 2-OCH₂CH₃ |
| CH(CH₃) | H | CH₂ | X/Y-16 | 2-CH₃ |
| CH(CH₃) | H | CH₂ | X/Y-16 | 2-Cyclopropyl |
| CH₂ | H | CH(CH₃) | X/Y-16 | 2-CH₃ |
| CH₂ | H | CH(CH₃) | X/Y-16 | 2-Cyclopropyl |
| CH₂(CH₃) | H | CH(CH₃) | X/Y-16 | 2-CH₃ |
| CH₂(CH₃) | H | CH(CH₃) | X/Y-16 | 2-Cyclopropyl |
| CH₂(CH₃) | 3-F | CH(CH₃) | X/Y-16 | 2-Cyclopropyl |
| CH₂CH₂ | H | CH₂ | X/Y-16 | 2-Cyclopropyl |
| CH₂CH₂ | H | CH₂CH₂ | X/Y-16 | 2-CH₃ |
| CH₂CH₂CH₂ | H | CH₂ | X/Y-16 | 2-Cyclopropyl |
| CH₂CH₂ | H | CH₂CH₂CH₂ | X/Y-16 | 2-CH₃ |
| CH₂CH(CH₃) | H | CH₂CH₂ | X/Y-16 | 2-Cyclopropryl |
| CH₂CH₂ | 3-F | CH₂CH(CH₃) | X/Y-16 | 2-CH₃ |
| CH₂ | H | CH₂ | X/Y-13 | — |
| CH₂ | H | CH₂ | X/Y-13 | 2-CH₃ |
| CH₂ | H | CH₂ | X/Y-13 | 2-Cyclopropyl |
| CH₂ | H | CH₂ | X/Y-13 | 2-OCH₂CH₃ |
| CH(CH₃) | H | CH₂ | X/Y-13 | 2-OCH₂CH₃ |
| CH(CH₃) | H | CH₂ | X/Y-13 | 2-Cyclopropyl |
| CH₂ | H | CH(CH₃) | X/Y-13 | 2-OCH₂CH₃ |
| CH₂ | H | CH(CH₃) | X/Y-13 | 2-Cyclopropyl |
| CH(CH₃) | H | CH(CH₃) | X/Y-13 | 2-OCH₂CH₃ |
| CH(CH₃) | 3-F | CH(CH₃) | X/Y-13 | 2-Cyclopropyl |
| CH₂CH₂ | H | CH₂ | X/Y-13 | 2-Cyclopropyl |
| CH₂CH₂ | H | CH₂CH₂ | X/Y-13 | 2-CH₃ |
| CH₂CH₂CH₂ | H | CH₂ | X/Y-13 | 2-Cyclopropyl |
| CH₂CH₂ | H | CH₂CH₂CH₂ | X/Y-13 | 2-CH₃ |
| CH(CH₃)CH₂ | 3-F | CH₂CH₂ | X/Y-13 | 2-Cyclopropyl |
| CH₂CH₂ | H | CH(CH₃)CH₂ | X/Y-13 | 2-CH₃ |
| CH₂ | H | CH₂ | X/Y-6 | — |
| CH₂ | H | CH₂ | X/Y-6 | 3-CH₃ |
| CH₂ | H | CH₂ | X/Y-6 | 3-Cyclopropyl |
| CH₂ | H | CH₂ | X/Y-6 | 3-OCH₂CH₃ |
| CH(CH₃) | H | CH(CH₃) | X/Y-6 | 3-Cyclopropyl |
| CH(CH₃) | 3-F | CH(CH₃) | X/Y-6 | 3-Cyclopropyl |
| CH₂CH₂ | H | CH₂CH₂ | X/Y-6 | 3-Cyclopropyl |
| CH₂CH₂ | H | CH₂CH₂CH₂ | X/Y-6 | 3-CH₃ |
| CH(CH₃)CH₂ | 3-F | CH₂CH₂ | X/Y-6 | 3-Cyclopropyl |
| CH₂CH₂ | H | CH(CH₃)CH₂ | X/Y-6 | 3-Cyclopropyl |
| CH₂ | H | CH₂ | X/Y-8 | 1-CH₃ |
| CH₂ | H | CH₂ | X/Y-8 | 1,3-(CH₃)₂ |
| CH₂ | H | CH₂ | X/Y-8 | 1,4-(CH₃)₂ |
| CH₂ | H | CH₂ | X/Y-8 | 1-CH₃, 3-Cyclopropyl |
| CH(CH₃) | H | CH(CH₃) | X/Y-8 | 1-CH₃, 3-Cyclopropyl |

TABLE D-continued (for structure I.D)

| A | R¹ | B | Y | Substituent on Y |
|---|---|---|---|---|
| CH(CH₃) | 3-F | CH(CH₃) | X/Y-8 | 1-CH₃, 3-Cyclopropyl |
| CH₂CH₂ | H | CH₂CH₂ | X/Y-8 | 1-CH₃, 3-Cyclopropyl |
| CH₂CH₂ | H | CH₂CH₂CH₂ | X/Y-8 | 1,3-(CH₃)₂ |
| CH₂CH(CH₃) | H | CH₂CH₂ | X/Y-8 | 1-CH₃, 3-Cyclopropyl |
| CH(CH₃)CH₂ | 3-F | CH₂CH₂ | X/Y-8 | 1-CH₃, 3-Cyclopropyl |
| CH₂ | H | CH₂ | X/Y-10 | 1-CH₃ |
| CH₂ | H | CH₂ | X/Y-10 | 1,4-(CH₃)₂ |
| CH₂ | H | CH₂ | X/Y-10 | 1-CH₃, 4-OCH₃ |
| CH₂ | H | CH₂ | X/Y-10 | 1-CH₃, 5-CH(CH₃)₂ |
| CH₂ | H | CH₂ | X/Y-10 | 1-CH₃, 5-Cyclopropyl |
| CH(CH₃) | H | CH(CH₃) | X/Y-10 | 1-CH₃, 5-Cyclopropyl |
| CH(CH₃) | 3-F | CH(CH₃) | X/Y-10 | 1,4-(CH₃)₂ |
| CH₂CH₂ | H | CH₂CH₂ | X/Y-10 | 1-CH₃, 5-Cyclopropyl |
| CH₂CH₂ | H | CH₂CH₂CH₂ | X/Y-10 | 1,5-(CH₃)₂ |
| CH₂CH(CH₃) | H | CH₂CH₂ | X/Y-10 | 1-CH₃, 5-Cyclopropyl |
| CH(CH₃)CH₂ | 3-F | CH₂CH₂ | X/Y-10 | 1-CH₃, 5-Cyclopropyl |
| CH₂ | H | CH₂ | X/Y-7 | — |
| CH₂ | H | CH₂ | X/Y-7 | 3-CH₃ |
| CH(CH₃) | H | CH(CH₃) | X/Y-7 | 3-CH₃ |
| CH(CH₃) | 3-F | CH(CH₃) | X/Y-7 | 3-CH₃ |
| CH₂CH₂ | H | CH₂CH₂ | X/Y-7 | 3-CH₃ |
| CH₂CH₂ | 3-F | CH(CH₃)CH₂CH₂ | X/Y-7 | 3-CH₃ |
| CH₂ | H | CH₂ | X/Y-9 | 1-CH₃ |
| CH₂ | H | CH₂ | X/Y-9 | 1,3-(CH₃)₂ |
| CH₂ | H | CH₂ | X/Y-9 | 1,5-(CH₃)₂ |
| CH(CH₃) | H | CH(CH₃) | X/Y-9 | 1,3-(CH₃)₂ |
| CH(CH₃) | 3-F | CH(CH₃) | X/Y-9 | 1,5-(CH₃)₂ |
| CH₂CH₂ | H | CH₂CH₂ | X/Y-9 | 1,3-(CH₃)₂ |
| CH₂CH₂ | H | CH₂CH₂CH₂ | X/Y-9 | 1,5-(CH₃)₂ |
| CH₂CH(CH₃) | H | CH₂CH₂ | X/Y-9 | 1,3-(CH₃)₂ |
| CH(CH₃)CH₂ | 3-F | CH₂CH₂ | X/Y-9 | 1,5-(CH₃)₂ |
| CH₂ | H | CH₂ | X/Y-25 | 5-CH₃ |
| CH₂ | H | CH₂ | X/Y-25 | 5-CH₂CH₃ |
| CH₂ | H | CH₂ | X/Y-25 | 5-CH(CH₃)₂ |
| CH₂ | H | CH₂ | X/Y-25 | 5-OCH₃ |
| CH(CH₃) | H | CH(CH₃) | X/Y-25 | 5-Cyclopropyl |
| CH₂(CH₃) | H | CH(CH₃) | X/Y-25 | 5-CH₃ |
| CH(CH₃) | H | CH(CH₃) | X/Y-25 | 5-OCH₂CH₃ |
| CH(CH₃) | 3-F | CH(CH₃) | X/Y-25 | 5-Cyclopropyl |
| CH₂CH₂ | H | CH₂ | X/Y-25 | 5-Cyclopropyl |
| CH₂CH₂ | H | CH₂CH₂ | X/Y-25 | 5-CH₃ |
| CH₂CH₂CH₂ | H | CH₂ | X/Y-25 | 5-OCH₂CH₃ |
| CH₂CH₂ | 3-F | CH₂CH(CH₃) | X/Y-25 | 5-Cyclopropyl |
| CH₂ | H | CH(CH₃) | X/Y-25 | 5-Cyclopropyl |
| CH₂ | H | CH₂ | X/Y-23 | — |
| CH₂ | H | CH₂ | X/Y-23 | 5-Cyclopropyl |
| CH₂ | H | CH₂ | X/Y-23 | 5-CH₃ |
| CH₂ | H | CH₂ | X/Y-23 | 5-CH(CH₃)₂ |
| CH₂ | H | CH₂ | X/Y-23 | 5-Cl |
| CH₂ | H | CH₂ | X/Y-23 | 5-OCH₂CH₃ |
| CH₂ | H | CH(CH₃) | X/Y-23 | 5-Cyclopropyl |
| CH₂ | 3-F | CH(CH₃) | X/Y-23 | 5-CH₃ |
| CH₂ | H | CH(CH₃) | X/Y-23 | 5-CH(CH₃)₂ |
| CH(CH₃) | H | CH(CH₃) | X/Y-23 | 5-Cyclopropyl |
| CH₂ | H | CH₂CH₂ | X/Y-23 | 5-Cyclopropyl |
| CH₂CH₂CH₂ | H | CH₂ | X/Y-23 | 5-CH₃ |
| CH₂CH₂ | H | CH₂CH₂ | X/Y-23 | 5-CH(CH₃)₂ |
| CH₂CH₂ | H | CH₂CH₂ | X/Y-23 | 5-Cyclopropyl |
| CH₂ | H | CH₂ | X/Y-26 | 1-CH₃ |
| CH₂ | H | CH₂ | X/Y-26 | 1,5-(CH₃)₂ |
| CH₂ | H | CH₂ | X/Y-26 | 1-CH₃, 5-Cyclopropyl |
| CH(CH₃) | H | CH(CH₃) | X/Y-26 | 1-CH₃, 5-Cyclopropyl |
| CH(CH₃) | H | CH(CH₃) | X/Y-26 | 1,5-(CH₃)₂ |
| CH(CH₃) | 3-F | CH₂ | X/Y-26 | 1-CH₃, 5-Cyclopropyl |
| CH₂CH₂ | H | CH₂CH₂ | X/Y-26 | 1-CH₃, 5-Cyclopropyl |
| CH₂ | H | CH₂CH₂ | X/Y-26 | 1,5-(CH₃)₂ |
| CH₂ | H | CH₂ | X/Y-28 | 1-CH₃ |
| CH₂ | H | CH₂ | X/Y-28 | 1,5-(CH₃)₂ |
| CH₂ | H | CH₂ | X/Y-28 | 1-CH₃, 5-Cyclopropyl |
| CH(CH₃) | H | CH(CH₃) | X/Y-28 | 1-CH₃, 5-Cyclopropyl |
| CH(CH₃) | H | CH(CH₃) | X/Y-28 | 1,5-(CH₃)₂ |
| CH(CH₃) | 3-F | CH₂ | X/Y-28 | 1-CH₃, 5-Cyclopropyl |
| CH₂CH₂ | H | CH₂CH₂ | X/Y-28 | 1-CH₃, 5-Cyclopropyl |
| CH₂ | H | CH₂CH₂ | X/Y-28 | 1,5-(CH₃)₂ |
| CH₂ | H | CH₂ | X/Y-22 | — |
| CH₂ | H | CH₂ | X/Y-22 | 3-CH₃ |
| CH₂ | H | CH₂ | X/Y-22 | 3-Cyclopropyl |
| CH₂ | H | CH₂ | X/Y-22 | 3-OCH₃ |
| CH(CH₃) | H | CH₂ | X/Y-22 | 3-CH₃ |
| CH₂ | H | CH(CH₃) | X/Y-22 | 3-Cyclopropyl |

TABLE D-continued

(for structure I.D)

| A | R¹ | B | Y | Substituent on Y |
|---|---|---|---|---|
| CH₂ | 3-F | CH(CH₃) | X/Y-22 | 3-OCH₃ |
| CH₂CH₂ | H | CH₂CH₂ | X/Y-22 | 3-Cyclopropyl |
| CH₂ | H | CH₂CH₂ | X/Y-22 | 3-CH₃ |
| CH₂ | H | CH₂ | X/Y-29 | 1-CH₃ |
| CH₂ | H | CH₂ | X/Y-29 | 1,3-(CH₃)₂ |
| CH₂ | H | CH₂ | X/Y-29 | 1-CH₃, 3-Cyclopropyl |
| CH(CH₃) | H | CH(CH₃) | X/Y-29 | 1,3-(CH₃)₂ |
| CH(CH₃) | 3-F | CH(CH₃) | X/Y-29 | 1-CH₃, 3-Cyclopropyl |
| CH₂CH₂ | H | CH₂CH₂CH₂ | X/Y-29 | 1,3-(CH₃)₂ |
| CH₂CH₂ | H | CH₂CH₂ | X/Y-29 | 1-CH₃, 3-Cyclopropyl |
| CH₂ | H | CH₂ | X/Y-17 | — |
| CH₂ | H | CH₂ | X/Y-17 | 5-Cyclopropyl |
| CH₂ | H | CH₂ | X/Y-17 | 5-CH₃ |
| CH₂ | H | CH₂ | X/Y-17 | 5-OCH₂CH₃ |
| CH₂ | H | CH₂ | X/Y-17 | 5-Cl |
| CH₂ | H | CH₂ | X/Y-17 | 4-CH₃ |
| CH₂ | H | CH₂ | X/Y-17 | 4-Cyclopropyl |
| CH₂ | H | CH₂ | X/Y-17 | 4-OCH₂CH₃ |
| CH₂ | H | CH₂ | X/Y-17 | 4-Cl |
| CH(CH₃) | H | CH(CH₃) | X/Y-17 | 5-Cyclopropyl |
| CH(CH₃) | H | CH(CH₃) | X/Y-17 | 4-Cyclopropyl |
| CH(CH₃) | 3-F | CH(CH₃) | X/Y-17 | 5-OCH₂CH₃ |
| CH₂CH₂ | H | CH₂CH₂ | X/Y-17 | 5-Cyclopropyl |
| CH₂CH₂ | H | CH₂CH₂ | X/Y-17 | 4-Cyclopropyl |
| CH₂CH₂ | H | CH₂CH₂CH₂ | X/Y-17 | 5-CH₃ |
| CH₂ | H | CH₂ | X/Y-14 | — |
| CH₂ | H | CH₂ | X/Y-14 | 5-CH₃ |
| CH₂ | H | CH₂ | X/Y-14 | 5-Cyclopropyl |
| CH₂ | H | CH₂ | X/Y-14 | 4-CH₃ |
| CH₂ | H | CH₂ | X/Y-14 | 4-Cyclopropyl |
| CH₂ | H | CH₂ | X/Y-14 | 4-OCH₂CH₃ |
| CH₂ | H | CH₂ | X/Y-14 | 5-OCH₂CH₃ |
| CH₂ | H | CH₂ | X/Y-14 | 5-Cl |
| CH(CH₃) | H | CH(CH₃) | X/Y-14 | 4-Cyclopropyl |
| CH(CH₃) | H | CH(CH₃) | X/Y-14 | 5-Cyclopropyl |
| CH(CH₃) | H | CH(CH₃) | X/Y-14 | 4-CH₃ |
| CH(CH₃) | 3-F | CH(CH₃) | X/Y-14 | 4-Cyclopropyl |
| CH₂ | 3-F | CH₂ | X/Y-14 | 5-OCH₂CH₃ |
| CH₂CH₂ | H | CH₂CH₂ | X/Y-14 | 4-Cyclopropyl |
| CH₂CH₂ | H | CH₂CH₂ | X/Y-14 | 5-Cyclopropyl |
| CH₂CH₂ | H | CH₂CH₂CH₂ | X/Y-14 | 5-Cl |
| CH₂CH₂ | H | CH₂CH₂ | X/Y-14 | 4-CH₃ |
| CH₂ | H | CH₂ | X/Y-20 | 1-CH₃ |
| CH₂ | H | CH₂ | X/Y-20 | 1,5-(CH₃)₂ |
| CH(CH₃) | H | CH(CH₃) | X/Y-20 | 1-CH₃ |
| CH(CH₃) | 3-F | CH(CH₃) | X/Y-20 | 1,5-(CH₃)₂ |
| CH₂CH₂ | H | CH₂CH₂ | X/Y-20 | 1-CH₃ |
| CH₂CH₂ | H | CH₂CH₂ | X/Y-20 | 1,5-(CH₃)₂ |
| CH(CH₃)CH₂ | 3-F | CH(CH₃)CH₂ | X/Y-20 | 1,5-(CH₃)₂ |
| CH₂ | H | CH₂ | X/Y-3 | — |
| CH₂ | H | CH₂ | X/Y-3 | 3-CH₃ |
| CH₂ | H | CH₂ | X/Y-3 | 3-CH₂CH₃ |
| CH₂ | H | CH₂ | X/Y-3 | 3-CH(CH₃)₂ |
| CH₂ | H | CH₂ | X/Y-3 | 3-OCH₂CH₃ |
| CH₂ | H | CH₂ | X/Y-3 | 3-CH₂OCH₃ |
| CH₂ | H | CH₂ | X/Y-3 | 3-CF₃ |
| CH(CH₃) | H | CH₂ | X/Y-3 | 3-CH₃ |
| CH(CH₃) | H | CH₂ | X/Y-3 | 3-CH(CH₃)₂ |
| CH(CH₃) | H | CH₂ | X/Y-3 | 3-Cyclopropyl |
| CH₂ | H | CH(CH₃) | X/Y-3 | 3-CH₃ |
| CH₂ | H | CH(CH₃) | X/Y-3 | 3-CH(CH₃)₂ |
| CH₂ | H | CH(CH₃) | X/Y-3 | 3-Cyclopropyl |
| CH(CH₃) | H | CH(CH₃) | X/Y-3 | 3-CH₃ |
| CH(CH₃) | 3-F | CH(CH₃) | X/Y-3 | 3-CH(CH₃)₂ |
| CH(CH₃) | H | CH(CH₃) | X/Y-3 | 3-Cyclopropyl |
| CH₂ | H | CH₂CH₂ | X/Y-3 | 3-CH₃ |
| CH₂CH₂ | H | CH₂CH₂CH₂ | X/Y-3 | 3-CH(CH₃)₂ |
| CH₂ | H | CH₂CH₂ | X/Y-3 | 3-Cyclopropyl |
| CH₂CH₂ | H | CH₂CH(CH₃) | X/Y-3 | 3-Cyclopropyl |
| CH₂CH₂ | H | CH₂CH(CH₃) | X/Y-3 | 3-CH(CH₃)₂ |
| CH₂CH₂CH₂ | 3-F | CH(CH₃)CH₂ | X/Y-3 | 3-CH₃ |
| CH₂ | H | CH₂ | X/Y-5 | — |
| CH₂ | H | CH₂ | X/Y-5 | 5-OCH₂CH₃ |
| CH₂ | H | CH₂ | X/Y-5 | 5-Cyclopropyl |
| CH₂ | H | CH₂ | X/Y-5 | 5-CH₃ |
| CH(CH₃) | 3-F | CH(CH₃) | X/Y-5 | 5-CH₃ |
| CH₂ | H | CH(CH₃) | X/Y-5 | 5-Cyclopropyl |
| CH(CH₃) | H | CH₂ | X/Y-5 | 5-Cyclopropyl |
| CH₂ | H | CH₂CH₂ | X/Y-5 | 5-OCH₂CH₃ |
| CH₂CH₂ | H | CH₂CH₂CH₂ | X/Y-5 | 5-CH₃ |

TABLE D-continued (for structure I.D)

| A | R¹ | B | Y | Substituent on Y |
|---|---|---|---|---|
| CH₂ | H | CH₂ | X/Y-4 | — |
| CH₂ | H | CH₂ | X/Y-4 | 3-OCH₂CH₃ |
| CH₂ | H | CH₂ | X/Y-4 | 5-OCH₂CH₃ |
| CH₂ | H | CH₂ | X/Y-4 | 3-CH(CH₃)₂ |
| CH₂ | H | CH₂ | X/Y-4 | 5-CH₃ |
| CH(CH₃) | 3-F | CH(CH₃) | X/Y-4 | 3-CH(CH₃)₂ |
| CH₂ | H | CH₂ | X/Y-11 | — |
| CH₂ | H | CH₂ | X/Y-11 | 3-CH₃ |
| CH₂ | H | CH₂ | X/Y-11 | 5-CH₃ |
| CH₂ | H | CH(CH₃) | X/Y-11 | 3-CH₃ |
| CH₂ | 3-F | CH(CH₃) | X/Y-11 | 5-CH₃ |
| CH(CH₃) | H | CH(CH₃) | X/Y-11 | 5-CH₃ |
| CH₂ | H | CH₂ | X/Y-21 | — |
| CH₂ | H | CH₂ | X/Y-21 | 4,5-(CH₃)₂ |
| CH₂ | H | CH₂ | X/Y-21 | 4,5-Br₂ |
| CH(CH₃) | H | CH(CH₃) | X/Y-21 | 4,5-Cl₂ |
| CH(CH₃) | H | CH(CH₃) | X/Y-21 | 4,5-(CH₃)₂ |
| CH(CH₃) | H | CH(CH₃) | X/Y-21 | 4,5-Br₂ |
| CH₂ | H | CH₂ | X/Y-30 | — |
| CH₂ | H | CH₂ | X/Y-30 | 3,5-(CH₃)₂ |
| CH(CH₃) | H | CH(CH₃) | X/Y-30 | — |
| CH(CH₃) | H | CH(CH₃) | X/Y-30 | 3,5-(CH₃)₂ |
| CH₂ | H | CH₂ | X/Y-27 | — |
| CH₂ | H | CH₂ | X/Y-27 | 2-Cl |
| CH₂ | H | CH₂ | X/Y-27 | 2,5-(CH₃)₂ |
| CH(CH₃) | H | CH(CH₃) | X/Y-27 | — |
| CH(CH₃) | H | CH(CH₃) | X/Y-27 | 2-Cl |
| CH(CH₃) | H | CH(CH₃) | X/Y-27 | 2,5-(CH₃)₂ |

TABLE E (for structure I.E)

| A | R¹ | B | Y | Substituent on Y |
|---|---|---|---|---|
| CH₂ | H | CH₂ | X/Y-1 | |
| CH(CH₃) | H | CH₂ | X/Y-1 | |
| CH(CH₂CH₃) | H | CH₂ | X/Y-1 | |
| CH₂ | H | CH(CH₃) | X/Y-1 | |
| CH₂ | H | CH(CH₂CH₃) | X/Y-1 | |
| CH₂ | 3-CH₃ | CH₂ | X/Y-1 | |
| CH₂ | 3-F | CH₂ | X/Y-1 | |
| CH₂ | H | CH₂ | X/Y-1 | 5-CH₃ |
| CH₂ | H | CH₂ | X/Y-1 | 4-CH₃ |
| CH₂ | H | CH₂ | X/Y-1 | 3-CH₃ |
| CH₂ | H | CH₂ | X/Y-1 | 5-Cyclopropyl |
| CH₂ | H | CH₂ | X/Y-1 | 4-Cyclopropyl |
| CH₂ | H | CH₂ | X/Y-1 | 3-Cyclopropyl |
| CH₂ | H | CH₂ | X/Y-1 | 5-Cl |
| CH₂ | H | CH₂ | X/Y-1 | 5-Br |
| CH₂ | H | CH₂ | X/Y-1 | 4-Cl |
| CH₂ | H | CH₂ | X/Y-1 | 4-Br |
| CH₂ | H | CH₂ | X/Y-1 | 4,5-Cl,Cl |
| CH₂ | H | CH₂ | X/Y-1 | 4-OCH₂CH₃ |
| CH(CH₃) | H | CH₂ | X/Y-1 | 5-Br |
| CH(CH₃) | H | CH₂ | X/Y-1 | 4,5-Cl,Cl |
| CH(CH₃) | H | CH₂ | X/Y-1 | 4-Cl |
| CH₂ | H | CH(CH₃) | X/Y-1 | 5-Br |
| CH₂ | H | CH(CH₃) | X/Y-1 | 4,5-Cl,Cl |
| CH(CH₃) | H | CH(CH₃) | X/Y-1 | — |
| CH(CH₃) | H | CH(CH₃) | X/Y-1 | 4,5-Cl,Cl |
| CH(CH₃) | 3-F | CH(CH₃) | X/Y-1 | — |
| CH(CH₃) | 3-F | CH(CH₃) | X/Y-1 | 5-Br |
| CH₂CH₂ | H | CH₂ | X/Y-1 | 5-Br |
| CH₂CH₂ | H | CH₂CH₂ | X/Y-1 | 4,5-Cl,Cl |
| CH₂CH₂CH₂ | H | CH₂ | X/Y-1 | 5-Br |
| CH₂CH₂ | H | CH₂CH₂CH₂ | X/Y-1 | 4,5-Cl,Cl |
| CH₂CH(CH₃) | H | CH₂CH₂ | X/Y-1 | 4,5-Cl,Cl |
| CH₂CH₂ | 3-F | CH₂CH(CH₃) | X/Y-1 | 5-Br |
| CH₂ | H | CH₂ | X/Y-2 | — |
| CH₂ | H | CH₂ | X/Y-2 | 4-Cyclopropyl |
| CH₂ | H | CH₂ | X/Y-2 | 5-Cyclopropyl |
| CH₂ | H | CH₂ | X/Y-2 | 5-Cl |
| CH₂ | H | CH₂ | X/Y-2 | 4,5-Cl,Cl |
| CH₂ | H | CH₂ | X/Y-2 | 4,5-Br,Br |
| CH₂ | H | CH₂ | X/Y-2 | 4-CH₃ |
| CH₂ | H | CH₂ | X/Y-2 | 5-CH₃ |
| CH₂ | H | CH₂ | X/Y-2 | 4-OCH₃ |
| CH₂ | H | CH₂ | X/Y-2 | 5-OCH₃ |
| CH(CH₃) | H | CH₂ | X/Y-2 | 4,5-Cl,Cl |

TABLE E-continued (for structure I.E)

| A | R¹ | B | Y | Substituent on Y |
|---|---|---|---|---|
| CH(CH₃) | H | CH₂ | X/Y-2 | 4,5-Br,Br |
| CH₂ | H | CH(CH₃) | X/Y-2 | 4,5-Cl,Cl |
| CH₂ | H | CH(CH₃) | X/Y-2 | 4,5-Br,Br |
| CH(CH₃) | H | CH(CH₃) | X/Y-2 | 4,5-Cl,Cl |
| CH(CH₃) | H | CH(CH₃) | X/Y-2 | 4,5-Br,Br |
| CH(CH₃) | 3-F | CH(CH₃) | X/Y-2 | 4,5-Cl,Cl |
| CH(CH₃) | 3-F | CH(CH₃) | X/Y-2 | 4,5-Br,Br |
| CH₂CH₂ | H | CH₂ | X/Y-2 | 4,5-Cl,Cl |
| CH₂CH₂ | H | CH₂CH₂ | X/Y-2 | 4,5-Br,Br |
| CH₂CH₂CH₂ | H | CH₂ | X/Y-2 | 4,5-Cl,Cl |
| CH₂CH₂ | H | CH₂CH₂CH₂ | X/Y-2 | 4,5-Br,Br |
| CH₂CH(CH₃) | H | CH₂CH₂ | X/Y-2 | 4,5-Br, Br |
| CH₂CH₂ | 3-F | CH₂CH(CH₃) | X/Y-2 | 4,5-Cl,Cl |
| CH₂ | H | CH₂ | X/Y-15 | — |
| CH₂ | H | CH₂ | X/Y-15 | 2-CH₃ |
| CH₂ | H | CH₂ | X/Y-15 | 2-Cyclopropyl |
| CH₂ | H | CH₂ | X/Y-15 | 2-OCH₂CH₃ |
| CH₂ | H | CH₂ | X/Y-15 | 2-Cl |
| CH(CH₃) | H | CH₂ | X/Y-15 | 2-Cyclopropyl |
| CH(CH₃) | H | CH₂ | X/Y-15 | 2-OCH₂CH₃ |
| CH₂ | H | CH(CH₃) | X/Y-15 | 2-Cyclopropyl |
| CH₂ | H | CH(CH₃) | X/Y-15 | 2-OCH₂CH₃ |
| CH(CH₃) | H | CH(CH₃) | X/Y-15 | 2-Cyclopropyl |
| CH(CH₃) | H | CH(CH₃) | X/Y-15 | 2-OCH₂CH₃ |
| CH(CH₃) | 3-F | CH(CH₃) | X/Y-15 | 2-Cyclopropyl |
| CH(CH₃) | 3-F | CH(CH₃) | X/Y-15 | 2-OCH₂CH₃ |
| CH₂CH₂ | H | CH₂ | X/Y-15 | 2-Cyclopropyl |
| CH₂CH₂ | H | CH₂CH₂ | X/Y-15 | 2-OCH₂CH₃ |
| CH₂CH₂CH₂ | H | CH₂ | X/Y-15 | 2-Cyclopropyl |
| CH₂CH₂ | H | CH₂CH₂CH₂ | X/Y-15 | 2-OCH₂CH₃ |
| CH₂CH(CH₃) | H | CH₂CH₂ | X/Y-15 | 2-Cyclopropyl |
| CH₂CH₂ | 3-F | CH₂CH(CH₃) | X/Y-15 | 2-OCH₂CH₃ |
| CH₂ | H | CH₂ | X/Y-12 | — |
| CH₂ | H | CH₂ | X/Y-12 | 2-CH₃ |
| CH₂ | H | CH₂ | X/Y-12 | 2-Cyclopropyl |
| CH₂ | H | CH₂ | X/Y-12 | 2-OCH₂CH₃ |
| CH(CH₃) | H | CH₂ | X/Y-12 | 2-Cyclopropyl |
| CH(CH₃) | H | CH₂ | X/Y-12 | 2-OCH₂CH₃ |
| CH₂ | H | CH(CH₃) | X/Y-12 | 2-Cyclopropyl |
| CH₂ | H | CH(CH₃) | X/Y-12 | 2-OCH₂CH₃ |
| CH(CH₃) | H | CH(CH₃) | X/Y-12 | 2-Cyclopropyl |
| CH(CH₃) | 3-F | CH(CH₃) | X/Y-12 | 2-OCH₂CH₃ |
| CH₂CH₂ | H | CH₂ | X/Y-12 | 2-Cyclopropyl |
| CH₂CH₂ | H | CH₂CH₂ | X/Y-12 | 2-OCH₂CH₃ |
| CH₂CH₂CH₂ | H | CH₂ | X/Y-12 | 2-Cyclopropyl |
| CH₂CH₂ | H | CH₂CH₂CH₂ | X/Y-12 | 2-OCH₂CH₃ |
| CH₂CH(CH₃) | H | CH₂CH₂ | X/Y-12 | 2-Cyclopropyl |
| CH₂CH₂ | 3-F | CH₂CH(CH₃) | X/Y-12 | 2-Cyclopropyl |
| CH₂ | H | CH₂ | X/Y-18 | 1-CH₃ |
| CH₂ | H | CH₂ | X/Y-18 | 1,2-(CH₃)₂ |
| CH₂ | H | CH₂ | X/Y-18 | 1,4-(CH₃)₂ |
| CH₂ | H | CH₂ | X/Y-18 | 1,2,4-(CH₃)₂ |
| CH₂ | H | CH₂ | X/Y-18 | 1-CH₃, 2-Cyclopropyl |
| CH(CH₃) | H | CH₂ | X/Y-18 | 1-CH₃, 2-Cyclopropyl |
| CH(CH₃) | H | CH₂ | X/Y-18 | 1,2,4-(CH₃)₃ |
| CH₂ | H | CH(CH₃) | X/Y-18 | 1-CH₃, 2-Cyclopropyl |
| CH₂ | H | CH(CH₃) | X/Y-18 | 1,2,4-(CH₃)₃ |
| CH(CH₃) | H | CH(CH₃) | X/Y-18 | 1-CH₃, 2-Cyclopropyl |
| CH(CH₃) | 3-F | CH(CH₃) | X/Y-18 | 1,2,4-(CH₃)₃ |
| CH₂CH₂ | H | CH₂ | X/Y-18 | 1-CH₃, 2-Cyclopropyl |
| CH₂CH₂ | H | CH₂CH₂ | X/Y-18 | 1,2,4-(CH₃)₂ |
| CH₂CH₂CH₂ | H | CH₂ | X/Y-18 | 1-CH₃, 2-Cyclopropyl |
| CH₂CH₂ | H | CH₂CH₂CH₂ | X/Y-18 | 1,2,4-(CH₃)₂ |
| CH₂CH(CH₃) | H | CH₂CH₂ | X/Y-18 | 1-CH₃, 2-Cyclopropyl |
| CH₂CH₂ | 3-F | CH₂CH(CH₃) | X/Y-18 | 1,2,4-(CH₃)₂ |
| CH₂ | H | CH₂ | X/Y-19 | 1-CH₃ |
| CH₂ | H | CH₂ | X/Y-19 | 1,2-(CH₃)₂ |
| CH₂ | H | CH₂ | X/Y-19 | 1,5-(CH₃)₂ |
| CH(CH₃) | H | CH₂ | X/Y-19 | 1,2-(CH₃)₂ |
| CH(CH₃) | H | CH₂ | X/Y-19 | 1-CH₃, 2-Cyclopropyl |
| CH₂ | H | CH(CH₃) | X/Y-19 | 1,2-(CH₃)₂ |
| CH₂ | H | CH(CH₃) | X/Y-19 | 1-CH₃, 2-Cyclopropyl |
| CH(CH₃) | H | CH(CH₃) | X/Y-19 | 1,2-(CH₃)₂ |
| CH(CH₃) | H | CH(CH₃) | X/Y-19 | 1-CH₃, 2-Cyclopropyl |
| CH(CH₃) | 3-F | CH₂ | X/Y-19 | 1-CH₃, 2-Cyclopropyl |
| CH₂CH₂ | H | CH₂ | X/Y-19 | 1-CH₃, 2-Cyclopropyl |
| CH₂CH₂ | H | CH₂CH₂ | X/Y-19 | 1,2-(CH₃)₂ |
| CH₂CH₂CH₂ | H | CH₂ | X/Y-19 | 1-CH₃, 2-Cyclopropyl |
| CH₂CH₂ | H | CH₂CH₂CH₂ | X/Y-19 | 1,2-(CH₃)₂ |

TABLE E-continued (for structure I.E)

| A | R¹ | B | Y | Substituent on Y |
|---|---|---|---|---|
| CH₂CH(CH₃) | H | CH₂CH₂ | X/Y-19 | 1-CH₃, 2-Cyclopropyl |
| CH₂CH₂ | 3-F | CH₂CH(CH₃) | X/Y-19 | 1,2-(CH₃)₂ |
| CH₂ | H | CH₂ | X/Y-16 | — |
| CH₂ | H | CH₂ | X/Y-16 | 2-CH₃ |
| CH₂ | H | CH₂ | X/Y-16 | 2-Cyclopropyl |
| CH₂ | H | CH₂ | X/Y-16 | 2-Cl |
| CH₂ | H | CH₂ | X/Y-16 | 2-OCH₂CH₃ |
| CH(CH₃) | H | CH₂ | X/Y-16 | 2-CH₃ |
| CH(CH₃) | H | CH₂ | X/Y-16 | 2-Cyclopropyl |
| CH₂ | H | CH(CH₃) | X/Y-16 | 2-CH₃ |
| CH₂ | H | CH(CH₃) | X/Y-16 | 2-Cyclopropyl |
| CH₂(CH₃) | H | CH(CH₃) | X/Y-16 | 2-CH₃ |
| CH₂(CH₃) | H | CH(CH₃) | X/Y-16 | 2-Cyclopropyl |
| CH₂(CH₃) | 3-F | CH(CH₃) | X/Y-16 | 2-Cyclopropyl |
| CH₂CH₂ | H | CH₂ | X/Y-16 | 2-Cyclopropyl |
| CH₂CH₂ | H | CH₂CH₂ | X/Y-16 | 2-CH₃ |
| CH₂CH₂CH₂ | H | CH₂ | X/Y-16 | 2-Cyclopropyl |
| CH₂CH₂ | H | CH₂CH₂CH₂ | X/Y-16 | 2-CH₃ |
| CH₂CH(CH₃) | H | CH₂CH₂ | X/Y-16 | 2-Cyclopropyl |
| CH₂CH₂ | 3-F | CH₂CH(CH₃) | X/Y-16 | 2-CH₃ |
| CH₂ | H | CH₂ | X/Y-13 | — |
| CH₂ | H | CH₂ | X/Y-13 | 2-CH₃ |
| CH₂ | H | CH₂ | X/Y-13 | 2-Cyclopropyl |
| CH₂ | H | CH₂ | X/Y-13 | 2-OCH₂CH₃ |
| CH(CH₃) | H | CH₂ | X/Y-13 | 2-OCH₂CH₃ |
| CH(CH₃) | H | CH₂ | X/Y-13 | 2-Cyclopropyl |
| CH₂ | H | CH(CH₃) | X/Y-13 | 2-OCH₂CH₃ |
| CH₂ | H | CH(CH₃) | X/Y-13 | 2-Cyclopropyl |
| CH(CH₃) | H | CH(CH₃) | X/Y-13 | 2-OCH₂CH₃ |
| CH(CH₃) | 3-F | CH(CH₃) | X/Y-13 | 2-Cyclopropyl |
| CH₂CH₂ | H | CH₂ | X/Y-13 | 2-Cyclopropyl |
| CH₂CH₂ | H | CH₂CH₂ | X/Y-13 | 2-CH₃ |
| CH₂CH₂CH₂ | H | CH₂ | X/Y-13 | 2-Cyclopropyl |
| CH₂CH₂ | H | CH₂CH₂CH₂ | X/Y-13 | 2-CH₃ |
| CH(CH₃)CH₂ | 3-F | CH₂CH₂ | X/Y-13 | 2-Cyclopropyl |
| CH₂CH₂ | H | CH(CH₃)CH₂ | X/Y-13 | 2-CH₃ |
| CH₂ | H | CH₂ | X/Y-6 | — |
| CH₂ | H | CH₂ | X/Y-6 | 3-CH₃ |
| CH₂ | H | CH₂ | X/Y-6 | 3-Cyclopropyl |
| CH₂ | H | CH₂ | X/Y-6 | 3-OCH₂CH₃ |
| CH(CH₃) | H | CH(CH₃) | X/Y-6 | 3-Cyclopropyl |
| CH(CH₃) | 3-F | CH(CH₃) | X/Y-6 | 3-Cyclopropyl |
| CH₂CH₂ | H | CH₂ | X/Y-6 | 3-Cyclopropyl |
| CH₂CH₂ | H | CH₂CH₂CH₂ | X/Y-6 | 3-CH₃ |
| CH(CH₃)CH₂ | 3-F | CH₂CH₂ | X/Y-6 | 3-Cyclopropyl |
| CH₂CH₂ | H | CH(CH₃)CH₂ | X/Y-6 | 3-Cyclopropyl |
| CH₂ | H | CH₂ | X/Y-8 | 1-CH₃ |
| CH₂ | H | CH₂ | X/Y-8 | 1,3-(CH₃)₂ |
| CH₂ | H | CH₂ | X/Y-8 | 1,4-(CH₃)₂ |
| CH₂ | H | CH₂ | X/Y-8 | 1-CH₃, 3-Cyclopropyl |
| CH(CH₃) | H | CH(CH₃) | X/Y-8 | 1-CH₃, 3-Cyclopropyl |
| CH(CH₃) | 3-F | CH(CH₃) | X/Y-8 | 1-CH₃, 3-Cyclopropyl |
| CH₂CH₂ | H | CH₂CH₂ | X/Y-8 | 1-CH₃, 3-Cyclopropyl |
| CH₂CH₂ | H | CH₂CH₂CH₂ | X/Y-8 | 1,3-(CH₃)₂ |
| CH₂CH(CH₃) | H | CH₂CH₂ | X/Y-8 | 1-CH₃, 3-Cyclopropyl |
| CH(CH₃)CH₂ | 3-F | CH₂CH₂ | X/Y-8 | 1-CH₃, 3-Cyclopropyl |
| CH₂ | H | CH₂ | X/Y-10 | 1-CH₃ |
| CH₂ | H | CH₂ | X/Y-10 | 1,4-(CH₃)₂ |
| CH₂ | H | CH₂ | X/Y-10 | 1-CH₃, 4-OCH₃ |
| CH₂ | H | CH₂ | X/Y-10 | 1-CH₃, 5-CH(CH₃)₂ |
| CH₂ | H | CH₂ | X/Y-10 | 1-CH₃, 5-Cyclopropyl |
| CH(CH₃) | H | CH(CH₃) | X/Y-10 | 1-CH₃, 5-Cyclopropyl |
| CH(CH₃) | 3-F | CH(CH₃) | X/Y-10 | 1,4-(CH₃)₂ |
| CH₂CH₂ | H | CH₂CH₂ | X/Y-10 | 1-CH₃, 5-Cyclopropyl |
| CH₂CH₂ | H | CH₂CH₂CH₂ | X/Y-10 | 1,5-(CH₃)₂ |
| CH₂CH(CH₃) | H | CH₂CH₂ | X/Y-10 | 1-CH₃, 5-Cyclopropyl |
| CH(CH₃)CH₂ | 3-F | CH₂CH₂ | X/Y-10 | 1-CH₃, 5-Cyclopropyl |
| CH₂ | H | CH₂ | X/Y-7 | — |
| CH₂ | H | CH₂ | X/Y-7 | 3-CH₃ |
| CH(CH₃) | H | CH(CH₃) | X/Y-7 | 3-CH₃ |
| CH(CH₃) | 3-F | CH(CH₃) | X/Y-7 | 3-CH₃ |
| CH₂CH₂ | H | CH₂CH₂ | X/Y-7 | 3-CH₃ |
| CH₂CH₂ | 3-F | CH(CH₃)CH₂CH₂ | X/Y-7 | 3-CH₃ |
| CH₂ | H | CH₂ | X/Y-9 | 1-CH₃ |
| CH₂ | H | CH₂ | X/Y-9 | 1,3-(CH₃)₂ |
| CH₂ | H | CH₂ | X/Y-9 | 1,5-(CH₃)₂ |
| CH(CH₃) | H | CH(CH₃) | X/Y-9 | 1,3-(CH₃)₂ |
| CH(CH₃) | 3-F | CH(CH₃) | X/Y-9 | 1,5-(CH₃)₂ |
| CH₂CH₂ | H | CH₂CH₂ | X/Y-9 | 1,3-(CH₃)₂ |
| CH₂CH₂ | H | CH₂CH₂CH₂ | X/Y-9 | 1,5-(CH₃)₂ |

TABLE E-continued (for structure I.E)

| A | R¹ | B | Y | Substituent on Y |
|---|---|---|---|---|
| CH₂CH(CH₃) | H | CH₂CH₂ | X/Y-9 | 1,3-(CH₃)₂ |
| CH(CH₃)CH₂ | 3-F | CH₂CH₂ | X/Y-9 | 1,5-(CH₃)₂ |
| CH₂ | H | CH₂ | X/Y-25 | 5-CH₂CH₃ |
| CH₂ | H | CH₂ | X/Y-25 | 5-CH(CH₃)₂ |
| CH₂ | H | CH₂ | X/Y-25 | 5-OCH₃ |
| CH(CH₃) | H | CH(CH₃) | X/Y-25 | 5-Cyclopropyl |
| CH₂(CH₃) | H | CH(CH₃) | X/Y-25 | 5-CH₃ |
| CH(CH₃) | H | CH(CH₃) | X/Y-25 | 5-OCH₂CH₃ |
| CH(CH₃) | 3-F | CH(CH₃) | X/Y-25 | 5-Cyclopropyl |
| CH₂CH₂ | H | CH₂ | X/Y-25 | 5-Cyclopropyl |
| CH₂CH₂ | H | CH₂CH₂ | X/Y-25 | 5-CH₃ |
| CH₂CH₂CH₂ | H | CH₂ | X/Y-25 | 5-OCH₂CH₃ |
| CH₂CH₂ | 3-F | CH₂CH(CH₃) | X/Y-25 | 5-Cyclopropyl |
| CH₂ | H | CH(CH₃) | X/Y-25 | 5-Cyclopropyl |
| CH₂ | H | CH₂ | X/Y-23 | — |
| CH₂ | H | CH₂ | X/Y-23 | 5-CH₃ |
| CH₂ | H | CH₂ | X/Y-23 | 5-CH(CH₃)₂ |
| CH₂ | H | CH₂ | X/Y-23 | 5-Cl |
| CH₂ | H | CH₂ | X/Y-23 | 5-OCH₂CH₃ |
| CH₂ | H | CH(CH₃) | X/Y-23 | 5-Cyclopropyl |
| CH₂ | 3-F | CH(CH₃) | X/Y-23 | 5-CH₃ |
| CH₂ | H | CH(CH₃) | X/Y-23 | 5-CH(CH₃)₂ |
| CH(CH₃) | H | CH(CH₃) | X/Y-23 | 5-Cyclopropyl |
| CH₂ | H | CH₂CH₂ | X/Y-23 | 5-Cyclopropyl |
| CH₂CH₂CH₂ | H | CH₂ | X/Y-23 | 5-CH₃ |
| CH₂CH₂ | H | CH₂CH₂ | X/Y-23 | 5-CH(CH₃)₂ |
| CH₂CH₂ | H | CH₂CH₂ | X/Y-23 | 5-Cyclopropyl |
| CH₂ | H | CH₂ | X/Y-26 | 1-CH₃ |
| CH₂ | H | CH₂ | X/Y-26 | 1,5-(CH₃)₂ |
| CH₂ | H | CH₂ | X/Y-26 | 1-CH₃, 5-Cyclopropyl |
| CH(CH₃) | H | CH(CH₃) | X/Y-26 | 1-CH₃, 5-Cyclopropyl |
| CH(CH₃) | H | CH(CH₃) | X/Y-26 | 1,5-(CH₃)₂ |
| CH(CH₃) | 3-F | CH₂ | X/Y-26 | 1-CH₃, 5-Cyclopropyl |
| CH₂CH₂ | H | CH₂CH₂ | X/Y-26 | 1-CH₃, 5-Cyclopropyl |
| CH₂ | H | CH₂CH₂ | X/Y-26 | 1,5-(CH₃)₂ |
| CH₂ | H | CH₂ | X/Y-28 | 1-CH₃ |
| CH₂ | H | CH₂ | X/Y-28 | 1,5-(CH₃)₂ |
| CH₂ | H | CH₂ | X/Y-28 | 1-CH₃, 5-Cyclopropyl |
| CH(CH₃) | H | CH(CH₃) | X/Y-28 | 1-CH₃, 5-Cyclopropyl |
| CH(CH₃) | H | CH(CH₃) | X/Y-28 | 1,5-(CH₃)₂ |
| CH(CH₃) | 3-F | CH₂ | X/Y-28 | 1-CH₃, 5-Cyclopropyl |
| CH₂CH₂ | H | CH₂CH₂ | X/Y-28 | 1-CH₃, 5-Cyclopropyl |
| CH₂ | H | CH₂CH₂ | X/Y-28 | 1,5-(CH₃)₂ |
| CH₂ | H | CH₂ | X/Y-22 | — |
| CH₂ | H | CH₂ | X/Y-22 | 3-CH₃ |
| CH₂ | H | CH₂ | X/Y-22 | 3-Cyclopropyl |
| CH₂ | H | CH₂ | X/Y-22 | 3-OCH₃ |
| CH(CH₃) | H | CH₂ | X/Y-22 | 3-CH₃ |
| CH₂ | H | CH(CH₂) | X/Y-22 | 3-Cyclopropyl |
| CH₂ | 3-F | CH(CH₃) | X/Y-22 | 3-OCH₃ |
| CH₂CH₂ | H | CH₂CH₂ | X/Y-22 | 3-Cyclopropyl |
| CH₂ | H | CH₂CH₂ | X/Y-22 | 3-CH₃ |
| CH₂ | H | CH₂ | X/Y-29 | 1-CH₃ |
| CH₂ | H | CH₂ | X/Y-29 | 1,3-(CH₃)₂ |
| CH₂ | H | CH₂ | X/Y-29 | 1-CH₃, 3-Cyclopropyl |
| CH(CH₃) | H | CH(CH₃) | X/Y-29 | 1,3-(CH₃)₂ |
| CH(CH₃) | 3-F | CH(CH₃) | X/Y-29 | 1-CH₃, 3-Cyclopropyl |
| CH₂CH₂ | H | CH₂CH₂CH₂ | X/Y-29 | 1,3-(CH₃)₂ |
| CH₂CH₂ | H | CH₂CH₂ | X/Y-29 | 1-CH₃, 3-Cyclopropyl |
| CH₂ | H | CH₂ | X/Y-17 | — |
| CH₂ | H | CH₂ | X/Y-17 | 5-Cyclopropyl |
| CH₂ | H | CH₂ | X/Y-17 | 5-CH₃ |
| CH₂ | H | CH₂ | X/Y-17 | 5-OCH₂CH₃ |
| CH₂ | H | CH₂ | X/Y-17 | 5-Cl |
| CH₂ | H | CH₂ | X/Y-17 | 4-CH₃ |
| CH₂ | H | CH₂ | X/Y-17 | 4-Cyclopropyl |
| CH₂ | H | CH₂ | X/Y-17 | 4-OCH₂CH₃ |
| CH₂ | H | CH₂ | X/Y-17 | 4-Cl |
| CH(CH₃) | H | CH(CH₃) | X/Y-17 | 5-Cyclopropyl |
| CH(CH₃) | H | CH(CH₃) | X/Y-17 | 4-Cyclopropyl |
| CH(CH₃) | 3-F | CH(CH₃) | X/Y-17 | 5-OCH₂CH₃ |
| CH₂CH₂ | H | CH₂CH₂ | X/Y-17 | 5-Cyclopropyl |
| CH₂CH₂ | H | CH₂CH₂ | X/Y-17 | 4-Cyclopropyl |
| CH₂CH₂ | H | CH₂CH₂CH₂ | X/Y-17 | 5-CH₃ |
| CH₂ | H | CH₂ | X/Y-14 | — |
| CH₂ | H | CH₂ | X/Y-14 | 5-CH₃ |
| CH₂ | H | CH₂ | X/Y-14 | 5-Cyclopropyl |
| CH₂ | H | CH₂ | X/Y-14 | 4-CH₃ |
| CH₂ | H | CH₂ | X/Y-14 | 4-Cyclopropyl |
| CH₂ | H | CH₂ | X/Y-14 | 4-OCH₂CH₃ |

TABLE E-continued
(for structure I.E)

| A | R¹ | B | Y | Substituent on Y |
|---|---|---|---|---|
| CH₂ | H | CH₂ | X/Y-14 | 5-OCH₂CH₃ |
| CH₂ | H | CH₂ | X/Y-14 | 5-Cl |
| CH(CH₃) | H | CH(CH₃) | X/Y-14 | 4-Cyclopropyl |
| CH(CH₃) | H | CH(CH₃) | X/Y-14 | 5-Cyclopropyl |
| CH(CH₃) | H | CH(CH₃) | X/Y-14 | 4-CH₃ |
| CH(CH₃) | 3-F | CH(CH₃) | X/Y-14 | 4-Cyclopropyl |
| CH₂ | 3-F | CH₂ | X/Y-14 | 5-OCH₂CH₃ |
| CH₂CH₂ | H | CH₂CH₂ | X/Y-14 | 4-Cyclopropyl |
| CH₂CH₂ | H | CH₂CH₂ | X/Y-14 | 5-Cyclopropyl |
| CH₂CH₂ | H | CH₂CH₂CH₂ | X/Y-14 | 5-Cl |
| CH₂CH₂ | H | CH₂CH₂ | X/Y-14 | 4-CH₃ |
| CH₂ | H | CH₂ | X/Y-20 | 1-CH₃ |
| CH₂ | H | CH₂ | X/Y-20 | 1,5-(CH₃)₂ |
| CH(CH₃) | H | CH(CH₃) | X/Y-20 | 1-CH₃ |
| CH(CH₃) | 3-F | CH(CH₃) | X/Y-20 | 1,5-(CH₃)₂ |
| CH₂CH₂ | H | CH₂CH₂ | X/Y-20 | 1-CH₃ |
| CH₂CH₂ | H | CH₂CH₂ | X/Y-20 | 1,5-(CH₃)₂ |
| CH(CH₃)CH₂ | 3-F | CH(CH₃)CH₂ | X/Y-20 | 1,5-(CH₃)₂ |
| CH₂ | H | CH₂ | X/Y-3 | — |
| CH₂ | H | CH₂ | X/Y-3 | 3-CH₃ |
| CH₂ | H | CH₂ | X/Y-3 | 3-CH₂CH₃ |
| CH₂ | H | CH₂ | X/Y-3 | 3-OCH₂CH₃ |
| CH₂ | H | CH₂ | X/Y-3 | 3-CH₂OCH₃ |
| CH₂ | H | CH₂ | X/Y-3 | 3-CF₃ |
| CH(CH₃) | H | CH₂ | X/Y-3 | 3-CH₃ |
| CH(CH₃) | H | CH₂ | X/Y-3 | 3-CH(CH₃)₂ |
| CH(CH₃) | H | CH₂ | X/Y-3 | 3-Cyclopropyl |
| CH₂ | H | CH(CH₃) | X/Y-3 | 3-CH₃ |
| CH₂ | H | CH(CH₃) | X/Y-3 | 3-CH(CH₃)₂ |
| CH₂ | H | CH(CH₃) | X/Y-3 | 3-Cyclopropyl |
| CH(CH₃) | H | CH(CH₃) | X/Y-3 | 3-CH₃ |
| CH(CH₃) | 3-F | CH(CH₃) | X/Y-3 | 3-CH(CH₃)₂ |
| CH(CH₃) | H | CH(CH₃) | X/Y-3 | 3-Cyclopropyl |
| CH₂ | H | CH₂CH₂ | X/Y-3 | 3-CH₃ |
| CH₂CH₂ | H | CH₂CH₂CH₂ | X/Y-3 | 3-CH(CH₃)₂ |
| CH₂ | H | CH₂CH₂ | X/Y-3 | 3-Cyclopropyl |
| CH₂CH₂ | H | CH₂CH(CH₃) | X/Y-3 | 3-Cyclopropyl |
| CH₂CH₂ | H | CH₂CH(CH₃) | X/Y-3 | 3-CH(CH₃)₂ |
| CH₂CH₂CH₂ | 3-F | CH(CH₃)CH₂ | X/Y-3 | 3-CH₃ |
| CH₂ | H | CH₂ | X/Y-5 | — |
| CH₂ | H | CH₂ | X/Y-5 | 5-OCH₂CH₃ |
| CH₂ | H | CH₂ | X/Y-5 | 5-Cyclopropyl |
| CH₂ | H | CH₂ | X/Y-5 | 5-CH₃ |
| CH(CH₃) | 3-F | CH(CH₃) | X/Y-5 | 5-CH₃ |
| CH₂ | H | CH(CH₃) | X/Y-5 | 5-Cyclopropyl |
| CH(CH₃) | H | CH₂ | X/Y-5 | 5-Cyclopropyl |
| CH₂ | H | CH₂CH₂ | X/Y-5 | 5-OCH₂CH₃ |
| CH₂CH₂ | H | CH₂CH₂CH₂ | X/Y-5 | 5-CH₃ |
| CH₂ | H | CH₂ | X/Y-4 | — |
| CH₂ | H | CH₂ | X/Y-4 | 3-OCH₂CH₃ |
| CH₂ | H | CH₂ | X/Y-4 | 5-OCH₂CH₃ |
| CH₂ | H | CH₂ | X/Y-4 | 3-CH(CH₃)₂ |
| CH₂ | H | CH₂ | X/Y-4 | 5-CH₃ |
| CH(CH₃) | 3-F | CH(CH₃) | X/Y-4 | 3-CH(CH₃)₂ |
| CH₂ | H | CH₂ | X/Y-11 | — |
| CH₂ | H | CH₂ | X/Y-11 | 3-CH₃ |
| CH₂ | H | CH₂ | X/Y-11 | 5-CH₃ |
| CH₂ | H | CH(CH₃) | X/Y-11 | 3-CH₃ |
| CH₂ | 3-F | CH(CH₃) | X/Y-11 | 5-CH₃ |
| CH(CH₃) | H | CH(CH₃) | X/Y-11 | 5-CH₃ |
| CH₂ | H | CH₂ | X/Y-21 | — |
| CH₂ | H | CH₂ | X/Y-21 | 4,5-(CH₃)₂ |
| CH₂ | H | CH₂ | X/Y-21 | 4,5-Br₂ |
| CH(CH₃) | H | CH(CH₃) | X/Y-21 | 4,5-Cl₂ |
| CH(CH₃) | H | CH(CH₃) | X/Y-21 | 4,5-(CH₃)₂ |
| CH(CH₃) | H | CH(CH₃) | X/Y-21 | 4,5-Br₂ |
| CH₂ | H | CH₂ | X/Y-30 | — |
| CH₂ | H | CH₂ | X/Y-30 | 3,5-(CH₃)₂ |
| CH(CH₃) | H | CH(CH₃) | X/Y-30 | — |
| CH(CH₃) | H | CH(CH₂) | X/Y-30 | 3,5-(CH₃)₂ |
| CH₂ | H | CH₂ | X/Y-27 | — |
| CH₂ | H | CH₂ | X/Y-27 | 2-Cl |
| CH₂ | H | CH₂ | X/Y-27 | 2,5-(CH₃)₂ |
| CH(CH₃) | H | CH(CH₃) | X/Y-27 | — |
| CH(CH₃) | H | CH(CH₃) | X/Y-27 | 2-Cl |
| CH(CH₃) | H | CH(CH₃) | X/Y-27 | 2,5-(CH₃)₂ |

TABLE F
(for structure I.F)

| A | R¹ | B | Y | Substituent on Y |
|---|---|---|---|---|
| $CH_2$ | H | $CH_2$ | X/Y-1 | |
| $CH(CH_3)$ | H | $CH_2$ | X/Y-1 | |
| $CH(CH_2CH_3)$ | H | $CH_2$ | X/Y-1 | |
| $CH_2$ | H | $CH(CH_3)$ | X/Y-1 | |
| $CH_2$ | H | $CH(CH_2CH_3)$ | X/Y-1 | |
| $CH_2$ | 3-$CH_3$ | $CH_2$ | X/Y-1 | |
| $CH_2$ | 3-F | $CH_2$ | X/Y-1 | |
| $CH_2$ | H | $CH_2$ | X/Y-1 | 5-$CH_3$ |
| $CH_2$ | H | $CH_2$ | X/Y-1 | 4-$CH_3$ |
| $CH_2$ | H | $CH_2$ | X/Y-1 | 3-$CH_3$ |
| $CH_2$ | H | $CH_2$ | X/Y-1 | 5-Cyclopropyl |
| $CH_2$ | H | $CH_2$ | X/Y-1 | 4-Cyclopropyl |
| $CH_2$ | H | $CH_2$ | X/Y-1 | 3-Cyclopropyl |
| $CH_2$ | H | $CH_2$ | X/Y-1 | 5-Cl |
| $CH_2$ | H | $CH_2$ | X/Y-1 | 5-Br |
| $CH_2$ | H | $CH_2$ | X/Y-1 | 4-Cl |
| $CH_2$ | H | $CH_2$ | X/Y-1 | 4-Br |
| $CH_2$ | H | $CH_2$ | X/Y-1 | 4,5-Cl,Cl |
| $CH_2$ | H | $CH_2$ | X/Y-1 | 4-$OCH_2CH_3$ |
| $CH(CH_3)$ | H | $CH_2$ | X/Y-1 | 5-Br |
| $CH(CH_3)$ | H | $CH_2$ | X/Y-1 | 4,5-Cl,Cl |
| $CH(CH_3)$ | H | $CH_2$ | X/Y-1 | 4-Cl |
| $CH_2$ | H | $CH(CH_3)$ | X/Y-1 | 5-Br |
| $CH_2$ | H | $CH(CH_3)$ | X/Y-1 | 4,5-Cl,Cl |
| $CH(CH_3)$ | H | $CH(CH_3)$ | X/Y-1 | — |
| $CH(CH_3)$ | H | $CH(CH_3)$ | X/Y-1 | 4,5-Cl,Cl |
| $CH(CH_3)$ | 3-F | $CH(CH_3)$ | X/Y-1 | — |
| $CH(CH_3)$ | 3-F | $CH(CH_3)$ | X/Y-1 | 5-Br |
| $CH_2CH_2$ | H | $CH_2$ | X/Y-1 | 5-Br |
| $CH_2CH_2$ | H | $CH_2CH_2$ | X/Y-1 | 4,5-Cl,Cl |
| $CH_2CH_2CH_2$ | H | $CH_2$ | X/Y-1 | 5-Br |
| $CH_2CH_2$ | H | $CH_2CH_2CH_2$ | X/Y-1 | 4,5-Cl,Cl |
| $CH_2CH(CH_3)$ | H | $CH_2CH_2$ | X/Y-1 | 4,5-Cl,Cl |
| $CH_2CH_2$ | 3-F | $CH_2CH(CH_3)$ | X/Y-1 | 5-Br |
| $CH_2$ | H | $CH_2$ | X/Y-2 | — |
| $CH_2$ | H | $CH_2$ | X/Y-2 | 4-Cyclopropyl |
| $CH_2$ | H | $CH_2$ | X/Y-2 | 5-Cyclopropyl |
| $CH_2$ | H | $CH_2$ | X/Y-2 | 5-Cl |
| $CH_2$ | H | $CH_2$ | X/Y-2 | 4,5-Cl,Cl |
| $CH_2$ | H | $CH_2$ | X/Y-2 | 4,5-Br,Br |
| $CH_2$ | H | $CH_2$ | X/Y-2 | 4-$CH_3$ |
| $CH_2$ | H | $CH_2$ | X/Y-2 | 5-$CH_3$ |
| $CH_2$ | H | $CH_2$ | X/Y-2 | 4-$OCH_3$ |
| $CH_2$ | H | $CH_2$ | X/Y-2 | 5-$OCH_3$ |
| $CH(CH_3)$ | H | $CH_2$ | X/Y-2 | 4,5-Cl,Cl |
| $CH(CH_3)$ | H | $CH_2$ | X/Y-2 | 4,5-Br,Br |
| $CH_2$ | H | $CH(CH_3)$ | X/Y-2 | 4,5-Cl,Cl |
| $CH_2$ | H | $CH(CH_3)$ | X/Y-2 | 4,5-Br,Br |
| $CH(CH_3)$ | H | $CH(CH_3)$ | X/Y-2 | 4,5-Cl,Cl |
| $CH(CH_3)$ | H | $CH(CH_3)$ | X/Y-2 | 4,5-Br,Br |
| $CH(CH_3)$ | 3-F | $CH(CH_3)$ | X/Y-2 | 4,5-Cl,Cl |
| $CH(CH_3)$ | 3-F | $CH(CH_3)$ | X/Y-2 | 4,5-Br,Br |
| $CH_2CH_2$ | H | $CH_2$ | X/Y-2 | 4,5-Cl,Cl |
| $CH_2CH_2$ | H | $CH_2CH_2$ | X/Y-2 | 4,5-Br,Br |
| $CH_2CH_2CH_2$ | H | $CH_2$ | X/Y-2 | 4,5-Cl,Cl |
| $CH_2CH_2$ | H | $CH_2CH_2CH_2$ | X/Y-2 | 4,5-Br,Br |
| $CH_2CH(CH_3)$ | H | $CH_2CH_2$ | X/Y-2 | 4,5-Br,Br |
| $CH_2CH_2$ | 3-F | $CH_2CH(CH_3)$ | X/Y-2 | 4,5-Cl,Cl |
| $CH_2$ | H | $CH_2$ | X/Y-15 | — |
| $CH_2$ | H | $CH_2$ | X/Y-15 | 2-$CH_3$ |
| $CH_2$ | H | $CH_2$ | X/Y-15 | 2-Cyclopropyl |
| $CH_2$ | H | $CH_2$ | X/Y-15 | 2-$OCH_2CH_3$ |
| $CH_2$ | H | $CH_2$ | X/Y-15 | 2-Cl |
| $CH(CH_3)$ | H | $CH_2$ | X/Y-15 | 2-Cyclopropyl |
| $CH(CH_3)$ | H | $CH_2$ | X/Y-15 | 2-$OCH_2CH_3$ |
| $CH_2$ | H | $CH(CH_3)$ | X/Y-15 | 2-Cyclopropyl |
| $CH_2$ | H | $CH(CH_3)$ | X/Y-15 | 2-$OCH_2CH_3$ |
| $CH(CH_3)$ | H | $CH(CH_3)$ | X/Y-15 | 2-Cyclopropyl |
| $CH(CH_3)$ | H | $CH(CH_3)$ | X/Y-15 | 2-$OCH_2CH_3$ |
| $CH(CH_3)$ | 3-F | $CH(CH_3)$ | X/Y-15 | 2-Cyclopropyl |
| $CH(CH_3)$ | 3-F | $CH(CH_3)$ | X/Y-15 | 2-$OCH_2CH_3$ |
| $CH_2CH_2$ | H | $CH_2$ | X/Y-15 | 2-Cyclopropyl |
| $CH_2CH_2$ | H | $CH_2CH_2$ | X/Y-15 | 2-$OCH_2CH_3$ |
| $CH_2CH_2CH_2$ | H | $CH_2$ | X/Y-15 | 2-Cyclopropyl |
| $CH_2CH_2$ | H | $CH_2CH_2CH_2$ | X/Y-15 | 2-$OCH_2CH_3$ |
| $CH_2CH(CH_3)$ | H | $CH_2CH_2$ | X/Y-15 | 2-Cyclopropyl |
| $CH_2CH_2$ | 3-F | $CH_2CH(CH_3)$ | X/Y-15 | 2-$OCH_2CH_3$ |
| $CH_2$ | H | $CH_2$ | X/Y-12 | — |
| $CH_2$ | H | $CH_2$ | X/Y-12 | 2-$CH_3$ |
| $CH_2$ | H | $CH_2$ | X/Y-12 | 2-Cyclopropyl |

TABLE F-continued (for structure I.F)

| A | R$^1$ | B | Y | Substituent on Y |
|---|---|---|---|---|
| CH$_2$ | H | CH$_2$ | X/Y-12 | 2-OCH$_2$CH$_3$ |
| CH(CH$_3$) | H | CH$_2$ | X/Y-12 | 2-Cyclopropyl |
| CH(CH$_3$) | H | CH$_2$ | X/Y-12 | 2-OCH$_2$CH$_3$ |
| CH$_2$ | H | CH(CH$_3$) | X/Y-12 | 2-Cyclopropyl |
| CH$_2$ | H | CH(CH$_3$) | X/Y-12 | 2-OCH$_2$CH$_3$ |
| CH(CH$_3$) | H | CH(CH$_3$) | X/Y-12 | 2-Cyclopropyl |
| CH(CH$_3$) | 3-F | CH(CH$_3$) | X/Y-12 | 2-OCH$_2$CH$_3$ |
| CH$_2$CH$_2$ | H | CH$_2$ | X/Y-12 | 2-Cyclopropyl |
| CH$_2$CH$_2$ | H | CH$_2$CH$_2$ | X/Y-12 | 2-OCH$_2$CH$_3$ |
| CH$_2$CH$_2$CH$_2$ | H | CH$_2$ | X/Y-12 | 2-Cyclopropyl |
| CH$_2$CH$_2$ | H | CH$_2$CH$_2$CH$_2$ | X/Y-12 | 2-OCH$_2$CH$_3$ |
| CH$_2$CH(CH$_3$) | H | CH$_2$CH$_2$ | X/Y-12 | 2-Cyclopropyl |
| CH$_2$CH$_2$ | 3-F | CH$_2$CH(CH$_3$) | X/Y-12 | 2-Cyclopropyl |
| CH$_2$ | H | CH$_2$ | X/Y-18 | 1-CH$_3$ |
| CH$_2$ | H | CH$_2$ | X/Y-18 | 1,2-(CH$_3$)$_2$ |
| CH$_2$ | H | CH$_2$ | X/Y-18 | 1,4-(CH$_3$)$_2$ |
| CH$_2$ | H | CH$_2$ | X/Y-18 | 1,2,4-(CH$_3$)$_2$ |
| CH$_2$ | H | CH$_2$ | X/Y-18 | 1-CH$_3$, 2-Cyclopropyl |
| CH(CH$_3$) | H | CH$_2$ | X/Y-18 | 1-CH$_3$, 2-Cyclopropyl |
| CH(CH$_3$) | H | CH$_2$ | X/Y-18 | 1,2,4-(CH$_3$)$_3$ |
| CH$_2$ | H | CH(CH$_3$) | X/Y-18 | 1-CH$_3$, 2-Cyclopropyl |
| CH$_2$ | H | CH(CH$_3$) | X/Y-18 | 1,2,4-(CH$_3$)$_3$ |
| CH(CH$_3$) | H | CH(CH$_3$) | X/Y-18 | 1-CH$_3$, 2-Cyclopropyl |
| CH(CH$_3$) | 3-F | CH(CH$_3$) | X/Y-18 | 1,2,4-(CH$_3$)$_3$ |
| CH$_2$CH$_2$ | H | CH$_2$ | X/Y-18 | 1-CH$_3$, 2-Cyclopropyl |
| CH$_2$CH$_2$ | H | CH$_2$CH$_2$ | X/Y-18 | 1,2,4-(CH$_3$)$_2$ |
| CH$_2$CH$_2$CH$_2$ | H | CH$_2$ | X/Y-18 | 1-CH$_3$, 2-Cyclopropyl |
| CH$_2$CH$_2$ | H | CH$_2$CH$_2$CH$_2$ | X/Y-18 | 1,2,4-(CH$_3$)$_2$ |
| CH$_2$CH(CH$_3$) | H | CH$_2$CH$_2$ | X/Y-18 | 1-CH$_3$, 2-Cyclopropyl |
| CH$_2$CH$_2$ | 3-F | CH$_2$CH(CH$_3$) | X/Y-18 | 1,2,4-(CH$_3$)$_2$ |
| CH$_2$ | H | CH$_2$ | X/Y-19 | 1-CH$_3$ |
| CH$_2$ | H | CH$_2$ | X/Y-19 | 1,2-(CH$_3$)$_2$ |
| CH$_2$ | H | CH$_2$ | X/Y-19 | 1,5-(CH$_3$)$_2$ |
| CH$_2$ | H | CH$_2$ | X/Y-19 | 1-CH$_3$, 2-Cyclopropyl |
| CH(CH$_3$) | H | CH$_2$ | X/Y-19 | 1,2-(CH$_3$)$_2$ |
| CH(CH$_3$) | H | CH$_2$ | X/Y-19 | 1-CH$_3$, 2-Cyclopropyl |
| CH$_2$ | H | CH(CH$_3$) | X/Y-19 | 1,2-(CH$_3$)$_2$ |
| CH$_2$ | H | CH(CH$_3$) | X/Y-19 | 1-CH$_3$, 2-Cyclopropyl |
| CH(CH$_3$) | H | CH(CH$_3$) | X/Y-19 | 1,2-(CH$_3$)$_2$ |
| CH(CH$_3$) | H | CH(CH$_3$) | X/Y-19 | 1-CH$_3$, 2-Cyclopropyl |
| CH(CH$_3$) | 3-F | CH$_2$ | X/Y-19 | 1-CH$_3$, 2-Cyclopropyl |
| CH$_2$CH$_2$ | H | CH$_2$ | X/Y-19 | 1-CH$_3$, 2-Cyclopropyl |
| CH$_2$CH$_2$ | H | CH$_2$CH$_2$ | X/Y-19 | 1,2-(CH$_3$)$_2$ |
| CH$_2$CH$_2$CH$_2$ | H | CH$_2$ | X/Y-19 | 1-CH$_3$, 2-Cyclopropyl |
| CH$_2$CH$_2$ | H | CH$_2$CH$_2$CH$_2$ | X/Y-19 | 1,2-(CH$_3$)$_2$ |
| CH$_2$CH(CH$_3$) | H | CH$_2$CH$_2$ | X/Y-19 | 1-CH$_3$, 2-Cyclopropyl |
| CH$_2$CH$_2$ | 3-F | CH$_2$CH(CH$_3$) | X/Y-19 | 1,2-(CH$_3$)$_2$ |
| CH$_2$ | H | CH$_2$ | X/Y-16 | — |
| CH$_2$ | H | CH$_2$ | X/Y-16 | 2-CH$_3$ |
| CH$_2$ | H | CH$_2$ | X/Y-16 | 2-Cyclopropyl |
| CH$_2$ | H | CH$_2$ | X/Y-16 | 2-Cl |
| CH$_2$ | H | CH$_2$ | X/Y-16 | 2-OCH$_2$CH$_3$ |
| CH(CH$_3$) | H | CH$_2$ | X/Y-16 | 2-CH$_3$ |
| CH(CH$_3$) | H | CH$_2$ | X/Y-16 | 2-Cyclopropyl |
| CH$_2$ | H | CH(CH$_3$) | X/Y-16 | 2-CH$_3$ |
| CH$_2$ | H | CH(CH$_3$) | X/Y-16 | 2-Cyclopropyl |
| CH$_2$(CH$_3$) | H | CH(CH$_3$) | X/Y-16 | 2-CH$_3$ |
| CH$_2$(CH$_3$) | H | CH(CH$_3$) | X/Y-16 | 2-Cyclopropyl |
| CH$_2$(CH$_3$) | 3-F | CH(CH$_3$) | X/Y-16 | 2-Cyclopropyl |
| CH$_2$CH$_2$ | H | CH$_2$ | X/Y-16 | 2-Cyclopropyl |
| CH$_2$CH$_2$ | H | CH$_2$CH$_2$ | X/Y-16 | 2-CH$_3$ |
| CH$_2$CH$_2$CH$_2$ | H | CH$_2$ | X/Y-16 | 2-Cyclopropyl |
| CH$_2$CH$_2$ | H | CH$_2$CH$_2$CH$_2$ | X/Y-16 | 2-CH$_3$ |
| CH$_2$CH(CH$_3$) | H | CH$_2$CH$_2$ | X/Y-16 | 2-Cyclopropyl |
| CH$_2$CH$_2$ | 3-F | CH$_2$CH(CH$_3$) | X/Y-16 | 2-CH$_3$ |
| CH$_2$ | H | CH$_2$ | X/Y-13 | — |
| CH$_2$ | H | CH$_2$ | X/Y-13 | 2-CH$_3$ |
| CH$_2$ | H | CH$_2$ | X/Y-13 | 2-Cyclopropyl |
| CH$_2$ | H | CH$_2$ | X/Y-13 | 2-OCH$_2$CH$_3$ |
| CH(CH$_3$) | H | CH$_2$ | X/Y-13 | 2-OCH$_2$CH$_3$ |
| CH(CH$_3$) | H | CH$_2$ | X/Y-13 | 2-Cyclopropyl |
| CH$_2$ | H | CH(CH$_3$) | X/Y-13 | 2-OCH$_2$CH$_3$ |
| CH$_2$ | H | CH(CH$_3$) | X/Y-13 | 2-Cyclopropyl |
| CH(CH$_3$) | H | CH(CH$_3$) | X/Y-13 | 2-OCH$_2$CH$_3$ |
| CH(CH$_3$) | 3-F | CH(CH$_3$) | X/Y-13 | 2-Cyclopropyl |
| CH$_2$CH$_2$ | H | CH$_2$ | X/Y-13 | 2-Cyclopropyl |
| CH$_2$CH$_2$ | H | CH$_2$CH$_2$ | X/Y-13 | 2-CH$_3$ |
| CH$_2$CH$_2$CH$_2$ | H | CH$_2$ | X/Y-13 | 2-Cyclopropyl |
| CH$_2$CH$_2$ | H | CH$_2$CH$_2$CH$_2$ | X/Y-13 | 2-CH$_3$ |
| CH(CH$_3$)CH$_2$ | 3-F | CH$_2$CH$_2$ | X/Y-13 | 2-Cyclopropyl |

TABLE F-continued (for structure I.F)

| A | R¹ | B | Y | Substituent on Y |
|---|---|---|---|---|
| CH₂CH₂ | H | CH(CH₃)CH₂ | X/Y-13 | 2-CH₃ |
| CH₂ | H | CH₂ | X/Y-6 | — |
| CH₂ | H | CH₂ | X/Y-6 | 3-CH₃ |
| CH₂ | H | CH₂ | X/Y-6 | 3-Cyclopropyl |
| CH₂ | H | CH₂ | X/Y-6 | 3-OCH₂CH₃ |
| CH(CH₃) | H | CH(CH₃) | X/Y-6 | 3-Cyclopropyl |
| CH(CH₃) | 3-F | CH(CH₃) | X/Y-6 | 3-Cyclopropyl |
| CH₂CH₂ | H | CH₂CH₂ | X/Y-6 | 3-Cyclopropyl |
| CH₂CH₂ | H | CH₂CH₂CH₂ | X/Y-6 | 3-CH₃ |
| CH(CH₃)CH₂ | 3-F | CH₂CH₂ | X/Y-6 | 3-Cyclopropyl |
| CH₂CH₂ | H | CH(CH₃)CH₂ | X/Y-6 | 3-Cyclopropyl |
| CH₂ | H | CH₂ | X/Y-8 | 1-CH₃ |
| CH₂ | H | CH₂ | X/Y-8 | 1,3-(CH₃)₂ |
| CH₂ | H | CH₂ | X/Y-8 | 1,4-(CH₃)₂ |
| CH₂ | H | CH₂ | X/Y-8 | 1-CH₃, 3-Cyclopropyl |
| CH(CH₃) | H | CH(CH₃) | X/Y-8 | 1-CH₃, 3-Cyclopropyl |
| CH(CH₃) | 3-F | CH(CH₃) | X/Y-8 | 1-CH₃, 3-Cyclopropyl |
| CH₂CH₂ | H | CH₂CH₂ | X/Y-8 | 1-CH₃, 3-Cyclopropyl |
| CH₂CH₂ | H | CH₂CH₂CH₂ | X/Y-8 | 1,3-(CH₃)₂ |
| CH₂CH(CH₃) | H | CH₂CH₂ | X/Y-8 | 1-CH₃, 3-Cyclopropyl |
| CH(CH₃)CH₂ | 3-F | CH₂CH₂ | X/Y-8 | 1-CH₃, 3-Cyclopropyl |
| CH₂ | H | CH₂ | X/Y-10 | 1-CH₃ |
| CH₂ | H | CH₂ | X/Y-10 | 1,4-(CH₃)₂ |
| CH₂ | H | CH₂ | X/Y-10 | 1-CH₃, 4-OCH₃ |
| CH₂ | H | CH₂ | X/Y-10 | 1-CH₃, 5-CH(CH₃)₂ |
| CH₂ | H | CH₂ | X/Y-10 | 1-CH₃, 5-Cyclopropyl |
| CH(CH₃) | H | CH(CH₃) | X/Y-10 | 1-CH₃, 5-Cyclopropyl |
| CH(CH₃) | 3-F | CH(CH₃) | X/Y-10 | 1,4-(CH₃)₂ |
| CH₂CH₂ | H | CH₂CH₂ | X/Y-10 | 1-CH₃, 5-Cyclopropyl |
| CH₂CH₂ | H | CH₂CH₂CH₂ | X/Y-10 | 1,5-(CH₃)₂ |
| CH₂CH(CH₃) | H | CH₂CH₂ | X/Y-10 | 1-CH₃, 5-Cyclopropyl |
| CH(CH₃)CH₂ | 3-F | CH₂CH₂ | X/Y-10 | 1-CH₃, 5-Cyclopropyl |
| CH₂ | H | CH₂ | X/Y-7 | — |
| CH₂ | H | CH₂ | X/Y-7 | 3-CH₃ |
| CH(CH₃) | H | CH(CH₃) | X/Y-7 | 3-CH₃ |
| CH(CH₃) | 3-F | CH(CH₃) | X/Y-7 | 3-CH₃ |
| CH₂CH₂ | H | CH₂CH₂ | X/Y-7 | 3-CH₃ |
| CH₂CH₂ | 3-F | CH(CH₃)CH₂CH₂ | X/Y-7 | 3-CH₃ |
| CH₂ | H | CH₂ | X/Y-9 | 1-CH₃ |
| CH₂ | H | CH₂ | X/Y-9 | 1,3-(CH₃)₂ |
| CH₂ | H | CH₂ | X/Y-9 | 1,5-(CH₃)₂ |
| CH(CH₃) | H | CH(CH₃) | X/Y-9 | 1,3-(CH₃)₂ |
| CH(CH₃) | 3-F | CH(CH₃) | X/Y-9 | 1,5-(CH₃)₂ |
| CH₂CH₂ | H | CH₂CH₂ | X/Y-9 | 1,3-(CH₃)₂ |
| CH₂CH₂ | H | CH₂CH₂CH₂ | X/Y-9 | 1,5-(CH₃)₂ |
| CH₂CH(CH₃) | H | CH₂CH₂ | X/Y-9 | 1,3-(CH₃)₂ |
| CH(CH₃)CH₂ | 3-F | CH₂CH₂ | X/Y-9 | 1,5-(CH₃)₂ |
| CH₂ | H | CH₂ | X/Y-25 | 5-Cyclopropyl |
| CH₂ | H | CH₂ | X/Y-25 | 5-CH₃ |
| CH₂ | H | CH₂ | X/Y-25 | 5-CH₂CH₃ |
| CH₂ | H | CH₂ | X/Y-25 | 5-CH(CH₃)₂ |
| CH₂ | H | CH₂ | X/Y-25 | 5-OCH₃ |
| CH(CH₃) | H | CH(CH₃) | X/Y-25 | 5-Cyclopropyl |
| CH₂(CH₃) | H | CH(CH₃) | X/Y-25 | 5-CH₃ |
| CH(CH₃) | H | CH(CH₃) | X/Y-25 | 5-OCH₂CH₃ |
| CH(CH₃) | 3-F | CH(CH₃) | X/Y-25 | 5-Cyclopropyl |
| CH₂CH₂ | H | CH₂ | X/Y-25 | 5-Cyclopropyl |
| CH₂CH₂ | H | CH₂CH₂ | X/Y-25 | 5-CH₃ |
| CH₂CH₂CH₂ | H | CH₂ | X/Y-25 | 5-OCH₂CH₃ |
| CH₂CH₂ | 3-F | CH₂CH(CH₃) | X/Y-25 | 5-Cyclopropyl |
| CH₂ | H | CH(CH₃) | X/Y-25 | 5-Cyclopropyl |
| CH₂ | H | CH₂ | X/Y-23 | — |
| CH₂ | H | CH₂ | X/Y-23 | 5-Cyclopropyl |
| CH₂ | H | CH₂ | X/Y-23 | 5-CH₃ |
| CH₂ | H | CH₂ | X/Y-23 | 5-CH(CH₃)₂ |
| CH₂ | H | CH₂ | X/Y-23 | 5-Cl |
| CH₂ | H | CH₂ | X/Y-23 | 5-OCH₂CH₃ |
| CH₂ | H | CH(CH₃) | X/Y-23 | 5-Cyclopropyl |
| CH₂ | 3-F | CH(CH₃) | X/Y-23 | 5-CH₃ |
| CH₂ | H | CH(CH₃) | X/Y-23 | 5-CH(CH₃)₂ |
| CH(CH₃) | H | CH(CH₃) | X/Y-23 | 5-Cyclopropyl |
| CH₂ | H | CH₂CH₂ | X/Y-23 | 5-Cyclopropyl |
| CH₂CH₂CH₂ | H | CH₂ | X/Y-23 | 5-CH₃ |
| CH₂CH₂ | H | CH₂CH₂ | X/Y-23 | 5-CH(CH₃)₂ |
| CH₂CH₂ | H | CH₂CH₂ | X/Y-23 | 5-Cyclopropyl |
| CH₂ | H | CH₂ | X/Y-26 | 1-CH₃ |
| CH₂ | H | CH₂ | X/Y-26 | 1,5-(CH₃)₂ |
| CH₂ | H | CH₂ | X/Y-26 | 1-CH₃, 5-Cyclopropyl |
| CH(CH₃) | H | CH(CH₃) | X/Y-26 | 1-CH₃, 5-Cyclopropyl |
| CH(CH₃) | H | CH(CH₃) | X/Y-26 | 1,5-(CH₃)₂ |

TABLE F-continued (for structure I.F)

| A | R¹ | B | Y | Substituent on Y |
|---|---|---|---|---|
| CH(CH₃) | 3-F | CH₂ | X/Y-26 | 1-CH₃, 5-Cyclopropyl |
| CH₂CH₂ | H | CH₂CH₂ | X/Y-26 | 1-CH₃, 5-Cyclopropyl |
| CH₂ | H | CH₂CH₂ | X/Y-26 | 1,5-(CH₃)₂ |
| CH₂ | H | CH₂ | X/Y-28 | 1-CH₃ |
| CH₂ | H | CH₂ | X/Y-28 | 1,5-(CH₃)₂ |
| CH₂ | H | CH₂ | X/Y-28 | 1-CH₃, 5-Cyclopropyl |
| CH(CH₃) | H | CH(CH₃) | X/Y-28 | 1-CH₃, 5-Cyclopropyl |
| CH(CH₃) | H | CH(CH₃) | X/Y-28 | 1,5-(CH₃)₂ |
| CH(CH₃) | 3-F | CH₂ | X/Y-28 | 1-CH₃, 5-Cyclopropyl |
| CH₂CH₂ | H | CH₂CH₂ | X/Y-28 | 1-CH₃, 5-Cyclopropyl |
| CH₂ | H | CH₂CH₂ | X/Y-28 | 1,5-(CH₃)₂ |
| CH₂ | H | CH₂ | X/Y-22 | — |
| CH₂ | H | CH₂ | X/Y-22 | 3-CH₃ |
| CH₂ | H | CH₂ | X/Y-22 | 3-Cyclopropyl |
| CH₂ | H | CH₂ | X/Y-22 | 3-OCH₃ |
| CH(CH₃) | H | CH₂ | X/Y-22 | 3-CH₃ |
| CH₂ | H | CH(CH₃) | X/Y-22 | 3-Cyclopropyl |
| CH₂ | 3-F | CH(CH₃) | X/Y-22 | 3-OCH₃ |
| CH₂CH₂ | H | CH₂CH₂ | X/Y-22 | 3-Cyclopropyl |
| CH₂ | H | CH₂CH₂ | X/Y-22 | 3-CH₃ |
| CH₂ | H | CH₂ | X/Y-29 | 1-CH₃ |
| CH₂ | H | CH₂ | X/Y-29 | 1,3-(CH₃)₂ |
| CH₂ | H | CH₂ | X/Y-29 | 1-CH₃, 3-Cyclopropyl |
| CH(CH₃) | H | CH(CH₃) | X/Y-29 | 1,3-(CH₃)₂ |
| CH(CH₃) | 3-F | CH(CH₃) | X/Y-29 | 1-CH₃, 3-Cyclopropyl |
| CH₂CH₂ | H | CH₂CH₂CH₂ | X/Y-29 | 1,3-(CH₃)₂ |
| CH₂CH₂ | H | CH₂CH₂ | X/Y-29 | 1-CH₃, 3-Cyclopropyl |
| CH₂ | H | CH₂ | X/Y-17 | — |
| CH₂ | H | CH₂ | X/Y-17 | 5-Cyclopropyl |
| CH₂ | H | CH₂ | X/Y-17 | 5-CH₃ |
| CH₂ | H | CH₂ | X/Y-17 | 5-OCH₂CH₃ |
| CH₂ | H | CH₂ | X/Y-17 | 5-Cl |
| CH₂ | H | CH₂ | X/Y-17 | 4-CH₃ |
| CH₂ | H | CH₂ | X/Y-17 | 4-Cyclopropyl |
| CH₂ | H | CH₂ | X/Y-17 | 4-OCH₂CH₃ |
| CH₂ | H | CH₂ | X/Y-17 | 4-Cl |
| CH(CH₃) | H | CH(CH₃) | X/Y-17 | 5-Cyclopropyl |
| CH(CH₃) | H | CH(CH₃) | X/Y-17 | 4-Cyclopropyl |
| CH(CH₃) | 3-F | CH(CH₃) | X/Y-17 | 5-OCH₂CH₃ |
| CH₂CH₂ | H | CH₂CH₂ | X/Y-17 | 5-Cyclopropyl |
| CH₂CH₂ | H | CH₂CH₂ | X/Y-17 | 4-Cyclopropyl |
| CH₂CH₂ | H | CH₂CH₂CH₂ | X/Y-17 | 5-CH₃ |
| CH₂ | H | CH₂ | X/Y-14 | — |
| CH₂ | H | CH₂ | X/Y-14 | 5-CH₃ |
| CH₂ | H | CH₂ | X/Y-14 | 5-Cyclopropyl |
| CH₂ | H | CH₂ | X/Y-14 | 4-CH₃ |
| CH₂ | H | CH₂ | X/Y-14 | 4-Cyclopropyl |
| CH₂ | H | CH₂ | X/Y-14 | 4-OCH₂CH₃ |
| CH₂ | H | CH₂ | X/Y-14 | 5-OCH₂CH₃ |
| CH₂ | H | CH₂ | X/Y-14 | 5-Cl |
| CH(CH₃) | H | CH(CH₃) | X/Y-14 | 4-Cyclopropyl |
| CH(CH₃) | H | CH(CH₃) | X/Y-14 | 5-Cyclopropyl |
| CH(CH₃) | H | CH(CH₃) | X/Y-14 | 4-CH₃ |
| CH(CH₃) | 3-F | CH(CH₃) | X/Y-14 | 4-Cyclopropyl |
| CH₂ | 3-F | CH₂ | X/Y-14 | 5-OCH₂CH₃ |
| CH₂CH₂ | H | CH₂CH₂ | X/Y-14 | 4-Cyclopropyl |
| CH₂CH₂ | H | CH₂CH₂ | X/Y-14 | 5-Cyclopropyl |
| CH₂CH₂ | H | CH₂CH₂CH₂ | X/Y-14 | 5-Cl |
| CH₂CH₂ | H | CH₂CH₂ | X/Y-14 | 4-CH₃ |
| CH₂ | H | CH₂ | X/Y-20 | 1-CH₃ |
| CH₂ | H | CH₂ | X/Y-20 | 1,5-(CH₃)₂ |
| CH(CH₃) | H | CH(CH₃) | X/Y-20 | 1-CH₃ |
| CH(CH₃) | 3-F | CH(CH₃) | X/Y-20 | 1,5-(CH₃)₂ |
| CH₂CH₂ | H | CH₂CH₂ | X/Y-20 | 1-CH₃ |
| CH₂CH₂ | H | CH₂CH₂ | X/Y-20 | 1,5-(CH₃)₂ |
| CH(CH₃)CH₂ | 3-F | CH(CH₃)CH₂ | X/Y-20 | 1,5-(CH₃)₂ |
| CH₂ | H | CH₂ | X/Y-3 | — |
| CH₂ | H | CH₂ | X/Y-3 | 3-CH₃ |
| CH₂ | H | CH₂ | X/Y-3 | 3-CH₂CH₃ |
| CH₂ | H | CH₂ | X/Y-3 | 3-CH(CH₃)₂ |
| CH₂ | H | CH₂ | X/Y-3 | 3-OCH₂CH₃ |
| CH₂ | H | CH₂ | X/Y-3 | 3-CH₂OCH₃ |
| CH₂ | H | CH₂ | X/Y-3 | 3-CF₃ |
| CH(CH₃) | H | CH₂ | X/Y-3 | 3-CH₃ |
| CH(CH₃) | H | CH₂ | X/Y-3 | 3-CH(CH₃)₂ |
| CH(CH₃) | H | CH₂ | X/Y-3 | 3-Cyclopropyl |
| CH₂ | H | CH(CH₃) | X/Y-3 | 3-CH₃ |
| CH₂ | H | CH(CH₃) | X/Y-3 | 3-CH(CH₃)₂ |
| CH₂ | H | CH(CH₃) | X/Y-3 | 3-Cyclopropyl |
| CH(CH₃) | H | CH(CH₃) | X/Y-3 | 3-CH₃ |

TABLE F-continued
(for structure I.F)

| A | R¹ | B | Y | Substituent on Y |
|---|---|---|---|---|
| CH(CH₃) | 3-F | CH(CH₃) | X/Y-3 | 3-CH(CH₃)₂ |
| CH(CH₃) | H | CH(CH₃) | X/Y-3 | 3-Cyclopropyl |
| CH₂ | H | CH₂CH₂ | X/Y-3 | 3-CH₃ |
| CH₂CH₂ | H | CH₂CH₂CH₂ | X/Y-3 | 3-CH(CH₃)₂ |
| CH₂ | H | CH₂CH₂ | X/Y-3 | 3-Cyclopropyl |
| CH₂CH₂ | H | CH₂CH(CH₃) | X/Y-3 | 3-Cyclopropyl |
| CH₂CH₂ | H | CH₂CH(CH₃) | X/Y-3 | 3-CH(CH₃)₂ |
| CH₂CH₂CH₂ | 3-F | CH(CH₃)CH₂ | X/Y-3 | 3-CH₃ |
| CH₂ | H | CH₂ | X/Y-5 | — |
| CH₂ | H | CH₂ | X/Y-5 | 5-OCH₂CH₃ |
| CH₂ | H | CH₂ | X/Y-5 | 5-Cyclopropyl |
| CH₂ | H | CH₂ | X/Y-5 | 5-CH₃ |
| CH(CH₃) | 3-F | CH(CH₃) | X/Y-5 | 5-CH₃ |
| CH₂ | H | CH(CH₃) | X/Y-5 | 5-Cyclopropyl |
| CH(CH₃) | H | CH₂ | X/Y-5 | 5-Cyclopropyl |
| CH₂ | H | CH₂CH₂ | X/Y-5 | 5-OCH₂CH₃ |
| CH₂CH₂ | H | CH₂CH₂CH₂ | X/Y-5 | 5-CH₃ |
| CH₂ | H | CH₂ | X/Y-4 | — |
| CH₂ | H | CH₂ | X/Y-4 | 3-OCH₂CH₃ |
| CH₂ | H | CH₂ | X/Y-4 | 5-OCH₂CH₃ |
| CH₂ | H | CH₂ | X/Y-4 | 3-CH(CH₃)₂ |
| CH₂ | H | CH₂ | X/Y-4 | 5-CH₃ |
| CH(CH₃) | 3-F | CH(CH₃) | X/Y-4 | 3-CH(CH₃)₂ |
| CH₂ | H | CH₂ | X/Y-11 | — |
| CH₂ | H | CH₂ | X/Y-11 | 3-CH₃ |
| CH₂ | H | CH₂ | X/Y-11 | 5-CH₃ |
| CH₂ | H | CH(CH₃) | X/Y-11 | 3-CH₃ |
| CH₂ | 3-F | CH(CH₃) | X/Y-11 | 5-CH₃ |
| CH(CH₃) | H | CH(CH₃) | X/Y-11 | 5-CH₃ |
| CH₂ | H | CH₂ | X/Y-21 | — |
| CH₂ | H | CH₂ | X/Y-21 | 4,5-(CH₃)₂ |
| CH₂ | H | CH₂ | X/Y-21 | 4,5-Br₂ |
| CH(CH₃) | H | CH(CH₃) | X/Y-21 | 4,5-Cl₂ |
| CH(CH₃) | H | CH(CH₃) | X/Y-21 | 4,5-(CH₃)₂ |
| CH(CH₃) | H | CH(CH₃) | X/Y-21 | 4,5-Br₂ |
| CH₂ | H | CH₂ | X/Y-30 | — |
| CH₂ | H | CH₂ | X/Y-30 | 3,5-(CH₃)₂ |
| CH(CH₃) | H | CH(CH₃) | X/Y-30 | — |
| CH(CH₃) | H | CH(CH₃) | X/Y-30 | 3,5-(CH₃)₂ |
| CH₂ | H | CH₂ | X/Y-27 | — |
| CH₂ | H | CH₂ | X/Y-27 | 2-Cl |
| CH₂ | H | CH₂ | X/Y-27 | 2,5-(CH₃)₂ |
| CH(CH₃) | H | CH(CH₃) | X/Y-27 | — |
| CH(CH₃) | H | CH(CH₃) | X/Y-27 | 2-Cl |
| CH(CH₃) | H | CH(CH₃) | X/Y-27 | 2,5-(CH₃)₂ |

TABLE G
(for structure I.G)

| A | R¹ | B | Y | Substituent on Y |
|---|---|---|---|---|
| CH₂ | H | CH₂ | X/Y-1 | |
| CH(CH₃) | H | CH₂ | X/Y-1 | |
| CH(CH₂CH₃) | H | CH₂ | X/Y-1 | |
| CH₂ | H | CH(CH₃) | X/Y-1 | |
| CH₂ | H | CH(CH₂CH₃) | X/Y-1 | |
| CH₂ | 3-CH₃ | CH₂ | X/Y-1 | |
| CH₂ | 3-F | CH₂ | X/Y-1 | |
| CH₂ | H | CH₂ | X/Y-1 | 5-CH₃ |
| CH₂ | H | CH₂ | X/Y-1 | 4-CH₃ |
| CH₂ | H | CH₂ | X/Y-1 | 3-CH₃ |
| CH₂ | H | CH₂ | X/Y-1 | 5-Cyclopropyl |
| CH₂ | H | CH₂ | X/Y-1 | 4-Cyclopropyl |
| CH₂ | H | CH₂ | X/Y-1 | 3-Cyclopropyl |
| CH₂ | H | CH₂ | X/Y-1 | 5-Cl |
| CH₂ | H | CH₂ | X/Y-1 | 5-Br |
| CH₂ | H | CH₂ | X/Y-1 | 4-Cl |
| CH₂ | H | CH₂ | X/Y-1 | 4-Br |
| CH₂ | H | CH₂ | X/Y-1 | 4,5-Cl,Cl |
| CH₂ | H | CH₂ | X/Y-1 | 4-OCH₂CH₃ |
| CH(CH₃) | H | CH₂ | X/Y-1 | 5-Br |
| CH(CH₃) | H | CH₂ | X/Y-1 | 4,5-Cl,Cl |
| CH(CH₃) | H | CH₂ | X/Y-1 | 4-Cl |
| CH₂ | H | CH(CH₃) | X/Y-1 | 5-Br |
| CH₂ | H | CH(CH₃) | X/Y-1 | 4,5-Cl,Cl |
| CH(CH₃) | H | CH(CH₃) | X/Y-1 | — |
| CH(CH₃ | H | CH(CH₃) | X/Y-1 | 4,5-Cl,Cl |
| CH(CH₃) | 3-F | CH(CH₃) | X/Y-1 | — |
| CH(CH₃) | 3-F | CH(CH₃) | X/Y-1 | 5-Br |

TABLE G-continued
(for structure I.G)

| A | $R^1$ | B | Y | Substituent on Y |
|---|---|---|---|---|
| CH$_2$CH$_2$ | H | CH$_2$ | X/Y-1 | 5-Br |
| CH$_2$CH$_2$ | H | CH$_2$CH$_2$ | X/Y-1 | 4,5-Cl,Cl |
| CH$_2$CH$_2$CH$_2$ | H | CH$_2$ | X/Y-1 | 5-Br |
| CH$_2$CH$_2$ | H | CH$_2$CH$_2$CH$_2$ | X/Y-1 | 4,5-Cl,Cl |
| CH$_2$CH(CH$_3$) | H | CH$_2$CH$_2$ | X/Y-1 | 4,5-Cl,Cl |
| CH$_2$CH$_2$ | 3-F | CH$_2$CH(CH$_3$) | X/Y-1 | 5-Br |
| CH$_2$ | H | CH$_2$ | X/Y-2 | — |
| CH$_2$ | H | CH$_2$ | X/Y-2 | 4-Cyclopropyl |
| CH$_2$ | H | CH$_2$ | X/Y-2 | 5-Cyclopropyl |
| CH$_2$ | H | CH$_2$ | X/Y-2 | 5-Cl |
| CH$_2$ | H | CH$_2$ | X/Y-2 | 4,5-Cl,Cl |
| CH$_2$ | H | CH$_2$ | X/Y-2 | 4,5-Br,Br |
| CH$_2$ | H | CH$_2$ | X/Y-2 | 4-CH$_3$ |
| CH$_2$ | H | CH$_2$ | X/Y-2 | 5-CH$_3$ |
| CH$_2$ | H | CH$_2$ | X/Y-2 | 4-OCH$_3$ |
| CH$_2$ | H | CH$_2$ | X/Y-2 | 5-OCH$_3$ |
| CH(CH$_3$) | H | CH$_2$ | X/Y-2 | 4,5-Cl,Cl |
| CH(CH$_3$) | H | CH$_2$ | X/Y-2 | 4,5-Br,Br |
| CH$_2$ | H | CH(CH$_3$) | X/Y-2 | 4,5-Cl,Cl |
| CH$_2$ | H | CH(CH$_3$) | X/Y-2 | 4,5-Br,Br |
| CH(CH$_3$) | H | CH(CH$_3$) | X/Y-2 | 4,5-Cl,Cl |
| CH(CH$_3$) | H | CH(CH$_3$) | X/Y-2 | 4,5-Br,Br |
| CH(CH$_3$) | 3-F | CH(CH$_3$) | X/Y-2 | 4,5-Cl,Cl |
| CH(CH$_3$) | 3-F | CH(CH$_3$) | X/Y-2 | 4,5-Br,Br |
| CH$_2$CH$_2$ | H | CH$_2$ | X/Y-2 | 4,5-Cl,Cl |
| CH$_2$CH$_2$ | H | CH$_2$CH$_2$ | X/Y-2 | 4,5-Br,Br |
| CH$_2$CH$_2$CH$_2$ | H | CH$_2$ | X/Y-2 | 4,5-Cl,Cl |
| CH$_2$CH$_2$ | H | CH$_2$CH$_2$CH$_2$ | X/Y-2 | 4,5-Br,Br |
| CH$_2$CH(CH$_3$) | H | CH$_2$CH$_2$ | X/Y-2 | 4,5-Br,Br |
| CH$_2$CH$_2$ | 3-F | CH$_2$CH(CH$_3$) | X/Y-2 | 4,5-Cl,Cl |
| CH$_2$ | H | CH$_2$ | X/Y-15 | — |
| CH$_2$ | H | CH$_2$ | X/Y-15 | 2-CH$_3$ |
| CH$_2$ | H | CH$_2$ | X/Y-15 | 2-Cyclopropyl |
| CH$_2$ | H | CH$_2$ | X/Y-15 | 2-OCH$_2$CH$_3$ |
| CH$_2$ | H | CH$_2$ | X/Y-15 | 2-Cl |
| CH(CH$_3$) | H | CH$_2$ | X/Y-15 | 2-Cyclopropyl |
| CH(CH$_3$) | H | CH$_2$ | X/Y-15 | 2-OCH$_2$CH$_3$ |
| CH$_2$ | H | CH(CH$_3$) | X/Y-15 | 2-Cyclopropyl |
| CH$_2$ | H | CH(CH$_3$) | X/Y-15 | 2-OCH$_2$CH$_3$ |
| CH(CH$_3$) | H | CH(CH$_3$) | X/Y-15 | 2-Cyclopropyl |
| CH(CH$_3$) | H | CH(CH$_3$) | X/Y-15 | 2-OCH$_2$CH$_3$ |
| CH(CH$_3$) | 3-F | CH(CH$_3$) | X/Y-15 | 2-Cyclopropyl |
| CH(CH$_3$) | 3-F | CH(CH$_3$) | X/Y-15 | 2-OCH$_2$CH$_3$ |
| CH$_2$CH$_2$ | H | CH$_2$ | X/Y-15 | 2-Cyclopropyl |
| CH$_2$CH$_2$ | H | CH$_2$CH$_2$ | X/Y-15 | 2-OCH$_2$CH$_3$ |
| CH$_2$CH$_2$CH$_2$ | H | CH$_2$ | X/Y-15 | 2-Cyclopropyl |
| CH$_2$CH$_2$ | H | CH$_2$CH$_2$CH$_2$ | X/Y-15 | 2-OCH$_2$CH$_3$ |
| CH$_2$CH(CH$_3$) | H | CH$_2$CH$_2$ | X/Y-15 | 2-Cyclopropyl |
| CH$_2$CH$_2$ | 3-F | CH$_2$CH(CH$_3$) | X/Y-15 | 2-OCH$_2$CH$_3$ |
| CH$_2$ | H | CH$_2$ | X/Y-12 | — |
| CH$_2$ | H | CH$_2$ | X/Y-12 | 2-CH$_3$ |
| CH$_2$ | H | CH$_2$ | X/Y-12 | 2-Cyclopropyl |
| CH$_2$ | H | CH$_2$ | X/Y-12 | 2-OCH$_2$CH$_3$ |
| CH(CH$_3$) | H | CH$_2$ | X/Y-12 | 2-Cyclopropyl |
| CH(CH$_3$) | H | CH$_2$ | X/Y-12 | 2-OCH$_2$CH$_3$ |
| CH$_2$ | H | CH(CH$_3$) | X/Y-12 | 2-Cyclopropyl |
| CH$_2$ | H | CH(CH$_3$) | X/Y-12 | 2-OCH$_2$CH$_3$ |
| CH(CH$_3$) | H | CH(CH$_3$) | X/Y-12 | 2-Cyclopropyl |
| CH(CH$_3$) | 3-F | CH(CH$_3$) | X/Y-12 | 2-OCH$_2$CH$_3$ |
| CH$_2$CH$_2$ | H | CH$_2$ | X/Y-12 | 2-Cyclopropyl |
| CH$_2$CH$_2$ | H | CH$_2$CH$_2$ | X/Y-12 | 2-OCH$_2$CH$_3$ |
| CH$_2$CH$_2$CH$_2$ | H | CH$_2$ | X/Y-12 | 2-Cyclopropyl |
| CH$_2$CH$_2$ | H | CH$_2$CH$_2$CH$_2$ | X/Y-12 | 2-OCH$_2$CH$_3$ |
| CH$_2$CH(CH$_3$) | H | CH$_2$CH$_2$ | X/Y-12 | 2-Cyclopropyl |
| CH$_2$CH$_2$ | 3-F | CH$_2$CH(CH$_3$) | X/Y-12 | 2-Cyclopropyl |
| CH$_2$ | H | CH$_2$ | X/Y-18 | 1-CH$_3$ |
| CH$_2$ | H | CH$_2$ | X/Y-18 | 1,2-(CH$_3$)$_2$ |
| CH$_2$ | H | CH$_2$ | X/Y-18 | 1,4-(CH$_3$)$_2$ |
| CH$_2$ | H | CH$_2$ | X/Y-18 | 1,2,4-(CH$_3$)$_2$ |
| CH$_2$ | H | CH$_2$ | X/Y-18 | 1-CH$_3$, 2-Cyclopropyl |
| CH(CH$_3$) | H | CH$_2$ | X/Y-18 | 1-CH$_3$, 2-Cyclopropyl |
| CH(CH$_3$) | H | CH$_2$ | X/Y-18 | 1,2,4-(CH$_3$)$_3$ |
| CH$_2$ | H | CH(CH$_3$) | X/Y-18 | 1-CH$_3$, 2-Cyclopropyl |
| CH$_2$ | H | CH(CH$_3$) | X/Y-18 | 1,2,4-(CH$_3$)$_3$ |
| CH(CH$_3$) | H | CH(CH$_3$) | X/Y-18 | 1-CH$_3$, 2-Cyclopropyl |
| CH(CH$_3$) | 3-F | CH(CH$_3$) | X/Y-18 | 1,2,4-(CH$_3$)$_3$ |
| CH$_2$CH$_2$ | H | CH$_2$ | X/Y-18 | 1-CH$_3$, 2-Cyclopropyl |
| CH$_2$CH$_2$ | H | CH$_2$CH$_2$ | X/Y-18 | 1,2,4-(CH$_3$)$_2$ |
| CH$_2$CH$_2$CH$_2$ | H | CH$_2$ | X/Y-18 | 1-CH$_3$, 2-Cyclopropyl |
| CH$_2$CH$_2$ | H | CH$_2$CH$_2$CH$_2$ | X/Y-18 | 1,2,4-(CH$_3$)$_2$ |

TABLE G-continued (for structure I.G)

| A | R¹ | B | Y | Substituent on Y |
|---|---|---|---|---|
| CH₂CH(CH₃) | H | CH₂CH₂ | X/Y-18 | 1-CH₃, 2-Cyclopropyl |
| CH₂CH₂ | 3-F | CH₂CH(CH₃) | X/Y-18 | 1,2,4-(CH₃)₂ |
| CH₂ | H | CH₂ | X/Y-19 | 1-CH₃ |
| CH₂ | H | CH₂ | X/Y-19 | 1,2-(CH₃)₂ |
| CH₂ | H | CH₂ | X/Y-19 | 1,5-(CH₃)₂ |
| CH₂ | H | CH₂ | X/Y-19 | 1-CH₃, 2-Cyclopropyl |
| CH(CH₃) | H | CH₂ | X/Y-19 | 1,2-(CH₃)₂ |
| CH(CH₃) | H | CH₂ | X/Y-19 | 1-CH₃, 2-Cyclopropyl |
| CH₂ | H | CH(CH₃) | X/Y-19 | 1,2-(CH₃)₂ |
| CH₂ | H | CH(CH₃) | X/Y-19 | 1-CH₃, 2-Cyclopropyl |
| CH(CH₃) | H | CH(CH₃) | X/Y-19 | 1,2-(CH₃)₂ |
| CH(CH₃) | H | CH(CH₃) | X/Y-19 | 1-CH₃, 2-Cyclopropyl |
| CH(CH₃) | 3-F | CH₂ | X/Y-19 | 1-CH₃, 2-Cyclopropyl |
| CH₂CH₂ | H | CH₂ | X/Y-19 | 1-CH₃, 2-Cyclopropyl |
| CH₂CH₂ | H | CH₂CH₂ | X/Y-19 | 1,2-(CH₃)₂ |
| CH₂CH₂CH₂ | H | CH₂ | X/Y-19 | 1-CH₃, 2-Cyclopropyl |
| CH₂CH₂ | H | CH₂CH₂CH₂ | X/Y-19 | 1,2-(CH₃)₂ |
| CH₂CH(CH₃) | H | CH₂CH₂ | X/Y-19 | 1-CH₃, 2-Cyclopropyl |
| CH₂CH₂ | 3-F | CH₂CH(CH₃) | X/Y-19 | 1,2-(CH₃)₂ |
| CH₂ | H | CH₂ | X/Y-16 | — |
| CH₂ | H | CH₂ | X/Y-16 | 2-CH₃ |
| CH₂ | H | CH₂ | X/Y-16 | 2-Cyclopropyl |
| CH₂ | H | CH₂ | X/Y-16 | 2-Cl |
| CH₂ | H | CH₂ | X/Y-16 | 2-OCH₂CH₃ |
| CH(CH₃) | H | CH₂ | X/Y-16 | 2-CH₃ |
| CH(CH₃) | H | CH₂ | X/Y-16 | 2-Cyclopropyl |
| CH₂ | H | CH(CH₃) | X/Y-16 | 2-CH₃ |
| CH₂ | H | CH(CH₃) | X/Y-16 | 2-Cyclopropyl |
| CH₂(CH₃) | H | CH(CH₃) | X/Y-16 | 2-CH₃ |
| CH₂(CH₃) | H | CH(CH₃) | X/Y-16 | 2-Cyclopropyl |
| CH₂(CH₃) | 3-F | CH(CH₃) | X/Y-16 | 2-Cyclopropyl |
| CH₂CH₂ | H | CH₂ | X/Y-16 | 2-Cyclopropyl |
| CH₂CH₂ | H | CH₂CH₂ | X/Y-16 | 2-CH₃ |
| CH₂CH₂CH₂ | H | CH₂ | X/Y-16 | 2-Cyclopropyl |
| CH₂CH₂ | H | CH₂CH₂CH₂ | X/Y-16 | 2-CH₃ |
| CH₂CH(CH₃) | H | CH₂CH₂ | X/Y-16 | 2-Cyclopropyl |
| CH₂CH₂ | 3-F | CH₂CH(CH₃) | X/Y-16 | 2-CH₃ |
| CH₂ | H | CH₂ | X/Y-13 | — |
| CH₂ | H | CH₂ | X/Y-13 | 2-CH₃ |
| CH₂ | H | CH₂ | X/Y-13 | 2-Cyclopropyl |
| CH₂ | H | CH₂ | X/Y-13 | 2-OCH₂CH₃ |
| CH(CH₃) | H | CH₂ | X/Y-13 | 2-OCH₂CH₃ |
| CH(CH₃) | H | CH₂ | X/Y-13 | 2-Cyclopropyl |
| CH₂ | H | CH(CH₃) | X/Y-13 | 2-OCH₂CH₃ |
| CH₂ | H | CH(CH₃) | X/Y-13 | 2-Cyclopropyl |
| CH(CH₃) | H | CH(CH₃) | X/Y-13 | 2-OCH₂CH₃ |
| CH(CH₃) | 3-F | CH(CH₃) | X/Y-13 | 2-Cyclopropyl |
| CH₂CH₂ | H | CH₂ | X/Y-13 | 2-Cyclopropyl |
| CH₂CH₂ | H | CH₂CH₂ | X/Y-13 | 2-CH₃ |
| CH₂CH₂CH₂ | H | CH₂ | X/Y-13 | 2-Cyclopropyl |
| CH₂CH₂ | H | CH₂CH₂CH₂ | X/Y-13 | 2-CH₃ |
| CH(CH₃)CH₂ | 3-F | CH₂CH₂ | X/Y-13 | 2-Cyclopropyl |
| CH₂CH₂ | H | CH(CH₃)CH₂ | X/Y-13 | 2-CH₃ |
| CH₂ | H | CH₂ | X/Y-6 | — |
| CH₂ | H | CH₂ | X/Y-6 | 3-CH₃ |
| CH₂ | H | CH₂ | X/Y-6 | 3-Cyclopropyl |
| CH₂ | H | CH₂ | X/Y-6 | 3-OCH₂CH₃ |
| CH(CH₃) | H | CH(CH₃) | X/Y-6 | 3-Cyclopropyl |
| CH(CH₃) | 3-F | CH(CH₃) | X/Y-6 | 3-Cyclopropyl |
| CH₂CH₂ | H | CH₂CH₂ | X/Y-6 | 3-Cyclopropyl |
| CH₂CH₂ | H | CH₂CH₂CH₂ | X/Y-6 | 3-CH₃ |
| CH(CH₃)CH₂ | 3-F | CH₂CH₂ | X/Y-6 | 3-Cyclopropyl |
| CH₂CH₂ | H | CH(CH₃)CH₂ | X/Y-6 | 3-Cyclopropyl |
| CH₂ | H | CH₂ | X/Y-8 | 1-CH₃ |
| CH₂ | H | CH₂ | X/Y-8 | 1,3-(CH₃)₂ |
| CH₂ | H | CH₂ | X/Y-8 | 1,4-(CH₃)₂ |
| CH₂ | H | CH₂ | X/Y-8 | 1-CH₃, 3-Cyclopropyl |
| CH(CH₃) | H | CH(CH₃) | X/Y-8 | 1-CH₃, 3-Cyclopropyl |
| CH(CH₃) | 3-F | CH(CH₃) | X/Y-8 | 1-CH₃, 3-Cyclopropyl |
| CH₂CH₂ | H | CH₂CH₂ | X/Y-8 | 1-CH₃, 3-Cyclopropyl |
| CH₂CH₂ | H | CH₂CH₂CH₂ | X/Y-8 | 1,3-(CH₃)₂ |
| CH₂CH(CH₃) | H | CH₂CH₂ | X/Y-8 | 1-CH₃, 3-Cyclopropyl |
| CH(CH₃)CH₂ | 3-F | CH₂CH₂ | X/Y-8 | 1-CH₃, 3-Cyclopropyl |
| CH₂ | H | CH₂ | X/Y-10 | 1-CH₃ |
| CH₂ | H | CH₂ | X/Y-10 | 1,4-(CH₃)₂ |
| CH₂ | H | CH₂ | X/Y-10 | 1-CH₃, 4-OCH₃ |
| CH₂ | H | CH₂ | X/Y-10 | 1-CH₃, 5-CH(CH₃)₂ |
| CH₂ | H | CH₂ | X/Y-10 | 1-CH₃, 5-Cyclopropyl |
| CH(CH₃) | H | CH(CH₃) | X/Y-10 | 1-CH₃, 5-Cyclopropyl |
| CH(CH₃) | 3-F | CH(CH₃) | X/Y-10 | 1,4-(CH₃)₂ |

TABLE G-continued (for structure I.G)

| A | R¹ | B | Y | Substituent on Y |
|---|---|---|---|---|
| CH₂CH₂ | H | CH₂CH₂ | X/Y-10 | 1-CH₃, 5-Cyclopropyl |
| CH₂CH₂ | H | CH₂CH₂CH₂ | X/Y-10 | 1,5-(CH₃)₂ |
| CH₂CH(CH₃) | H | CH₂CH₂ | X/Y-10 | 1-CH₃, 5-Cyclopropyl |
| CH(CH₃)CH₂ | 3-F | CH₂CH₂ | X/Y-10 | 1-CH₃, 5-Cyclopropyl |
| CH₂ | H | CH₂ | X/Y-7 | — |
| CH₂ | H | CH₂ | X/Y-7 | 3-CH₃ |
| CH(CH₃) | H | CH(CH₃) | X/Y-7 | 3-CH₃ |
| CH(CH₃) | 3-F | CH(CH₃) | X/Y-7 | 3-CH₃ |
| CH₂CH₂ | H | CH₂CH₂ | X/Y-7 | 3-CH₃ |
| CH₂CH₂ | 3-F | CH(CH₃)CH₂CH₂ | X/Y-7 | 3-CH₃ |
| CH₂ | H | CH₂ | X/Y-9 | 1-CH₃ |
| CH₂ | H | CH₂ | X/Y-9 | 1,3-(CH₃)₂ |
| CH₂ | H | CH₂ | X/Y-9 | 1,5-(CH₃)₂ |
| CH(CH₃) | H | CH(CH₃) | X/Y-9 | 1,3-(CH₃)₂ |
| CH(CH₃) | 3-F | CH(CH₃) | X/Y-9 | 1,5-(CH₃)₂ |
| CH₂CH₂ | H | CH₂CH₂ | X/Y-9 | 1,3-(CH₃)₂ |
| CH₂CH₂ | H | CH₂CH₂CH₂ | X/Y-9 | 1,5-(CH₃)₂ |
| CH₂CH(CH₃) | H | CH₂CH₂ | X/Y-9 | 1,3-(CH₃)₂ |
| CH(CH₃)CH₂ | 3-F | CH₂CH₂ | X/Y-9 | 1,5-(CH₃)₂ |
| CH₂ | H | CH₂ | X/Y-25 | 5-CH₃ |
| CH₂ | H | CH₂ | X/Y-25 | 5-CH₂CH₃ |
| CH₂ | H | CH₂ | X/Y-25 | 5-CH(CH₃)₂ |
| CH₂ | H | CH₂ | X/Y-25 | 5-OCH₃ |
| CH(CH₃) | H | CH(CH₃) | X/Y-25 | 5-Cyclopropyl |
| CH₂(CH₃) | H | CH(CH₃) | X/Y-25 | 5-CH₃ |
| CH(CH₃) | H | CH(CH₃) | X/Y-25 | 5-OCH₂CH₃ |
| CH(CH₃) | 3-F | CH(CH₃) | X/Y-25 | 5-Cyclopropyl |
| CH₂CH₂ | H | CH₂ | X/Y-25 | 5-Cyclopropyl |
| CH₂CH₂ | H | CH₂CH₂ | X/Y-25 | 5-CH₃ |
| CH₂CH₂CH₂ | H | CH₂ | X/Y-25 | 5-OCH₂CH₃ |
| CH₂CH₂ | 3-F | CH₂CH(CH₃) | X/Y-25 | 5-Cyclopropyl |
| CH₂ | H | CH(CH₃) | X/Y-25 | 5-Cyclopropyl |
| CH₂ | H | CH₂ | X/Y-23 | — |
| CH₂ | H | CH₂ | X/Y-23 | 5-CH₃ |
| CH₂ | H | CH₂ | X/Y-23 | 5-CH(CH₃)₂ |
| CH₂ | H | CH₂ | X/Y-23 | 5-Cl |
| CH₂ | H | CH₂ | X/Y-23 | 5-OCH₂CH₃ |
| CH₂ | H | CH(CH₃) | X/Y-23 | 5-Cyclopropyl |
| CH₂ | 3-F | CH(CH₃) | X/Y-23 | 5-CH₃ |
| CH₂ | H | CH(CH₃) | X/Y-23 | 5-CH(CH₃)₂ |
| CH(CH₃) | H | CH(CH₃) | X/Y-23 | 5-Cyclopropyl |
| CH₂ | H | CH₂CH₂ | X/Y-23 | 5-Cyclopropyl |
| CH₂CH₂CH₂ | H | CH₂ | X/Y-23 | 5-CH₃ |
| CH₂CH₂ | H | CH₂CH₂ | X/Y-23 | 5-CH(CH₃)₂ |
| CH₂CH₂ | H | CH₂CH₂ | X/Y-23 | 5-Cyclopropyl |
| CH₂ | H | CH₂ | X/Y-26 | 1-CH₃ |
| CH₂ | H | CH₂ | X/Y-26 | 1,5-(CH₃)₂ |
| CH₂ | H | CH₂ | X/Y-26 | 1-CH₃, 5-Cyclopropyl |
| CH(CH₃) | H | CH(CH₃) | X/Y-26 | 1-CH₃, 5-Cyclopropyl |
| CH(CH₃) | H | CH(CH₃) | X/Y-26 | 1,5-(CH₃)₂ |
| CH(CH₃) | 3-F | CH₂ | X/Y-26 | 1-CH₃, 5-Cyclopropyl |
| CH₂CH₂ | H | CH₂CH₂ | X/Y-26 | 1-CH₃, 5-Cyclopropyl |
| CH₂ | H | CH₂CH₂ | X/Y-26 | 1,5(CH₃)₂ |
| CH₂ | H | CH₂ | X/Y-28 | 1-CH₃ |
| CH₂ | H | CH₂ | X/Y-28 | 1,5-(CH₃)₂ |
| CH₂ | H | CH₂ | X/Y-28 | 1-CH₃, 5-Cyclopropyl |
| CH(CH₃) | H | CH(CH₃) | X/Y-28 | 1-CH₃, 5-Cyclopropyl |
| CH(CH₃) | H | CH(CH₃) | X/Y-28 | 1,5-(CH₃)₂ |
| CH(CH₃) | 3-F | CH₂ | X/Y-28 | 1-CH₃, 5-Cyclopropyl |
| CH₂CH₂ | H | CH₂CH₂ | X/Y-28 | 1-CH₃, 5-Cyclopropyl |
| CH₂ | H | CH₂CH₂ | X/Y-28 | 1,5-(CH₃)₂ |
| CH₂ | H | CH₂ | X/Y-22 | — |
| CH₂ | H | CH₂ | X/Y-22 | 3-CH₃ |
| CH₂ | H | CH₂ | X/Y-22 | 3-Cyclopropyl |
| CH₂ | H | CH₂ | X/Y-22 | 3-OCH₃ |
| CH(CH₃) | H | CH₂ | X/Y-22 | 3-CH₃ |
| CH₂ | H | CH(CH₃) | X/Y-22 | 3-Cyclopropyl |
| CH₂ | 3-F | CH(CH₃) | X/Y-22 | 3-OCH₃ |
| CH₂CH₂ | H | CH₂CH₂ | X/Y-22 | 3-Cyclopropyl |
| CH₂ | H | CH₂CH₂ | X/Y-22 | 3-CH₃ |
| CH₂ | H | CH₂ | X/Y-29 | 1-CH₃ |
| CH₂ | H | CH₂ | X/Y-29 | 1,3-(CH₃)₂ |
| CH₂ | H | CH₂ | X/Y-29 | 1-CH₃, 3-Cyclopropyl |
| CH(CH₃) | H | CH(CH₃) | X/Y-29 | 1,3-(CH₃)₂ |
| CH(CH₃) | 3-F | CH(CH₃) | X/Y-29 | 1-CH₃, 3-Cyclopropyl |
| CH₂CH₂ | H | CH₂CH₂CH₂ | X/Y-29 | 1,3-(CH₃)₂ |
| CH₂CH₂ | H | CH₂CH₂ | X/Y-29 | 1-CH₃, 3-Cyclopropyl |
| CH₂ | H | CH₂ | X/Y-17 | — |
| CH₂ | H | CH₂ | X/Y-17 | 5-Cyclopropyl |
| CH₂ | H | CH₂ | X/Y-17 | 5-CH₃ |

TABLE G-continued (for structure I.G)

| A | R¹ | B | Y | Substituent on Y |
|---|----|---|---|------------------|
| $CH_2$ | H | $CH_2$ | X/Y-17 | 5-$OCH_2CH_3$ |
| $CH_2$ | H | $CH_2$ | X/Y-17 | 5-Cl |
| $CH_2$ | H | $CH_2$ | X/Y-17 | 4-$CH_3$ |
| $CH_2$ | H | $CH_2$ | X/Y-17 | 4-Cyclopropyl |
| $CH_2$ | H | $CH_2$ | X/Y-17 | 4-$OCH_2CH_3$ |
| $CH_2$ | H | $CH_2$ | X/Y-17 | 4-Cl |
| $CH(CH_3)$ | H | $CH(CH_3)$ | X/Y-17 | 5-Cyclopropyl |
| $CH(CH_3)$ | H | $CH(CH_3)$ | X/Y-17 | 4-Cyclopropyl |
| $CH(CH_3)$ | 3-F | $CH(CH_3)$ | X/Y-17 | 5-$OCH_2CH_3$ |
| $CH_2CH_2$ | H | $CH_2CH_2$ | X/Y-17 | 5-Cyclopropyl |
| $CH_2CH_2$ | H | $CH_2CH_2$ | X/Y-17 | 4-Cyclopropyl |
| $CH_2CH_2$ | H | $CH_2CH_2CH_2$ | X/Y-17 | 5-$CH_3$ |
| $CH_2$ | H | $CH_2$ | X/Y-14 | — |
| $CH_2$ | H | $CH_2$ | X/Y-14 | 5-$CH_3$ |
| $CH_2$ | H | $CH_2$ | X/Y-14 | 5-Cyclopropyl |
| $CH_2$ | H | $CH_2$ | X/Y-14 | 4-$CH_3$ |
| $CH_2$ | H | $CH_2$ | X/Y-14 | 4-Cyclopropyl |
| $CH_2$ | H | $CH_2$ | X/Y-14 | 4-$OCH_2CH_3$ |
| $CH_2$ | H | $CH_2$ | X/Y-14 | 5-$OCH_2CH_3$ |
| $CH_2$ | H | $CH_2$ | X/Y-14 | 5-Cl |
| $CH(CH_3)$ | H | $CH(CH_3)$ | X/Y-14 | 4-Cyclopropyl |
| $CH(CH_3)$ | H | $CH(CH_3)$ | X/Y-14 | 5-Cyclopropyl |
| $CH(CH_3)$ | H | $CH(CH_3)$ | X/Y-14 | 4-$CH_3$ |
| $CH(CH_3)$ | 3-F | $CH(CH_3)$ | X/Y-14 | 4-Cyclopropyl |
| $CH_2$ | 3-F | $CH_2$ | X/Y-14 | 5-$OCH_2CH_3$ |
| $CH_2CH_2$ | H | $CH_2CH_2$ | X/Y-14 | 4-Cyclopropyl |
| $CH_2CH_2$ | H | $CH_2CH_2$ | X/Y-14 | 5-Cyclopropyl |
| $CH_2CH_2$ | H | $CH_2CH_2CH_2$ | X/Y-14 | 5-Cl |
| $CH_2CH_2$ | H | $CH_2CH_2$ | X/Y-14 | 4-$CH_3$ |
| $CH_2$ | H | $CH_2$ | X/Y-20 | 1-$CH_3$ |
| $CH_2$ | H | $CH_2$ | X/Y-20 | 1,5-$(CH_3)_2$ |
| $CH(CH_3)$ | H | $CH(CH_3)$ | X/Y-20 | 1-$CH_3$ |
| $CH(CH_3)$ | 3-F | $CH(CH_3)$ | X/Y-20 | 1,5-$(CH_3)_2$ |
| $CH_2CH_2$ | H | $CH_2CH_2$ | X/Y-20 | 1-$CH_3$ |
| $CH_2CH_2$ | H | $CH_2CH_2$ | X/Y-20 | 1,5-$(CH_3)_2$ |
| $CH(CH_3)CH_2$ | 3-F | $CH(CH_3)CH_2$ | X/Y-20 | 1,5-$(CH_3)_2$ |
| $CH_2$ | H | $CH_2$ | X/Y-3 | — |
| $CH_2$ | H | $CH_2$ | X/Y-3 | 3-$CH_3$ |
| $CH_2$ | H | $CH_2$ | X/Y-3 | 3-$CH_2CH_3$ |
| $CH_2$ | H | $CH_2$ | X/Y-3 | 3-$CH(CH_3)_2$ |
| $CH_2$ | H | $CH_2$ | X/Y-3 | 3-$OCH_2CH_3$ |
| $CH_2$ | H | $CH_2$ | X/Y-3 | 3-$CH_2OCH_3$ |
| $CH_2$ | H | $CH_2$ | X/Y-3 | 3-$CF_3$ |
| $CH(CH_3)$ | H | $CH_2$ | X/Y-3 | 3-$CH_3$ |
| $CH(CH_3)$ | H | $CH_2$ | X/Y-3 | 3-$CH(CH_3)_2$ |
| $CH(CH_3)$ | H | $CH_2$ | X/Y-3 | 3-Cyclopropyl |
| $CH_2$ | H | $CH(CH_3)$ | X/Y-3 | 3-$CH_3$ |
| $CH_2$ | H | $CH(CH_3)$ | X/Y-3 | 3-$CH(CH_3)_2$ |
| $CH_2$ | H | $CH(CH_3)$ | X/Y-3 | 3-Cyclopropyl |
| $CH(CH_3)$ | H | $CH(CH_3)$ | X/Y-3 | 3-$CH_3$ |
| $CH(CH_3)$ | 3-F | $CH(CH_3)$ | X/Y-3 | 3-$CH(CH_3)_2$ |
| $CH(CH_3)$ | H | $CH(CH_3)$ | X/Y-3 | 3-Cyclopropyl |
| $CH_2$ | H | $CH_2CH_2$ | X/Y-3 | 3-$CH_3$ |
| $CH_2CH_2$ | H | $CH_2CH_2CH_2$ | X/Y-3 | 3-$CH(CH_3)_2$ |
| $CH_2$ | H | $CH_2CH_2$ | X/Y-3 | 3-Cyclopropyl |
| $CH_2CH_2$ | H | $CH_2CH(CH_3)$ | X/Y-3 | 3-Cyclopropyl |
| $CH_2CH_2$ | H | $CH_2CH(CH_3)$ | X/Y-3 | 3-$CH(CH_3)_2$ |
| $CH_2CH_2CH_2$ | 3-F | $CH(CH_3)CH_2$ | X/Y-3 | 3-$CH_3$ |
| $CH_2$ | H | $CH_2$ | X/Y-5 | — |
| $CH_2$ | H | $CH_2$ | X/Y-5 | 5-$OCH_2CH_3$ |
| $CH_2$ | H | $CH_2$ | X/Y-5 | 5-Cyclopropyl |
| $CH_2$ | H | $CH_2$ | X/Y-5 | 5-$CH_3$ |
| $CH(CH_3)$ | 3-F | $CH(CH_3)$ | X/Y-5 | 5-$CH_3$ |
| $CH_2$ | H | $CH(CH_3)$ | X/Y-5 | 5-Cyclopropyl |
| $CH(CH_3)$ | H | $CH_2$ | X/Y-5 | 5-Cyclopropyl |
| $CH_2$ | H | $CH_2CH_2$ | X/Y-5 | 5-$OCH_2CH_3$ |
| $CH_2CH_2$ | H | $CH_2CH_2CH_2$ | X/Y-5 | 5-$CH_3$ |
| $CH_2$ | H | $CH_2$ | X/Y-4 | — |
| $CH_2$ | H | $CH_2$ | X/Y-4 | 3-$OCH_2CH_3$ |
| $CH_2$ | H | $CH_2$ | X/Y-4 | 5-$OCH_2CH_3$ |
| $CH_2$ | H | $CH_2$ | X/Y-4 | 3-$CH(CH_3)_2$ |
| $CH_2$ | H | $CH_2$ | X/Y-4 | 5-$CH_3$ |
| $CH(CH_3)$ | 3-F | $CH(CH_3)$ | X/Y-4 | 3-$CH(CH_3)_2$ |
| $CH_2$ | H | $CH_2$ | X/Y-11 | — |
| $CH_2$ | H | $CH_2$ | X/Y-11 | 3-$CH_3$ |
| $CH_2$ | H | $CH_2$ | X/Y-11 | 5-$CH_3$ |
| $CH_2$ | H | $CH(CH_3)$ | X/Y-11 | 3-$CH_3$ |
| $CH_2$ | 3-F | $CH(CH_3)$ | X/Y-11 | 5-$CH_3$ |
| $CH(CH_3)$ | H | $CH(CH_3)$ | X/Y-11 | 5-$CH_3$ |
| $CH_2$ | H | $CH_2$ | X/Y-21 | — |

TABLE G-continued (for structure I.G)

| A | R¹ | B | Y | Substituent on Y |
|---|----|---|---|------------------|
| CH₂ | H | CH₂ | X/Y-21 | 4,5-(CH₃)₂ |
| CH₂ | H | CH₂ | X/Y-21 | 4,5-Br₂ |
| CH(CH₃) | H | CH(CH₃) | X/Y-21 | 4,5-Cl₂ |
| CH(CH₃) | H | CH(CH₃) | X/Y-21 | 4,5-(CH₃)₂ |
| CH(CH₃) | H | CH(CH₃) | X/Y-21 | 4,5-Br₂ |
| CH₂ | H | CH₂ | X/Y-30 | — |
| CH₂ | H | CH₂ | X/Y-30 | 3,5-(CH₃)₂ |
| CH(CH₃) | H | CH(CH₃) | X/Y-30 | — |
| CH(CH₃) | H | CH(CH₃) | X/Y-30 | 3,5-(CH₃)₂ |
| CH₂ | H | CH₂ | X/Y-27 | — |
| CH₂ | H | CH₂ | X/Y-27 | 2-Cl |
| CH₂ | H | CH₂ | X/Y-27 | 2,5-(CH₃)₂ |
| CH(CH₃) | H | CH(CH₃) | X/Y-27 | — |
| CH(CH₃) | H | CH(CH₃) | X/Y-27 | 2-Cl |
| CH(CH₃) | H | CH(CH₃) | X/Y-27 | 2,5-(CH₃)₂ |

The hydroquinone diethers of the formula I are suitable for effectively controlling pests from the class consisting of the insects, arachnids and nematodes. They can be used as pesticides in crop protection and in the hygiene and veterinary sectors and for the protection of stored material.

The insect pests include, from the order of the butterflies (Lepidoptera), for example, *Agrotis ypsilon, Agrotis segetum, Alabam agrillacea, Anticarsia gemmatalis, Argyesthia conjugella, Autographa gamma, Bupulus piniarius, Cacoecia murinana, Capua reticulana, Cheimatobia brumata, Choristoneura fumiferana, Choristoneura occidentalis, Cirphis unipuncta, Cydia pomonell, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliara, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistris citrella, Pieris brassicae, Plathypena scarbra, Plutella xylostella, Pseudoplusia includens, Phyacionia frustrana, Scrobipalpula absoluta, Sitotroga Cerelella, Sparganothis pilleriana, Spodoptera frugiperda, Spodoptera littoralis, Spodoptera litura, Thaumatopoea pityocampa, Tortrix viridana, Trichloplusia ni* and *Zeiraphera canadensis;* from the order of the beetles (Coleoptera), for example, *Agrilius sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betular, Cassida Nebulos, Cerotoma trifurcata, Ceuthorrhynchus assimils, Ceuthorrynchus napi, Chaetocnema tibialis, Conoderus vespertinus, Crioceris asparagi, Diabrotics longicornis, Diabrotica 12-punctat, Diagrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta crysocephala, Phyllophaga sp., Phyllopertha horitcola, Phyllotreta nemorum, Phyllotreta striolata, Popillia japonica, Sitaon lineatus* or *Sitophilus granaria;* from the order of the Diptera, for example, *Aedes aegypti, Aedes vexans, Anastrepha ludens, Anopheles maculipennis, Ceratitis capitat, Chrysomya ezziana, Chrysomya hominivorax, Chrysomya macellaria, Contrainia sorphicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodilosis equestris, Hylemyia platura, Hyoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletic cerasi, Rhagoletis pomonella, Tabaus bovinus, Tipula oleracea* and *Tipula paludosa;* from the order of the thrips (Thysanoptera), for example, *Frankliniella fusca, Frankliniella occidentalis, Frankliniella tritici, Scirtothrips citri, Thrips oryzae, Thrips palmi, Thrips tabaci;* from the order of the Hymenopters, for example, *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of the Heteroptera, for example, *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor;* from the order of the Homoptera, for example, *Acyrthosiphon onobrychis, Adelges laricis, Ahidula nasturtii, Aphis fabae, Aphis pomi, Aphis sambuci, Brachycaudus cardui, Brevicornyne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rasae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of the termites (Isoptera), for example, *Calotermes falvicollis, Leucotermes flavipes, Reticulitermes lucifugus* and *Termes natalensis;* from the order of the Orthoptera, for example, *Acheta domestica, Blatta orientalis, Blattella germanica, Forficula auricularia, Gryllotalpa gryllotalpa, Locusta micrgatoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* from the class of the Arachnoidea, for example, acarina, such as *Amblyomma americanum, Amglyomma variegatum, Argas persicus, Boophililus annulatus, Boohilus decolaratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae;* from the class of the nematodes, for example, root gall nematodes, for example *Meloidogyne hapla, Meloidogyne incognita, Meloidogny javanica,* cyst-forming Nematoden, e.g., *Globodera rostochiensis, Heterodera avenae, Heterodera glycinae, Heterodera schatii, Hetrodera triflolii,* stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients can be used as such, in the form of their formulations or in the application forms prepared therefrom, for example in the form of directly sprayable solutions, powders, suspensions or dispersions, emulsions, oil dispersions, pastes, dusting agents, broadcasting agents or granules, by spraying, atomizing, dusting, broadcasting or pouring. The application forms depend entirely on the intended uses; they should in any case ensure very fine distribution of the novel active ingredients.

For the preparation of directly sprayable solutions, emulsions, pastes or oil dispersions, mineral oil fractions having a medium to high boiling point, such as kerosene or diesel oil, and coal tar oils and oils of vegetable or animal origin, aliphatic, cyclic and aromatic hydrocarbons, e.g., benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, as strongly polar solvents, e.g., dimethylformamide, dimethyl sulfoxide, N-methylpyrrolidone or water, are suitable.

Aqueous application forms can be prepared from emulsion concentrations, pastes or wettable powders (spray powders, oil dispersion) by adding water. For the preparation of emulsions, pastes or oil dispersions, the substances as such can be dissolved in an oil or solvent and can be homogenized in water by means of wetting agents, adhesives, dispersants or emulsifiers. However, concentrates which consist of active substance, wetting agents, adhesives, dispersants or emulsifiers and, if required, solvents or oil and which are suitable for dilution with water can also be prepared.

Suitable surfactants are alkali metal, alkaline earth metal and ammonium salts of ligninsulfonic acid, naphthalenesulfonic acid, phenolsulfonic acid and dibutylnaphthalenesulfonic acid, alkylarylsulfonates, alkylsulfates, alkylsulfaonates, fatty alcohol sulfates and fatty acids and their alkali metal and alkaline earth metal salts, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active substances together with a solid carrier.

The formulations contain in general for 0.01 to 95, preferably from 0.1 to 90, % by weight of the active ingredient. The active ingredients are used in a purity of from 90 to 100%, preferably from 95 to 100% (according to NMR spectrum).

Examples of formulations are:

I. 5 parts by weight of compound No. 1.010 are thoroughly mixed with 95 parts by weight of finely divided kaolin. A dusting agent which contains 5% by weight of the active ingredient is obtained in this manner.

30 parts by weight of compound No. 1.001 are thoroughly mixed with a mixture of 92 parts by weight of silica gel powder and 8 parts by weight of liquid paraffin which has been sprayed onto the surface of this silica gel. A formulation of the active ingredient having good adhesion (active ingredient content 23% by weight) is obtained in this manner.

III. 10 parts by weight of compound No. 1.013 are dissolved in a mixture which consists of 90 parts by weight of xylene, 6 parts by weight of the adduct of from 8 to 10 moles of ethylene oxide with 1 mole of oleic acid N-monoethanolamide, 2 parts by weight of the calcium salt of dodecylbenzenesulfonic acid and 2 parts by weight of the adduct of 40 moles of ethylene oxide with 1 mole of castor oil (active ingredient content 9% by weight).

IV. 20 parts by weight of compound No. 1.007 are dissolved in a mixture which consists of 60 parts by weight of cyclohexanone, 30 parts by weight of isobutanol, 5 parts by weight of the adduct of 7 moles of ethylene oxide with 1 mole of isooctylphenol and 5 parts by weight of the adduct of 40 moles of ethylene oxide with 1 mole of castor oil (active ingredient content 16% by weight).

V. 80 parts by weight of compound No. 1.008 are thoroughly mixed with 3 parts by weight of the sodium salt of diisobutylnaphthalene-alpha-sulfonic acid, 10 parts by weight of the sodium salt of a ligninsulfonic acid obtained from a sulfite waste liquor and 7 parts by weight of silica gel powder, and the mixture is milled in a hammer mill (active ingredient content 80% by weight).

VI. 90 parts by weight of a compound No. 1.003 are mixed with 10 parts by weight of N-methyl-60-pyrrolidone, and a solution which is suitable for the use in the form of very small drops is obtained (active ingredient content 90% by weight).

VII. 20 parts by weight of compound No. 1.005 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

VIII. 20 parts by weight of active ingredient No. 1.011 are thoroughly mixed with 3 parts by weight of the sodium salt of diisobutylnaphthalene-60-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g., ammonium sulfate, ammonium phosphate, ammonium nitrate and ureas, and vegetable products, such as cereal meal, ground bark, woodmeal, nutshell meal and cellulose powder, and other solid carriers.

The active ingredient concentrations in the ready-to-use formulations can be varied within wide ranges.

In general, they are from 0.0001 to 10%, preferably from 0.01 to 1%.

The active ingredients can also be successfully used by the ultra low volume method (ULV), it being possible to apply formulations containing more than 95% of active ingredient or even the active ingredient without additives.

The application rate of active ingredient under open air conditions is from 0.001 to 10, preferably from 0.1 to 1, kg/ha.

Oils of various types, herbicides, fungicides, other crop protection agents and bactericides can be added to the active ingredients, if necessary directly before application (tank mix). These agents can be added to the novel agents in a weight ratio of from 1:10 to 10:1.

EXAMPLES OF SYNTHESIS

The working methods described in the examples of synthesis below were used for preparing further compounds I with appropriate modification of the starting materials. The compounds thus obtained are listed in the Tables below together with physical data.

Preparation of 1-[(5-cyclopropyl-1,3,4-thiadiazol-2-yl)-methoxy]-4-(4,5-dichloroimidazol-1-ylmethoxy)-benzene

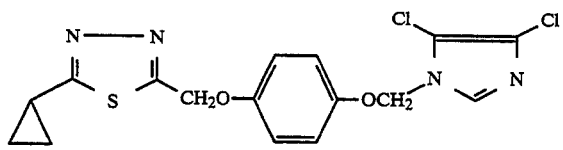

a) 4-tert-Butoxy-1-[(5-cyclopropyl-1,3,4-thiadiazol-2-yl)-methoxy]-benzene

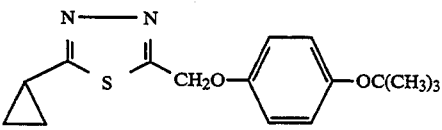

28.5 g (0.172 mol) of 4-tert-butoxyphenol in 260 cm$^3$ of dimethylformamide (DMF) are added dropwise to 5.7 g of 80% strength sodium hydride (0.19 mol) in 37 cm$^3$ of DMF. The mixture is stirred for two hours at from 40 to 50° C. and then cooled to 25° C., and 30 g of 2-chloromethyl-5-cyclopropyl-1,3,4-thiadiazole in 250 cm$^3$ of DMF are added. Stirring is carried out for 5 hours at 80° C., after which the solvent is removed, the residue is taken up in water and the solution is extracted with ethyl acetate. The organic phase is dried and evaporated down.

After flash chromatography over silica gel using cyclohexane/ethyl acetate as the mobile phase, the desired product is obtained as white crystals of melting point 53°–55° C., in a yield of 50.5% of theory.

b) 1[(5-Cyclopropyl-1,3,4-thiadiazol-2-yl)-methoxy]-4-hydroxybenzene

A few drops of aqueous hydrochloric acid are added to 26.4 g of the product from a) in 215 cm$^3$ of ethanol and the mixture is refluxed for 8 hours. Evaporation gives the desired product as a white powder of melting point 79°–83° C., in quantitative yield.

c) 1-[(5-Cyclopropyl-1,3,4-thiadiazol-2-yl)-methoxy]-4-(4,5-dichloroimidazol-1-ylmethoxy)-ben 4.7 g (0.0191 mol) of the product from b) in 25 cm$^3$ of DMF are added dropwise to 0.63 g (0.021 mol) of 80% strength sodium hydride in 6 cm$^3$ of DMF at 25° C. The mixture is stirred for 30 minutes at 25° C., after which 3.54 g (0.0191 mol) of 4,5-dichloro-1-chloromethylimidazole in 10 cm$^3$ of DMF are added. Heating is carried out for 4 hours at 80° C., after which the solvent is removed, the residue is taken up in water and the solution is extracted with ethyl acetate. The organic phase is dried and evaporated down to give the crude product. After flash chromatography over silica gel using cyclohexane/ethyl acetate as the mobile phase, the desired product is obtained as colorless crystals of melting point 108°–109° C., in a yield of 5.0 g (66% of theory).

IR: (fingerprint region; cm$^{-1}$) 1510, 1257, 1236, 1227, 1202, 1034, 825.

TABLE 1
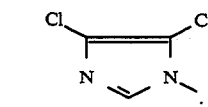
| Example no. | X | A | R¹ | B | Y | Phys. data [mp(°C.); NMR (δ in ppm)] |
|---|---|---|---|---|---|---|
| 1.001 | 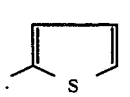 | CH₂ | H | CH₂ | 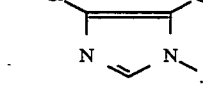 | 121 |
| 1.002 | 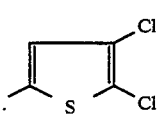 | CH₂ | H | CH₂ | 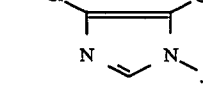 | 128 |
| 1.003 | 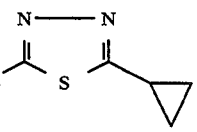 | CH₂ | H | CH₂ | 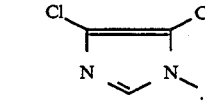 | 108–109 |
| 1.004 | 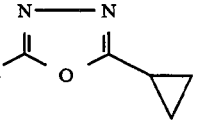 | CH₂ | H | CH₂ | 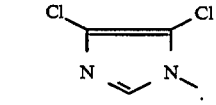 | 70–71 |
| 1.005 | 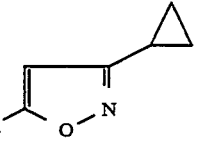 | CH₂ | H | CH₂ | 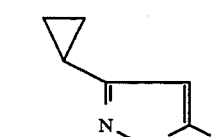 | 123 |
| 1.006 | 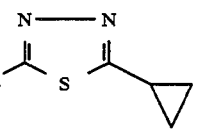 | CH₂ | H | CH₂ | 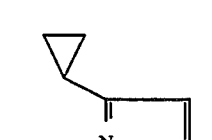 | 102 |
| 1.007 | 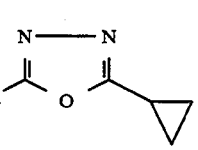 | CH₂ | H | CH₂ | 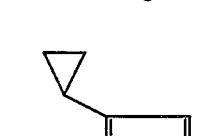 | 91 |
| 1.008 |  | CH₂ | H | CH₂ | 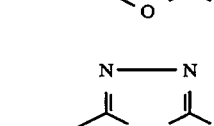 | 117 |
| 1.009 | 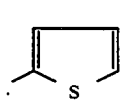 | CH₂ | H | CH₂ |  | 97–98 |

TABLE 1-continued

Structure I: X—A—O—[phenyl with R¹]—O—B—Y

| Example no. | X | A | R¹ | B | Y | Phys. data [mp(°C.); NMR (δ in ppm)] |
|---|---|---|---|---|---|---|
| 1.010 | 1,3,4-thiadiazol-2-yl with cyclopropyl (N=N, S) | CH₂ | H | CH₂ | 5-bromothien-2-yl | 86–87 |
| 1.011 | 1,3,4-thiadiazol-2-yl with cyclopropyl | CH₂ | H | CH₂ | 4,5-dichlorothien-2-yl | 121 |
| 1.012 | 1,3,4-thiadiazol-2-yl with cyclopropyl | CH₂ | H | CH₂ | 1,3,4-oxadiazol-2-yl with cyclopropyl | 74 |
| 1.013 | 1,3,4-thiadiazol-2-yl with cyclopropyl | CH₂ | H | CH₂ | 1,3,4-thiadiazol-2-yl with cyclopropyl | 118–120 |
| 1.014 | 1,3,4-thiadiazol-2-yl with CH₃ | CH₂ | H | CH₂ | 3-methylisoxazol-5-yl | 120–125 |
| 1.015 | 1,3,4-thiadiazol-2-yl with CH₃ | CH₂ | H | CH₂ | 3-isopropylisoxazol-5-yl | 82–83 |
| 1.016 | 1,3,4-thiadiazol-2-yl with CH₃ | CH₂ | H | CH₂ | 3-cyclopropylisoxazol-5-yl | 98–100 |
| 1.017 | 1,3,4-thiadiazol-2-yl with CH₃ | CH₂ | H | CH₂ | 1,3,4-thiadiazol-2-yl with CH₃ | 165–170 |
| 1.018 | 1,3,4-thiadiazol-2-yl with CH₃ | CH₂ | H | CH₂ | 1,3,4-thiadiazol-2-yl with isopropyl | 120–125 |
| 1.019 | 1,3,4-thiadiazol-2-yl with CH₃ | CH₂ | H | CH₂ | 1,3,4-thiadiazol-2-yl with cyclopropyl | 104–106 |

TABLE 1-continued

Structure I: X—A—O—(phenyl with R¹)—O—B—Y

| Example no. | X | A | R¹ | B | Y | Phys. data [mp(°C.); NMR (δ in ppm)] |
|---|---|---|---|---|---|---|
| 1.020 | 4-methyl-1,3,4-thiadiazol-2-yl (CH₃ on C, S in ring) | CH₂ | H | CH₂ | 5-ethoxy-1,3,4-thiadiazol-2-yl (OCH₂CH₃) | 102–105 |
| 1.021 | 4-methyl-1,3,4-thiadiazol-2-yl | CH₂ | H | CH₂ | 5-methyl-1,3,4-oxadiazol-2-yl (CH₃) | 112–121 |
| 1.022 | 4-methyl-1,3,4-thiadiazol-2-yl | CH₂ | H | CH₂ | 5-isopropyl-1,3,4-oxadiazol-2-yl | 54–58 |
| 1.023 | 4-methyl-1,3,4-thiadiazol-2-yl | CH₂ | H | CH₂ | 5-cyclopropyl-1,3,4-oxadiazol-2-yl | 84–87 |
| 1.024 | 4,5-dichloroimidazol-1-yl | CH₂ | H | CH₂ | 3-methylisoxazol-5-yl | 86–90 |
| 1.025 | 4,5-dichloroimidazol-1-yl | CH₂ | H | CH₂ | 3-isopropylisoxazol-5-yl | 93–95 |
| 1.026 | 4,5-dichloroimidazol-1-yl | CH₂ | H | CH₂ | 5-methyl-1,3,4-thiadiazol-2-yl (CH₃) | 113–117 |
| 1.027 | 4,5-dichloroimidazol-1-yl | CH₂ | H | CH₂ | 5-ethoxy-1,3,4-thiadiazol-2-yl (OCH₂CH₃) | 77–79 |
| 1.028 | 4,5-dichloroimidazol-1-yl | CH₂ | H | CH₂ | 5-isopropyl-1,3,4-oxadiazol-2-yl | A 5,17  B 5,70 |
| 1.029 | 4,5-dichloroimidazol-1-yl | CH₂ | H | CH₂ | 5-methyl-1,3,4-oxadiazol-2-yl (CH₃) | A 5,17  B 5,67 |
| 1.030 | 4,5-dichloroimidazol-1-yl | CH₂ | H | CH₂ | 4-isopropylisoxazol-5-yl | 68–72 |

TABLE 1-continued $$X-A-O-\underset{\underset{|}{R^1}}{C_6H_3}-O-B-Y \quad I$$

| Example no. | X | A | R¹ | B | Y | Phys. data [mp(°C.); NMR (δ in ppm)] |
|---|---|---|---|---|---|---|
| 1.031 | 3-isopropyl-isoxazol-5-yl | CH₂ | H | CH₂ | 3-methyl-isoxazol-5-yl | 76–77 |
| 1.032 | 3-isopropyl-isoxazol-5-yl | CH₂ | H | CH₂ | 3-isopropyl-isoxazol-5-yl | 82–83 |
| 1.033 | 3-isopropyl-isoxazol-5-yl | CH₂ | H | CH₂ | 3-cyclopropyl-isoxazol-5-yl | 79–85 |
| 1.034 | 3-isopropyl-isoxazol-5-yl | CH₂ | H | CH₂ | 2-methyl-5-ethoxy-1,3,4-thiadiazol-yl | 63–66 |
| 1.035 | 3-isopropyl-isoxazol-5-yl | CH₂ | H | CH₂ | 2-methyl-5-cyclopropyl-1,3,4-thiadiazol-yl | 57–60 |
| 1.036 | 3-isopropyl-isoxazol-5-yl | CH₂ | H | CH₂ | 2,5-dimethyl-1,3,4-oxadiazol-yl | 66–69 |
| 1.037 | 3-isopropyl-isoxazol-5-yl | CH₂ | H | CH₂ | 2-methyl-5-isopropyl-1,3,4-oxadiazol-yl | 60–65 |
| 1.038 | 3-isopropyl-isoxazol-5-yl | CH₂ | H | CH₂ | 2-methyl-5-cyclopropyl-1,3,4-oxadiazol-yl | 59–60 |
| 1.039 | 2,5-dimethyl-1,3,4-oxadiazol-yl | CH₂ | H | CH₂ | 3-methyl-isoxazol-5-yl | 123–128 |

TABLE 1-continued $$\text{X—A—O—}\underset{\underset{}{}}{\underset{}{\text{C}_6\text{H}_3(\text{R}^1)}}\text{—O—B—Y} \quad I$$

| Example no. | X | A | R¹ | B | Y | Phys. data [mp(°C.); NMR (δ in ppm)] |
|---|---|---|---|---|---|---|
| 1.040 | H₃C-C(=N-N=)-O- (acetyl-substituted diazo) | CH₂ | H | CH₂ | cyclopropyl-isoxazole | 97–100 |
| 1.041 | H₃C-C(=N-N=)-O- | CH₂ | H | CH₂ | CH₃-C(=N-N=)-S-C(OCH₂CH₃) | 81–85 |
| 1.042 | H₃C-C(=N-N=)-O- | CH₂ | H | CH₂ | CH₃-C(=N-N=)-S-C(cyclopropyl) | 78–80 |
| 1.043 | H₃C-C(=N-N=)-O- | CH₂ | H | CH₂ | CH₃-C(=N-N=)-O-C(CH₃) | 131–134 |
| 1.044 | H₃C-C(=N-N=)-O- | CH₂ | H | CH₂ | CH₃-C(=N-N=)-O-C(CH(CH₃)₂) | 54–61 |
| 1.045 | H₃C-C(=N-N=)-O- | CH₂ | H | CH₂ | CH₃-C(=N-N=)-O-C(cyclopropyl) | 103–105 |
| 1.046 | cyclopropyl-C(=N-N=)-O-C(CH₃) | CH₂ | H | CH₂ | CH₃-C(=N-N=)-O-C(cyclopropyl) | 124–126 |
| 1.047 | cyclopropyl-C(=N-N=)-S-C(CH₃) | CH₂ | H | CH₂ | CH₃-C(=N-N=)-S-C(OCH₂CH₃) | 108–110 |

USE EXAMPLES

The insecticidal action of the compounds of the general formula I is demonstrated in the following experiments.

The active ingredients were formulated
a) as a 0.1% strength solution in acetone, or
b) as a 10% strength emulsion in a mixture consisting of 70 wt % of cyclohexanol, 20 wt % of Nekanil ® LN (LUtensol ® AP6, a spreader-sticker with an emulsifying and dispersing action based on ethoxylated alkylphenols) and 10 wt % of Emulphor ® EL (Emulan ® EL, an emulsifier based on ethoxylated fatty alcohols) and diluted down to the desired concentration with acetone in the case of a) and with water in the case of b).

Upon conclusion of the experiments the lowest concentration was determined at which the compounds, compared with the untreated control experiments, achieved 80 to 100% inhibition or kill (action threshold or minimum concentration).

A) *Aphis fabae*, contact action

Bush beans (*Vicia faba*) under heavy attack from *Aphis fabae* were treated with aqueous formulations of the active ingredients. The kill rate was determined after 24 hours.

In this test, the action threshold of the candidate compounds was 200 to 400 ppm.

B) *Dysdercus intermedius,* ovicide test

Eggs of *Dysdercus intermedius* were attached to standard adhesive strips, which were then wetted with aqueous formulations of the active ingredients. After the larvae in the control experiments had hatched (about 8 days) the kill rate was determined.

In this test, the compounds investigated had action thresholds of 2 to 1000 ppm.

C)

Prodenia litura, breeding experiment 5 caterpillars of development stage L3 (10 to 12 mm) which had not suffered any ascertainable damage in the contact experiment were placed on standard nutrient media which had previously been wetted with aqueous formulations of the active ingredients. The experiments was monitored until the moths in a control experiment (without any active ingredient) emerged. In this experiment, the compounds investigated exhibited action thresholds of 0.4 to 0.000002 ppm.

We claim:

1. A hydroquinone diether of the formula I

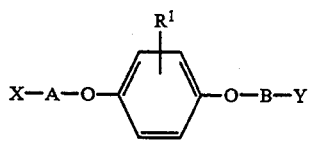

where
$R^1$ is hydrogen, halogen or $C_1$–$C_6$-alkyl,
A and B are each methylene, ethylene or propylene, where these groups may carry one or two $C_1$–$C_3$-alkyl radicals, and
X and Y are each a 5-membered heteroaromatic structure selected from the group consisting of 2-thienyl, 3-thienyl, 3-isoxazolyl, 4-isoxazolyl, 4-isothiazolyl, 5-isothiazolyl, 1-pyrazolyl, 2-oxazolyl, 4-oxazolyl, 5-oxazolyl, 2-thiazolyl, 4-thiazolyl, 5-thiazolyl, 4,5-dichloro-1-imidazolyl, 2-imidazoly, 4-imidazolyl, 5-imidazolyl, 1,2,4-oxadiazol-5-yl, 1,3,4-oxadiazol-2-yl, 1,2,4-thiadiazol-5-yl, 1,3,4-thiadiazol-2-yl, 1,3,4-triazol-1-yl, 1,3,4-triazol-2-yl, 1,2,4-triazol-1-yl, 1,2,4-triazol-3-yl and 1,2,4-triazol-5-yl, which may carry from one to three of the following groups: halogen, $C_1$–$C_6$-alkyl, $C_1$–$C_4$-haloalkyl, $C_1$–$C_6$-alkoxy, $C_1$–$C_4$-haloalkoxy, $C_1$–$C_3$-alkoxy-$C_1$–$C_4$-alkyl, $C_3$–$C_8$-cycloalkyl, $C_2$–$C_8$-alkenyl, phenyl, 1-naphthyl or 2-naphthyl, or $C_1$–$C_{10}$-alkyl which is substituted by phenyl, 1-naphthyl or 2-naphthyl, where these aromatic radicals in turn may carry from one to five halogen atoms and from one to three of the following groups: $C_1$–$C_4$-alkyl, $C_1$–$C_4$-haloalkyl, $C_1$–$C_4$-alkoxy, $C_1$–$C_4$-haloalkyl or $C_1$–$C_4$-alkylthio, with the proviso that at least one of X or Y is selected from the group consisting of 2-thienyl, 5-isoxazolyl, 4,5-dichloro-1-imidazolyl, 1,2,4-oxadiazol-5-yl, 1,3,4-oxadiazol-2-yl, 1,3,4-thiadiazol-2-yl and 1,3,4-triazol-1-yl, which may carry from one to three of the following groups: halogen, $C_1$–$C_6$-alkyl, $C_1$–$C_4$-haloalkyl, $C_1$–$C_6$-alkoxy, $C_1$–$C_4$-haloalkoxy, $C_1$–$C_3$-alkoxy, $C_1$–$C_4$-alkyl, $C_3$–$C_8$-cycloalkyl, $C_2$–$C_8$-alkenyl, phenyl, 1-naphthyl or 2-naphthyl or $C_1$–$C_{10}$-alkyl which is substituted by phenyl, 1-naphthyl or 2-naphthyl, where these aromatic radicals in turn may carry from 1 to 5 halogen atoms and from 1 to 3 of the following groups: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio,
or is 5-isoxazolyl or 5-isoxazolyl substituted by from one to three of the following groups: halogen, $C_1$–$C_6$-alkyl, $C_1$–$C_5$-halo-alkyl, $C_1$–$C_6$-alkoxy, $C_1$–$C_4$-haloalkoxy, $C_1$–$C_3$-alkoxy-$C_1$–$C_4$-alkyl, $C_3$–$C_8$-cycloalkyl, $C_2$–$C_8$-alkenyl, or $C_1$–$C_{10}$-alkyl which is substituted by phenyl, 1-naphthyl or 2-naphthyl, where these aromatic radicals in turn may carry from one to five halogen atoms and from one to three of the following groups: $C_1$–$C_4$-alkyl, $C_1$–$C_4$-haloalkyl, $C_1$–$C_4$-alkoxy, $C_1$–$C_4$-haloalkyl or $C_1$–$C_4$-alkylthio.

2. A compound of the formula I as defined in claim 1, wherein X is 4,5-dichloro-1-imidazolyl.

3. A compound of the formula I as defined in claim 1, wherein X is 3-cyclopropyl-5-isoxazolyl.

4. A compound of the formula I as defined in claim 1, wherein X is 3-(1-methylethyl)-5-isoxazolyl.

5. A compound of the formula I as defined in claim 1, wherein X is 2-cyclopropyl-1,3,4-oxadiazol-2-yl.

6. A compound of the formula I as defined in claim 1, wherein X is 2-methyl-1,3,4-oxadiazol-2-yl.

7. A compound of the formula I as defined in claim 1, wherein X is 2-cyclopropyl-1,3,4-thiadiazol-2-yl.

8. A compound of the formula I as defined in claim 1, wherein X is 2-methyl-1,3,4-thiadiazol-2-yl.

9. A compound of the formula I as defined in claim 1, wherein A is methylene and X is selected from the group consisting of 2-thienyl, 5-isoxazolyl, 1-imidazolyl, 1,2,4-oxadiazol-5-yl, 1,3,4-oxadiazol-2-yl, 1,3,4-thiadiazol-2-yl and 1,3,4-triazol-1-yl, which may carry from one to three of the following groups: halogen, $C_1$–$C_6$-alkyl, $C_1$–$C_4$-haloalkyl, $C_1$–$C_6$-alkoxy, $C_1$–$C_4$-haloalkoxy, $C_1$–$C_3$-alkoxy-$C_1$–$C_4$-alkyl, $C_3$–$C_8$-cycloalkyl or $C_2$–$C_8$-alkenyl.

10. A compound of the formula I as defined in claim 1, wherein A and B are each methylene and X and Y are each selected from the group consisting of 2-thienyl, 5-isoxazolyl, 4,5-dichloro-1-imdazolyl, 1,2,4-oxadiazol-5-yl, 1,3,4-oxadiazol-2-yl, 1,3,4-thiadiazol-2-yl and 1,3,4-triazol-1-yl, which may carry from one to three of the following groups: halogen, $C_1$–$C_6$-alkyl, $C_1$–$C_4$-haloalkyl, $C_1$–$C_6$-alkoxy, $C_1$–$C_4$-haloalkoxy, $C_1$–$C_3$-alkoxy-$C_1$–$C_4$-alkyl, $C_3$–$C_8$-cycloalkyl, $C_2$–$C_8$-alkenyl phenyl, 1-naphthyl or 2-naphthyl or $C_1$–$C_{10}$-alkyl which is substituted by phenyl, 1-naphthyl or 2-naphthyl, where these aromatic radicals in turn may carry from 1 to 5 halogen atoms and from 1 to 3 of the following groups: $C_1$–$C_4$-alkyl, $C_1$–$C_4$-haloalkyl, $C_1$–$C_4$-alkoxy, $C_1$–$C_4$-halo-alkoxy or $C_1$–$C_4$-alkylthio.

11. A insecticidal, arachnicidal and nematocidal composition containing a hydroquinone diether of the formula I as defined in claim 1 and inert additives.

12. A compound of the formula I as defined in claim 1, wherein A and B are each methylene or ethylene.

13. A compound of the formula I as defined in claim 1, wherein at least one of A or B is methylene.

14. A insecticidal, arachnicidal and nematocidal composition containing a hydroquinone diether of the formula I as defined in claim 12 and inert additives.

15. A insecticidal, arachnicidal and nematocidal composition containing a hydroquinone diether of the formula I as defined in claim 10 and inert additives.

16. A method for controlling insects arachnids and nematodes, wherein an effective amount of a hydroquinone diether of the formula I

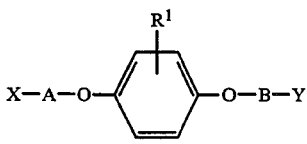

I where

R¹ is hydrogen, halogen or $C_1$–$C_6$-alkyl,

A and B are each methylene, ethylene or propylene, where these groups may carry one or two $C_1$–$C_3$-alkyl radicals, and X and Y are each a 5-membered heteroaromatic structure selected from the group consisting of 2-thienyl, 3-thienyl, 3-isoxazolyl, 4-isoxazolyl, 5-isoxazolyl, 4-isothiazolyl, 5-isothiazolyl, 1-pyrazolyl, 2-oxazolyl, 4-oxazolyl, 5-oxazolyl, 2-thiazolyl, 4-thiazolyl, 5-thiazolyl, 4,5-dichloro-1-imidazolyl, 2-imidazolyl, 4-imidazolyl, 5-imidazolyl, 1,2,4-oxadiazol-5-yl, 1,3,4-oxadiazol-2-yl, 1,2,4-thiadiazol-5-yl, 1,3,4-thiadiazol-2-yl, 1,3,4-triazol-1-yl, 1,3,4-triazol-2-yl, 1,2,4-triazol-1-yl, 1,2,4-triazol-3-yl and 1,2,4-triazol-5-yl, which may carry from one to three of the following groups: halogen, $C_1$–$C_6$-alkyl, $C_1$–$C_4$-haloalkyl, $C_1$–$C_6$-alkoxy, $C_1$–$C_4$-haloalkoxy, $C_1$–$C_3$-alkoxy-$C_1$–$C_4$-alkyl, $C_3$–$C_8$-cycloalkyl, $C_2$–$C_8$-alkenyl, phenyl, 1-naphthyl or 2-naphthyl or $C_1$–$C_{10}$-alkyl which is substituted by phenyl, 1-naphthyl or 2-naphthyl, where these aromatic radicals in turn may carry from one to five halogen atoms and from one to three of the following groups: $C_1$–$C_4$-alkyl, $C_1$–$C_4$-haloalkyl, $C_1$–$C_4$-alkoxy, $C_1$–$C_4$-haloalkyl or $C_1$–$C_4$-alkylthio, with the proviso that at least one of X or Y is selected from the group consisting of 2-thienyl, 5-isoxazolyl, 4,5-dichloro-1-imidazolyl, 1,2,4-oxadiazol-5-yl, 1,3,4-oxadiazol-2-yl, 1,3,4-thiadiazol-2-yl and 1,3,4-triazol-1-yl, which may carry from one to three of the following groups: halogen, $C_1$–$C_6$-alkyl, $C_1$–$C_4$-haloalkyl, $C_1$–$C_6$-alkoxy, $C_1$–$C_4$-haloalkoxy, $C_1$–$C_3$-alkoxy, $C_1$–$C_4$-alkyl, $C_3$–$C_8$-cycloalkyl, $C_2$–$C_8$-alkenyl, phenyl, 1-naphthyl or 2-naphthyl or $C_1$–$C_{10}$-alkyl which is substituted by phenyl, 1-naphthyl or 2-naphthyl, where these aromatic radicals in turn may carry from one to five halogen atoms and from one to three of the following gruops: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, is allowed to act on the insects, arachnids and nematodes and/or their habitat.

17. A method for controlling insects, arachnids and nematodes, wherein an effective amount of a hydroquinone diether of the formula I as defined in claim 12 is allowed to act on the insects, arachnids and nematodes and/or their habitat.

18. A method for controlling insects, arachnids and nematodes, wherein an effective amount of a hydroquinone diether of the formula I as defined in claim 13 is allowed to act on the insects, arachnids and nematodes and/or their habitat.

19. A method for controlling insects, arachnids and nematodes, wherein an effective amount of a hydroquinone diether of the formula I as defined in claim 9 is allowed to act on the insects, arachnids and nematodes and/or their habitat.

20. A method for controlling insects, arachnids and nematodes, wherein an effective amount of a hydroquinone diether of the formula I as defined in claim 10 is allowed to act on the pests and/or their habitat.

* * * * *

UNITED STATES PATENT AND TRADEMARK OFFICE
CERTIFICATE OF CORRECTION

PATENT NO. : 5,374,642
DATED : December 20, 1994
INVENTOR(S) : KARDORFF et al.

It is certified that error appears in the above-indentified patent and that said Letters Patent is hereby corrected as shown below:

Column 78, claim 9, line 30 bridging line 31, "1-imidazolyl" should be --4,5-dichloro-1-imidazolyl--.

Column 78, claim 10, line 40, "imdazolyl" should be --imidazolyl--.

Signed and Sealed this

Twenty-ninth Day of August, 1995

Attest:

BRUCE LEHMAN

*Attesting Officer*          *Commissioner of Patents and Trademarks*